US006281345B1

(12) United States Patent
Tripp et al.

(10) Patent No.: US 6,281,345 B1
(45) Date of Patent: Aug. 28, 2001

(54) PARASITE ASTACIN METALLOENDOPEPTIDASE NUCLEIC ACID MOLECULES AND USES THEREOF

(75) Inventors: Cynthia Ann Tripp, Ft. Collins; Glenn Robert Frank, Wellington; Robert B. Grieve, Fort Collins, all of CO (US)

(73) Assignee: Heska Corporation, Ft. Collins, CO (US)

( * ) Notice: Subject to any disclaimer, the term of this patent is extended or adjusted under 35 U.S.C. 154(b) by 0 days.

(21) Appl. No.: 09/003,570

(22) Filed: Jan. 6, 1998

Related U.S. Application Data

(63) Continuation-in-part of application No. 08/463,994, filed on Jun. 6, 1995, now abandoned, which is a continuation of application No. 08/249,552, filed on May 26, 1994, now abandoned.

(51) Int. Cl.$^7$ .............................. C07H 21/04; C12Q 1/37; C12N 9/00
(52) U.S. Cl. .......................... 536/23.2; 435/24; 435/69.1; 435/183; 435/195
(58) Field of Search .......................... 536/23.2; 435/69.1, 435/24, 195, 183

(56) References Cited

FOREIGN PATENT DOCUMENTS

| 0 524 834 A2 | 1/1993 | (EP) . |
| 93/10225 | 5/1993 | (WO) . |

OTHER PUBLICATIONS

La Cognata et al. Populus hybrid mRNA for Citrate Synthase. Direct Submission. Institute fuer Genbiologische Forschung, Berlin, Accession No. X84227, Jan. 23, 1995.*
Lee et al. Molecular Cloning and characterization of the gene encoding glutathione reductase in Brassica campestris, Direct Submission, Biochim. Biophys. Acta 1385(3): 309–314, 1998.*
Yan et al. Hydra vulgaris metalloproteinase 1 (HMP1) mRNA, Direct Submission, Development 121(6): 1591–1602, Accession No. U22380, 1995.*
Abou, et al., (1992), *Egyptian Journal of Biochemistry*, 10(2):220–233.
Cox et al., (1990), *Mol. Biochem. Parasitol.*, 41:25–34.
Dumermuth et al., (1991), *J. Biol. Chem.*, 266(32):21381–21385.
Eakin et al., (1990) *Mol. Biochem. Parasitol.*, 39:1–8.
Gomis–Rüth et al., (1993), *J. Mol. Biol.*, 229:945–968.
Heussler et al., (1994), *Mol. Biochem. Parasitol.*, 64:11–23.
Jiang et al., (1992) *FEBS Letters*, 312(2,3):110–114.
Kunitz, (1947) "Crystalline Soybean Trypsin" pp. 291–310.
North et al., (1990), *Parasitol. Today*, 6(8):270–275.
Pratt et al., (1992), *Mol. Biochem. Parasitol.*, 51:209–218.
Ray et al., (1992), *Mol. Biochem. Parasitol.*, 51:239–250.
Richer et al., (1993), *Exp. Parasitol.*, 76:1–11.
Richer, (1992), *Diss. Abstr. Int'l.* 53(6):2599–B.
Richer et al., (1992), *Exp. Parasitol.*, 75:213–222.
Sakanari et al., (1989), *Proc. Natl. Acad. Sci. USA*, 86:4863–4867.
Swamy et al., (1983), *Mol. Biochem. Parasitol.*, 9:1–14.
Wilson, et al., (1994), *Nature*, 368:32–38.
Lepage et al., *Development*, 114:147–163 (1992).
Reynolds et al., *Development*, 114:769–786 (1992).

* cited by examiner

*Primary Examiner*—Karen Cochrane Carlson
*Assistant Examiner*—Holly Schnizer
(74) *Attorney, Agent, or Firm*—Sheridan Ross P.C.

(57) ABSTRACT

The present invention relates to parasite astacin metalloendopeptidase proteins, nucleic acid molecules having sequences that encode such proteins, antibodies raised against such proteins and compounds that can inhibit the activities of parasite astacin metalloendopeptidases. The present invention also includes methods to obtain such nucleic acid molecules, proteins, antibodies and inhibitors. The present invention also includes therapeutic compositions comprising such nucleic acid molecules, proteins, antibodies and inhibitors as well as their use to protect animals from disease caused by parasites, such as heartworm infection.

19 Claims, No Drawings

US 6,281,345 B1

PARASITE ASTACIN METALLOENDOPEPTIDASE NUCLEIC ACID MOLECULES AND USES THEREOF

CROSS-REFERENCE TO RELATED APPLICATIONS

This application is a continuation-in-part of U.S. application Ser. No. 08/463,994, filed Jun. 6, 1995, now abandoned which is a continuation of U.S. application Ser. No. 08/249,552, filed May 26, 1994, now abandoned.

FIELD OF THE INVENTION

The present invention relates to novel parasite protease genes, proteins encoded by such genes, antibodies raised against such proteins, and protease inhibitors produced using such proteins. Particular proteases of the present invention include astacin metalloendopeptidases and cysteine proteases. The present invention also includes therapeutic compositions comprising such nucleic acid molecules, proteins, antibodies and inhibitors, as well as their use to protect animals from disease caused by parasites, such as by tissue-migrating helminths such as heartworm.

BACKGROUND OF THE INVENTION

Parasite infections in animals, including humans, are typically treated by chemical drugs, because there are essentially no efficacious vaccines available. One disadvantage with chemical drugs is that they must be administered often. For example, dogs susceptible to heartworm are typically treated monthly to maintain protective drug levels. Repeated administration of drugs to treat parasite infections, however, often leads to the development of resistant strains that no longer respond to treatment. Furthermore, many of the chemical drugs are harmful to the animals being treated, and as larger doses become required due to the build up of resistance, the side effects become even greater.

It is particularly difficult to develop vaccines against parasite infections both because of the complexity of the parasite's life cycle and because, while administration of parasites or parasite antigens can lead to the production of a significant antibody response, the immune response is typically not sufficient to protect the animal against infection.

As for most parasites, the life cycle of *Dirofilaria immitis*, the helminth that causes heartworm, includes a variety of life forms, each of which presents different targets, and challenges, for immunization. Adult forms of the parasite are quite large and preferentially inhabit the heart and pulmonary arteries of an animal. Males worms are typically about 12 centimeters (cm) to about 20 cm long and about 0.7 millimeters (mm) to about 0.9 mm wide; female worms are about 25 cm to about 31 cm long and about 1.0 to about 1.3 mm wide. Sexually mature adults, after mating, produce microfilariae which are only about 300 micrometers ($\mu$m) long and about 7 $\mu$m wide. The microfilariae traverse capillary beds and circulate in the vascular system of dogs in concentrations of about $10^3$ to about $10^5$ microfilariae per milliliter (ml) of blood. One method of demonstrating infection in dogs is to detect the circulating microfilariae.

If dogs are maintained in an insect-free environment, the life cycle of the parasite cannot progress. However, when microfilariae are ingested by female mosquitos during blood feeding on an infected dog, subsequent development of the microfilariae into larvae occurs in the mosquito. The microfilariae go through two larval stages (L1 and L2) and finally become mature third stage larvae (L3) of about 1.1 mm length, which can then be transmitted back to a dog through the bite of the mosquito. It is this L3 stage, therefore, that accounts for the initial infection. As early as three days after infection, the L3 molt to the fourth larval (L4) stage, and subsequently to the fifth stage, or immature adults. The immature adults migrate to the heart and pulmonary arteries, where they mature and reproduce, thus producing the microfilariae in the blood. "Occult" infection with heartworm in dogs is defined as an infection in which no microfilariae can be detected, but the existence of adult heartworms can be determined through thoracic examination.

Both the molting process and tissue migration are likely to involve the action of one or more enzymes, including proteases. Although protease activity has been identified in a number of parasites (including in larval excretory-secretory products) as well as in mammals, there apparently has been no identification of an astacin metalloendopeptidase gene in any parasite or of a cysteine protease gene in any filariid.

Astacin metalloendopeptidases, so-called because of their similarity to the metalloendopeptidase astacin found in crayfish, are a relatively newly recognized class of metalloproteases that have been found in humans, mice and rats as well as apparently in Drosophila fruit flies, Xenopus frogs and sea urchins; see, for example, Gomis-Ruth et al., 1993, *J. Mol. Biol.* 229, 945–968; Jiang et al., 1992, *FEBS Letters* 312, 110–114; and Dumermuth et al., 1991, *J. Biol. Chem.* 266, 21381–21385. Human intestinal and mouse kidney brush border metalloendopeptidases share about 82 percent homology in the amino-terminal 198 amino acids. Both share about 30 percent homology with astacin and with the amino-terminal domain of human bone morphogenetic protein 1. Members of the astacin family share an extended zinc-binding domain motif, the consensus sequence of which was identified by Dumermuth et al., ibid., as being HEXXHXXGFXHE, wherein H is histidine, E is glutamic acid, G is glycine, F is phenylalanine and X can be any amino acid. Gomis-Ruth et al., ibid., define the zinc-binding domain motif as His-Glu-Uaa-Xaa-His-Xaa-Uaa-Gly-Uaa-Xaa-His, wherein Uaa is a bulky apolar residue-containing amino acid. Jiang et al., ibid., disclose not only the extended zinc-binding domain motif, which they represent as HEIGHAIGFXHE (underlined letters being strictly conserved) but also two other sequences conserved between astacin metalloendopeptidases, including RXDRD spanning amino acids from about 15 through about 19 and YDYXSIMHY spanning amino acids from about 50 through about 58, assuming that the first histidine in the extended zinc-binding domain motif is amino acid position 1. The three histidines at positions 1, 5 and 11 appear to be responsible for zinc binding as is the tyrosine at position 58. The glutamic acid at position 2 is responsible for catalysis. Other key amino acids include the glycine at position 8 which is involved in secondary structure and the glutamic acid at position 12 which forms a salt bridge with the amino-terminus of the mature enzyme.

Consensus sequences, particularly around the active sites, have also been identified for serine and cysteine proteases; see, for example, Sakanari et al., 1989, *Proc. Natl. Acad. Sci. USA* 86, 4863–4867. Although cysteine protease genes have been isolated from several mammalian sources and from the nematodes *Haemonchus contortus* (e.g., Pratt et al., 1992, *Mol. Biochem. Parasitol.* 51, 209–218) and *Caenorhabditis elegans* (Ray et al., 1992, *Mol. Biochem. Parasitol.* 51, 239–250), the cloning of such genes does not necessarily predict that the cloning of novel cysteine protease genes will be straight-forward, particularly since the sequences shared by different cysteine proteases are such that probes and primers based on the consensus sequences are highly degenerative.

Heartworm not only is a major problem in dogs, which typically are unable to develop immunity after infection (i.e., dogs can become reinfected even after being cured by chemotherapy), but is also becoming increasingly widespread in other companion animals, such as cats and ferrets. Heartworm infections have also been reported in humans. Other parasite infections are also widespread, and all require better treatment, including preventative vaccine programs and/or targeted drug therapies.

SUMMARY OF THE INVENTION

One embodiment of the present invention is an isolated parasite nucleic acid molecule capable of hybridizing, under stringent conditions, with a *Dirofilaria immitis* astacin metalloendopeptidase gene. Such a nucleic acid molecule, namely a parasite astacin metalloendopeptidase nucleic acid molecule, can include a regulatory region of a parasite astacin metalloendopeptidase gene and/or encode at least a portion of a parasite astacin metalloendopeptidase protein. A preferred nucleic acid molecule of the present invention includes at least a portion of SEQ ID NO:1, of SEQ ID NO:2, SEQ ID NO:29, SEQ ID NO: 30, SEQ ID NO:32 and/or SEQ ID NO:33, or the complement thereof. The present invention also includes recombinant molecules and recombinant cells that include parasite astacin metalloendopeptidase nucleic acid molecules of the present invention. Also included are methods to produce such nucleic acids, recombinant molecules and recombinant cells of the present invention.

Another embodiment of the present invention is an isolated protein that includes a parasite astacin metalloendopeptidase protein or a mimetope of such a protein. A parasite astacin metalloendopeptidase protein of the present invention preferably has astacin metalloendopeptidase activity and/or comprises a protein that, when administered to an animal in an effective manner, is capable of eliciting an immune response against a natural parasite astacin metalloendopeptidase protein. The present invention also includes inhibitors of astacin metalloendopeptidase activity as well as antibodies that recognize (i.e., selectively bind to) a parasite astacin metalloendopeptidase protein and/or mimetope thereof of the present invention. Also included are methods to produce such proteins, inhibitors and antibodies of the present invention.

Yet another embodiment of the present invention is an isolated filariid nematode nucleic acid molecule capable of hybridizing, under stringent conditions, with a *D. immitis* cysteine protease gene. Such a nucleic acid molecule, namely a filariid cysteine protease nucleic acid molecule, can include a regulatory region of a filariid cysteine protease gene and/or encode at least a portion of a filariid cysteine protease protein. A preferred nucleic acid molecule of the present invention includes at least a portion of SEQ ID NO:12. The present invention also includes recombinant molecules and recombinant cells that include filariid cysteine protease nucleic acid molecules of the present invention. Also included are methods to produce such nucleic acids, recombinant molecules and recombinant cells of the present invention.

Another embodiment of the present invention is an isolated protein that includes a filariid cysteine protease protein or a mimetope of such a protein. A filariid cysteine protease protein of the present invention preferably has cysteine protease activity and/or comprises a protein that, when administered to an animal in an effective manner, is capable of eliciting an immune response against a natural filariid cysteine protease protein. The present invention also includes inhibitors of cysteine protease activity as well as antibodies that recognize (i.e., selectively bind to) a filariid cysteine protease protein and/or mimetope thereof of the present invention. Also included are methods to produce such proteins, inhibitors and antibodies of the present invention.

Yet another embodiment of the present invention is a therapeutic composition capable of protecting an animal from disease caused by a parasite. Such a therapeutic composition includes at least one of the following protective compounds: an isolated parasite astacin metalloendopeptidase protein or a mimetope thereof; an isolated parasite nucleic acid molecule capable of hybridizing under stringent conditions with a *D. immitis* astacin metalloendopeptidase gene; an anti-parasite astacin metalloendopeptidase antibody; an inhibitor of astacin metalloendopeptidase activity identified by its ability to inhibit parasite astacin metalloendopeptidase activity; an isolated filariid nematode cysteine protease protein or a mimetope thereof; an isolated filariid nematode nucleic acid molecule capable of hybridizing under stringent conditions with a *D. immitis* cysteine protease gene; an anti-filariid nematode cysteine protease antibody; and an inhibitor of cysteine protease activity identified by its ability to inhibit filariid nematode cysteine protease activity. Also included is a method to protect an animal from disease caused by a parasite that includes administering to the animal in an effective manner a therapeutic composition of the present invention. A preferred therapeutic composition of the present invention is a composition capable of protecting an animal from heartworm.

The present invention also includes a method to identify a compound capable of inhibiting astacin metalloendopeptidase activity of a parasite. Such a method includes (a) contacting an isolated parasite astacin metalloendopeptidase protein with a putative inhibitory compound under conditions in which, in the absence of the compound, the astacin metalloendopeptidase protein has astacin metalloendopeptidase activity; and (b) determining if the putative inhibitory compound inhibits astacin metalloendopeptidase activity. Also included is a test kit to identify a compound capable of inhibiting astacin metalloendopeptidase activity that includes an isolated parasite astacin metalloendopeptidase protein having astacin metalloendopeptidase activity and a means for determining the extent of inhibition of astacin metalloendopeptidase activity in the presence of a putative inhibitory compound.

Also included in the present invention is a method to identify a compound capable of inhibiting cysteine protease activity of a parasite. Such a method includes (a) contacting an isolated filariid cysteine protease protein with a putative inhibitory compound under conditions in which, in the absence of the compound, the filariid cysteine protease protein has cysteine protease activity; and (b) determining if the putative inhibitory compound inhibits cysteine protease activity. Also included is a test kit to identify a compound capable of inhibiting cysteine protease activity of a parasite that includes an isolated filariid cysteine protease protein having cysteine protease activity and a means for determining the extent of inhibition of cysteine protease activity in the presence of a putative inhibitory compound.

DETAILED DESCRIPTION OF THE INVENTION

The present invention includes the discovery that parasites such as *D. immitis* express astacin metalloendopeptidases. As such, the present invention includes nucleic acid molecules encoding such proteins as well as the proteins themselves. To the inventors'knowledge, astacin metalloendopeptidases have been found previously only in humans, mice, rats, crayfish, Drosophila, Xenopus, sea urchins, chorioallontoic membranes of quail eggs, and medaka fish (Oryzias latipes). The present invention also includes the first identification and isolation of nucleic acid molecules encoding filariid nematode cysteine proteases as well as the cysteine proteases themselves, after a difficult and time-consuming search by the inventors for such nucleic acid molecules. Isolated nucleic acid molecules and proteins of the present invention, including homologues of such nucleic acid molecules and proteins, are useful both in protecting animals from parasite infections and in other applications, including those disclosed below.

One embodiment of the present invention is an isolated parasite (or parasitic) astacin metalloendopeptidase protein or a mimetope thereof (i.e., a mimetope of a parasite astacin metalloendopeptidase protein). According to the present invention, an isolated, or biologically pure, protein, is a protein that has been removed from its natural milieu. As such, "isolated" and "biologically pure" do not necessarily reflect the extent to which the protein has been purified. An isolated parasite astacin metalloendopeptidase protein can be obtained from its natural source. Such an isolated protein can also be produced using recombinant DNA technology or chemical synthesis.

As used herein, an isolated parasite astacin metalloendopeptidase protein can be a full-length protein or any homologue of such a protein, such as a protein in which amino acids have been deleted (e.g., a truncated version of the protein, such as a peptide), inserted, inverted, substituted and/or derivatized (e.g., by glycosylation, phosphorylation, acetylation, myristylation, prenylation, palmitation, amidation and/or addition of glycosylphosphatidyl inositol) such that the homologue has astacin metalloendopeptidase activity and/or is capable of eliciting an immune response against a natural *D. immitis* astacin metalloendopeptidase protein. As used herein, an astacin metalloendopeptidase protein, the full-length version of which is a protein that includes an extended zinc-binding domain, has characteristics similar to astacin and other members of the "astacin family of metalloendopeptidases"; see, for example, Dumermuth et al., ibid. A protein having astacin metalloendopeptidase activity is a protein that can cleave proteins in a manner similar to the zinc-dependent protease astacin. Astacin activity is inhibited by metal chelators such as ethylene diamine tetraacetic acid (EDTA) and 1,10-phenanthroline but not by phosphoramidon, an inhibitor of several other metalloproteases including thermolysin and neutral endopeptidases. Tissue inhibitors of metalloproteinases (TIMP1 and TIMP2), which are the best characterized protein inhibitors of zinc endopeptidases, do not demonstrate inhibitory activity with astacin (Stocker and Zwillig, 1995, *Methods of Enzymology*, vol. 248). Astacin activity can be detected by those skilled in the art (see, for example, Dumermuth et al., ibid.). A protein capable of eliciting an immune response against a natural protein is a protein that includes at least one epitope capable of eliciting an immune response (humoral and/or cellular) against that natural protein (such as a *D. immitis* astacin metalloendopeptidase or a *D. immitis* cysteine protease) when the protein (e.g., the natural protein or a homologue thereof) is administered to an animal as an immunogen using techniques known to those skilled in the art. The ability of a protein to effect an immune response can be measured using techniques known to those skilled in the art. Examples of methods to measure an immune response (e.g., antibody detection, resistance to infection) are disclosed herein.

A parasite astacin metalloendopeptidase protein of the present invention, including a homologue of the full-length protein, has the further characteristic of being encoded by a nucleic acid molecule that is capable of hybridizing, under stringent conditions, with (i.e., to) a *D. immitis* astacin imetalloendopeptidase gene. A preferred astacin metalloendopeptidase protein of the present invention is encoded by a nucleic acid molecule capable of hybridizing, under stringent conditions, with at least a portion of the complement of the nucleic acid sequence disclosed in SEQ ID NO:1, SEQ ID NO:2, SEQ ID NO:29, SEQ ID NO: 30, SEQ ID NO:32 and/or SEQ ID NO:33. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid under stringent hybridization conditions. As used herein, stringent hybridization conditions refer to standard hybridization conditions under which nucleic acid molecules (or sequences), including oligonucleotides, are used to identify similar sequences. Such standard conditions are disclosed, for example, in Sambrook et al., *Molecular Cloning: A Laboratory Manual,* Cold Spring Harbor Labs Press, 1989.

Stringent hybridization conditions typically permit isolation of nucleic acid molecules having at least about 70% nucleic acid sequence identity with the nucleic acid molecule being used as a probe in the hybridization reaction. Formulae to calculate the appropriate hybridization and wash conditions to achieve hybridization permitting 30% or less mis-match between two nucleic acid molecules are disclosed, for example, in Meinkoth et al, 1984, *Anal. Biochem* 138, 267–284; Meinkoth et al, ibid, is incorporated by reference herein in its entirety. An example of such conditions includes, but is not limited to, the following: Oligonucleotide probes of about 18–25 nucleotides in length with $T_m$'s ranging from about 50° C. to about 65° C., for example, can be hybridized to nucleic acid molecules typically immobilized on a filter (e.g., nitrocellulose filter) in a solution containing 2×SSPE, 1% Sarkosyl, 5×Denhardts and 0.1 mg/ml denatured salmon sperm DNA at a temperature as calculated using the formulae of Meinkoth et al., ibid. for about 2 to about 12 hours. The filters are then washed 3 times in a wash solution containing 2×SSPE, 1% Sarkosyl at about 55° C. for about 15 minutes each. The filters can be further washed in a wash solution containing 2×SSPE, 1% Sarkosyl at about 55° C. for about 15 minutes per wash. Further examples of such conditions are provided in the Examples section.

It should be noted that the extent of homology required to form a stable hybrid can vary depending on whether the homologous sequences are interspersed throughout the nucleic acid molecules or are clustered (i.e., localized) in distinct regions on the nucleic acid molecules. Also in accordance with present invention, at least a portion of a astacin metalloendopeptidase protein is a protein of sufficient size to have astacin metalloendopeptidase activity and/or to be able to elicit an immune response against a natural parasite astacin metalloendopeptidase.

SEQ ID NO:1, SEQ ID NO:2, SEQ ID NO:29, SEQ ID NO:30, SEQ ID NO:32 and SEQ ID NO:33 represent the nucleotide sequences of six cDNA (complementary DNA) nucleic acid molecules denoted $nDiMPA1_{1299}$, $nDiMPA2_{2126}$, L3 $nDiMPA3_{2292}$, L3 $nDiMPA3_{2076}$, adult nDiMPA3$_{2032}$, and adult nDiMPA3$_{2028}$, respectively, the production of which is disclosed in the Examples. It should be noted that since nucleic acid sequencing technology is not entirely error-free, SEQ ID NO:1, SEQ ID NO:2, SEQ ID NO:29, SEQ ID NO:30, SEQ ID NO:32 and SEQ ID NO:33 represent, at best, apparent nucleic acid sequences of the respective nucleic acid molecules. As will be discussed in greater detail below, nucleic acid molecules nDiMPA1$_{1299}$ and nDiMPA2$_{2126}$ apparently comprise overlapping open reading frames, as deduced from SEQ ID NO:1 and SEQ ID NO:2. Each of the nucleic acid molecules L3 nDiMPA3$_{2292}$ and adult nDiMPA3 $_{2032}$ apparently comprises a single open reading frame as deduced from SEQ ID NO:29 and SEQ ID NO:32, denoted L3 nDiMPA3$_{2076}$ (SEQ ID NO:30) and adult nDiMPA3$_{2028}$ (SEQ ID NO:33), respectively. The deduced amino acid sequences encoded by L3 nDiMPA3$_{2076}$ and adult nDiMPA3 2028 are disclosed, respectively, in SEQ ID NO:31 and SEQ ID NO:34. Nucleic acid molecule nDiMPA1$_{1299}$ apparently comprises three open reading frames, referred to herein as PDiMPA1$_{ORF1}$, PDiMPA1$_{ORF2}$ and PDiMPA1$_{ORF3}$, the deduced amino acid sequences of which are disclosed, respectively, in SEQ ID NO:3, SEQ ID NO:4 and SEQ ID NO:5. Nucleic acid molecule nDiMPA2$_{2126}$ apparently comprises five open reading frames, referred to herein as PDiMPA2$_{ORF1}$, PDiMPA2$_{ORF2}$, PDiMPA2$_{ORF3}$, PDiMPA2$_{ORF4}$ and PDiMPA2$_{ORF5}$, the deduced amino acid sequences of which are disclosed, respectively, in SEQ ID NO:6, SEQ ID NO:7, SEQ ID NO:8, SEQ ID NO:9 and SEQ ID NO:10. That the open reading frames on both nucleic acid molecules are overlapping raises the possibility that translation of a functional astacin metalloendopeptidase in vivo may involve frameshifting. Both SEQ ID NO:1 and SEQ ID NO:2 contain nucleic acid sequences, including stem-loop structures, that, for frameshift viral gene expression, have been implicated in ribosome slowing and, hence, frameshift translation. The presence of stem loop structures in the mRNA could have caused the reverse transcriptase to stutter or misread the mRNA during the Dirofilaria cDNA library construction. This lack of faithful reproduction of the cDNA from the mRNA template could account for the base pairs missing in the original cDNA clones obtained from the library having the nucleic acid sequences SEQ ID NO:1 and SEQ ID NO:2. Alternatively, nucleic acid molecules nDiMPA1$_{1299}$ and nDiMPA2$_{2126}$ may also be the result of alternative splicing patterns.

L3 nDiMPA3$_{2292}$ apparently comprises a single open reading frame, referred to herein as L3 nDiMPA3$_{2076}$ (SEQ ID NO:30), which encodes a protein, namely PDiMPA3$_{6921}$ the deduced amino acid sequence of which is disclosed in SEQ ID NO:31. Adult nDiMPA3$_{2032}$ also apparently comprises a single open reading frame, referred to herein as adult nDiMPA3$_{2028}$ (SEQ ID NO:33), which encodes a protein, namely PDiMPA3$_{6761}$ the deduced amino acid sequence of which is disclosed in SEQ ID NO:34.

SEQ ID NO:11 represents a composite amino acid sequence derived from the five open reading frames encoded by nDiMPA2$_{2126}$. As such, SEQ ID NO:11 is an example of a combination of disclosed open reading frames, in this case a combination of PDiMPA2$_{ORF1}$, PDiMPA2$_{ORF2}$, PDiMPA2$_{ORF3}$, PDiMPA2$_{ORF4}$ and PDiMPA2$_{ORF5}$. The astacin domain of SEQ ID NO:11 has about 29 percent amino acid sequence homology (i.e., identity within comparable regions) with the amino acid sequence of crayfish astacin. As used herein, an astacin domain is an amino acid sequence of about 200 amino acids that shares significant homology with crayfish astacin, which is a 202-amino acid protein. The astacin domain of SEQ ID NO:11 spans from about amino acid positions 98 through 299. The astacin domain of SEQ ID NO:11 also shares about 30 percent, 31 percent, 33 percent and 33 percent homology at the amino acid level with the astacin domains of, respectively, human bone morphogenetic protein 1, mouse kidney brush border metalloendopeptidase, human intestinal brush border metalloendopeptidases and *Xenopus laevis* embryonic protein UVS.2 (using sequences provided in Dumermuth et al., ibid.).

SEQ ID NO:31 represents the deduced amino acid sequence of the single open reading frame of L3 nDiMPA3$_{22921}$ which is represented herein as nucleic acid molecule L3 nDiMPA3$_{2076}$ (SEQ ID NO:30). The astacin domain of SEQ ID NO:31 spans amino acid positions from about 122 through 326. The astacin domain of SEQ ID NO:31 shares about 27.3 percent, 31.7 percent, and 34.1 percent homology at the amino acid level with the astacin domains of, respectively, crayfish astacin, quail astacin and the *C. elegans* R151.5 gene product, (Genbank accession number U00036). SEQ ID NO:31 shows about 81.7% homology with the composite amino acid sequence derived from the five open reading frames encoded by nDiMPA2$_{2126}$ (SEQ ID NO:11).

SEQ ID NO:34 represents the deduced amino acid sequence of the single open reading frame of adult nDiMPA3$_{2032}$, which is represented herein as nucleic acid molecule adult nDiMPA3$_{2028}$ (SEQ ID NO:33). The astacin domain of SEQ ID NO:34 spans from about amino acid positions 122 through 326. The astacin domain of SEQ ID NO:34 shares about 26.3 percent, 31.2 percent, and 34.6 percent homology at the amino acid level with the astacin domains of, respectively, crayfish astacin, quail astacin and the *C. elegans* R151.5 gene product, (Genbank accession number U00036). SEQ ID NO:34 shows about 81.3% homology with the composite amino acid sequence derived from the five open reading frames encoded by nDiMPA2$_{2126}$ (SEQ ID NO:11).

The amino acid sequences presented as SEQ ID NO:31 (L3 PDiMPA3$_{692}$) and SEQ ID NO:34 (adult PDiMPA3$_{676}$) contain three regions of homology which are conserved within about a 61 amino acid region of all known astacins. In L3 PDiMPA3$_{692}$ and adult PDiMPA3$_{676}$, these three regions span about a 60 amino acid sequence corresponding to amino acid positions from about 214 through about 273 of L3 PDiMPA3$_{692}$, and to amino acid positions from about 198 through about 257 of adult PDiMPA3$_{676}$ (as numbered in SEQ ID NO:31 and SEQ ID NO:34, respectively). The first region of homology includes the zinc binding domain, which spans positions from about 214 through about 224 of SEQ ID NO:31 and positions from about 198 through about 208 of SEQ ID NO:34. This first region includes three histidines which are present in all astacins for zinc binding (imidazole zinc ligands) at positions 214, 218 and 224 of SEQ ID NO:31 and at positions 198, 202 and 208 of SEQ ID NO:34, and a glutamate at position 215 of SEQ ID NO:31 and at position 199 of SEQ ID NO:34, which is assumed to be catalytically important in all astacins. In addition, this first region includes a glycine which is important for secondary structure of the protein at position 221 of SEQ ID NO:31 and at position 205 of SEQ ID NO:34, and a glutamate which forms a salt bridge with the amino terminus of the mature astacin protein at position 225 of SEQ ID NO:31 and at position 209 of SEQ ID NO:34.

The second region found in L3 PDiMPA3$_{692}$ and adult PDiMPA3$_{676}$ that is conserved in all known astacins spans amino acid positions 228 through 232 of SEQ ID NO:31 and positions 212 through 216 of SEQ ID NO:34. This second region is a hydrophilic region common to all astacins.

The third region found in L3 PDiMPA3$_{692}$ and adult PDiMPA3$_{676}$ that is conserved in all known astacins spans amino acid positions 265 through 273 of SEQ ID NO:31 and positions 249 through 257 of SEQ ID NO:34, and contains a portion of the zinc binding domain. In particular, the hydroxyl oxygen of the tyrosine at position 273 of SEQ ID NO:31 and position 257 of SEQ ID NO:34 is the fourth amino acid zinc ligand. It has been proposed that the catalytically active zinc ion of astacins is penta-coordinated with a water molecule serving as the fifth zinc ligand (Stocker et al., 1993, Eur. J. Biochem.) In many known astacins, this tyrosine is typically at position 61 from the first amino acid of the zinc binding domain (i.e., 61 amino acids from the first histidine in the first region). In L3 PDiMPA3$_{692}$ and adult PDiMPA3$_{676}$, this tyrosine is at position 60 from the first amino acid of the zinc binding domain (i.e., 60 amino acids from the first histidine in the first region at position 214 of SEQ ID NO:31 and position 198 of SEQ ID NO:34).

A preferred astacin metalloendopeptidase protein of the present invention includes an amino acid sequence having at least about 35 percent, more preferably at least about 45 percent, even more preferably at least about 60 percent and even more preferably at least about 75 percent, amino acid homology with the astacin domain of SEQ ID NO:11 (i.e., with the corresponding regions of the astacin domain of SEQ ID NO:11). A more preferred astacin metalloendopeptidase protein of the present invention includes an amino acid sequence having at least about 40 percent, more preferably at least about 45 percent, even more preferably at least about 60 percent and even more preferably at least about 75 percent, amino acid homology with the astacin domain of SEQ ID NO:31 or SEQ ID NO:34. An even more preferred astacin metalloendopeptidase protein of the present invention includes at least a portion of at least one of the following open reading frames: PDiMPA1$_{ORF1}$, PDiMPA1$_{ORF2}$, PDiMPA1$_{ORF3}$, PDiMPA2$_{ORF1}$, PDiMPA2$_{ORF2}$, PDiMPA2$_{ORF3}$, PDiMPA2$_{ORF4}$, PDiMPA2$_{ORF5}$, L3 PDiMPA3$_{692}$ and adult PDiMPA3$_{676}$, the deduced amino acid sequences of which are disclosed, respectively, in SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:31 and SEQ ID NO:34. Preferred astacin metalloendopeptidase proteins of the present invention include an extended zinc-binding domain motif. More preferred astacin metalloendopeptidase proteins also contain the tyrosine zinc binding amino acid-containing domain as identified by Jiang et al., ibid, and disclosed above.

Parasite astacin metalloendopeptidase protein homologues can be the result of natural allelic variation or natural mutation. Homologues can also be produced using techniques known in the art including, but not limited to, direct modifications to the protein or modifications to the gene encoding the protein using, for example, classic or recombinant DNA techniques to effect random or targeted mutagenesis. Isolated astacin metalloendopeptidase proteins of the present invention, including homologues, can be identified in a straight-forward manner by the proteins ability to effect astacin metalloendopeptidase activity and/or to elicit an immune response against parasite astacin metalloendopeptidase proteins. Examples of such identification techniques are disclosed herein.

The minimum size of an isolated protein of the present invention is sufficient to form an epitope, a size that is typically at least from about 7 to about 9 amino acids. As is appreciated by those skilled in the art, an epitope can include amino acids that naturally are contiguous to each other as well as amino acids that, due to the tertiary structure of the natural protein, are in sufficiently close proximity to form an epitope.

Any parasite astacin metalloendopeptidase is a suitable protein of the present invention. Suitable parasites from which to isolate proteins (including isolation of the natural protein or production of the protein by recombinant or synthetic techniques) include parasitic helminths, protozoa and ectoparasites such as, but not limited to nematodes, cestodes, trematodes, fleas, flies, ticks, lice, true bugs, and protozoa of the genera Babesia, Cryptosporidium, Eimeria, Encephalitozoon, Hepatozoon, Isospora, Leishmania, Neospora, Nosema, Plasmodium, Pneumocystis, Theileria, Toxoplasma and Trypanosoma. Preferred parasites include tissue-migrating parasitic helminths, and particularly tissue-migrating nematodes. Preferred nematodes include filarlid, ascarid, strongyle and trichostrongyle nematodes. Particularly preferred tissue-migrating nematodes include parasites of the genera Acanthocheilonema, Aelurostrongylus, Ancylostoma, Angiostrongylus, Ascaris, Brugia, Bunostomum, Dictyocaulus, Dioctophyme, Dipetalonema, Dirofilaria, Dracunculus, Filaroides, Lagochilascaris, Loa, Mansonella, Muellerius, Necator, Onchocerca, Parafilaria, Parascaris, Protostrongylus, Setaria, Stephanofilaria, Strongyloides, Strongylus, Thelazia, Toxascaris, Toxocara, Trichinella, Uncinaria and Wuchereria. Other particularly preferred nematodes include parasites of the genera Capillaria, Chabertia, Cooperia, Enterobius, Haemonchus, Nematodirus, Oesophagostomum, Ostertagia, Trichostrongylus and Trichuris. Preferred filariid nematodes include Dirofilaria, Acanthocheilonema, Brugia, Dipetalonema, Loa, Onchocerca, Parafilaria, Setaria, Stephanofilaria and Wuchereria filariid nematodes. A particularly preferred parasite is a nematode of the genus Dirofilaria, with D. immitis, the parasite that causes heartworm, being even more preferred.

In accordance with the present invention, a mimetope of a protein refers to any compound that is able to mimic the activity of that protein, often because the mimetope has a structure that mimics the protein. For example, a mimetope of a parasite astacin metalloendopeptidase protein is a compound that has an activity similar to that of an isolated parasite astacin metalloendopeptidase protein of the present invention. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using, for example, antibodies raised against a protein of the present invention.

A preferred parasite astacin metalloendopeptidase protein or mimetope of the present invention is a compound that when administered to an animal in an effective manner, is capable of protecting that animal from disease caused by a parasite that is susceptible to treatment to inhibit astacin metalloendopeptidase activity. As such, the parasite preferably is essentially incapable of causing disease in an animal that is immunized with a parasite astacin metalloendopeptidase protein, and preferably with a *D. immitis* astacin metalloendopeptidase protein, of the present invention. In accordance with the present invention, the ability of a protein or mimetope of the present invention to protect an animal from disease by a parasite refers to the ability of that protein or mimetope to treat, ameliorate and/or prevent disease, including infection leading to disease, caused by the parasite, preferably by eliciting an immune response against the parasite. Such an immune response can include humoral and/or cellular immune responses. Suitable parasites to target include any parasite that is essentially incapable of causing disease in an animal administered a parasite astacin metalloendopeptidase protein of the present invention. As such, a parasite to target includes any parasite that produces a protein having one or more epitopes that can be targeted by a humoral and/or cellular response against a parasite astacin metalloendopeptidase protein of the present invention and/or that can be targeted by a compound that is capable of substantially inhibiting parasite astacin metalloendopeptidase activity, thereby resulting in the reduced ability of the parasite to cause disease in an animal. Suitable and preferred parasites to target include those parasites disclosed above. A preferred class of parasites to target include tissue-migrating parasitic helminths. A particularly preferred nematode helminth to target is *D. immitis*, which causes heartworm.

One embodiment of the present invention is a fusion protein that includes a parasite astacin metalloendopeptidase domain attached to a fusion segment. Inclusion of a fusion segment as part of a protein of the present invention can enhance the protein's stability during production, storage and/or use. Depending on the segment's characteristics, a fusion segment can also act as an immunopotentiator to enhance the immune response mounted by an animal immunized with a protein of the present invention that contains such a fusion segment. Furthermore, a fusion segment can function as a tool to simplify purification of a protein of the present invention, such as to enable purification of the resultant fusion protein using affinity chromatography. A suitable fusion segment can be a domain of any size that has the desired function (e.g., imparts increased stability to a protein, imparts increased immunogenicity to a protein, and/or simplifies purification of a protein). It is within the scope of the present invention to use one or more fusion segments. Fusion segments can be joined to amino and/or carboxyl termini of the astacin metalloendopeptidase-containing domain of the protein. Linkages between fusion segments and astacin metalloendopeptidase-containing domains of fusion proteins can be susceptible to cleavage in order to enable straight-forward recovery of the astacin metalloendopeptidase-containing domains of such proteins. Fusion proteins are preferably produced by culturing a recombinant cell transformed with a fusion nucleic acid molecule that encodes a protein including the fusion segment attached to either the carboxyl and/or amino terminal end of an parasite astacin metalloendopeptidase-containing domain.

Preferred fusion segments for use in the present invention include a glutathione binding domain, such as *Schistosoma japonicum* glutathione-S-transferase (GST) or a portion thereof capable of binding to glutathione; a metal binding domain, such as a poly-histidine segment capable of binding to a divalent metal ion; an immunoglobulin binding domain, such as Protein A, Protein G, T cell, B cell, Fc receptor or complement protein antibody-binding domains; a 20 sugar binding domain such as a maltose binding domain from a maltose binding protein; and/or a "tag" domain (e.g., at least a portion of β-galactosidase, a strep tag peptide, other domains that can be purified using compounds that bind to the domain, such as monoclonal antibodies). More preferred fusion segments include metal binding domains, such as a polyhistidine segment; a maltose binding domain; a strep tag peptide, such as that available from Biometra in Tampa, Fla.; and an S10 peptide. An example of a preferred fusion protein of the present invention is PHIS-PDiMPA2$_{804}$, the production of which is disclosed herein.

Another embodiment of the present invention is a parasite astacin metalloendopeptidase protein that also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one infectious agent.

Examples of multivalent protective compounds include, but are not limited to, a parasite astacin metalloendopeptidase protein attached to one or more other parasite proteins, such to a filariid nematode cysteine protease protein of the present invention. Other examples of multivalent protective compounds include a parasite astacin metalloendopeptidase protein attached to one or more compounds protective against one or more other infectious agents, particularly an agent that infects cats or dogs, such as, but not limited to, calicivirus, distemper virus, feline herpesvirus, feline immunodeficiency virus, feline leukemia virus, feline infectious peritonitis, hepatitis, hookworm, leptospirosis, panleukopenia virus, parvovirus, rabies and toxoplasmosis.

Suitable heartworm multivalent protective proteins include, but are not limited to, a *D. immitis* astacin metalloendopeptidase and/or a *D. immitis* cysteine protease of the present invention attached to at least one other *D. immitis* protein such as, but not limited to, a *D. immitis* Gp29 protein, a *D. immitis* P39 protein, a *D. immitis* P22U protein, a *D. immitis* P22L protein, a *D. immitis* P20.5 protein, a *D. immitis* P4 protein, a *D. immitis* Di22 protein and/or a *D. immitis* protease expressed in L3 and/or L4 larvae, as well as other helminth proteins sharing significant homology with such *D. immitis* proteins. A protein sharing significant homology with another protein refers to the ability of the nucleic acid sequences encoding such proteins to form stable hybridization complexes with each other under stringent hybridization conditions, as described, for example, in Sambrook et al., ibid. U.S. patent application Ser. No. 08/208,885, filed Mar. 8, 1994, entitled "*D. immitis* Gp29 Proteins, Nucleic Acid Molecules and Uses Thereof", discloses *D. immitis* Gp29 proteins and nucleic acid molecules that encode them. U.S. patent application Ser. No. 08/003,389, filed Jan. 12, 1993, entitled "Immunogenic Larval Proteins", discloses a 39-kD (kilodalton) *D. immitis* protein (size determined by Tris glycine SDS-PAGE (sodium dodecyl sulfate polyacrylamide gel electrophoresis)), referred to herein as P39, and a nucleic acid sequence that encodes it. U.S. patent application Ser. No. 08/003,257, filed Jan. 12, 1993, entitled "Reagents and Methods for Identification of Vaccines", discloses 22-kD and 20.5-kD *D. immitis* proteins (sizes determined by Tris glycine SDS-PAGE), referred to herein as P22L and P20.5, and nucleic acid sequences that encode them. U.S. patent application Ser. No. 08/109,391, filed Aug. 19, 1993, entitled "Novel Parasitic Helminth Proteins", discloses *D. immitis* P4 and *D. immitis* P22U, as well as nucleic acid sequences that encode them. U.S. patent application Ser. No. 08/060,500, filed May 10, 1993, entitled "Heartworm Vaccine", discloses a *D. immitis* Di22 protein and a nucleic acid sequence encoding it (included in Genbank data base accession number M82811); Ser. No. 08/060, 500 is a continuation of U.S. patent application Ser. No. 07/683,202, filed Apr. 8, 1991. U.S. patent application Ser. No. 08/153,554, filed Nov. 16, 1993, entitled "Protease Vaccine Against Heartworm", discloses *D. immitis* larval proteases; Ser. No. 08/153,554 is a continuation of U.S. patent application Ser. No. 07/792,209, filed Nov. 12, 1991. Each of these patent applications is incorporated by reference herein in its entirety.

A particularly preferred parasite astacin metalloendopeptidase protein is a protein encoded by at least a portion of SEQ ID NO:1, SEQ ID NO:2, SEQ ID NO:29, SEQ ID NO:30, SEQ ID NO:32 and SEQ ID NO:33, and, as such, is a protein having an amino acid sequence encoded by at least a portion of at least one of the open reading frames encoding an amino acid sequence represented by SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:31 and/or SEQ ID NO:34. Preferred proteins can include combinations of amino acid sequences encoded by such reading frames, such as SEQ ID NO:11, that result in a functional protein. A homology search using these open reading frames indicate that all but SEQ ID NO:10 share significant homology with known members of the astacin metalloendopeptidase family and with a *Caenorhabditis elegans* R151.5 gene product, Genbank accession number U00036 (Wilson et al., 1994, *Nature* 368, 32–38), suggesting that *C. elegans* also encodes a astacin metalloendopeptidase. Particularly well conserved are the extended zinc-binding domain motif and the tyrosine-containing domain motif, the overall sequence homology being about 24 percent. Even more preferred proteins are encoded by single reading frames which encode a protein having an amino acid sequence of SEQ ID NO:31 or SEQ ID NO:34. A homology search using these open reading frames indicate that they also share significant homology with known members of the astacin metalloendopeptidase family and with a *Caenorhabditis elegans* R151.5 gene product, Genbank accession number U00036 (Wilson et al., supra). Again, particularly well conserved are the extended zinc-binding domain motif and the tyrosine-containing domain motif, the overall sequence homology being about 34.5 percent.

Particularly preferred proteins of the present invention include proteins having the astacin domain of SEQ ID NO:11, proteins having the astacin domain of SEQ ID NO:31, proteins having the astacin domain of SEQ ID NO:34, proteins that include these domains (such as, but not limited to, full-length proteins, fusion proteins and proteins providing multivalent protection) and proteins that are truncated homologues of these domains. Even more preferred proteins include PDiMPA28$_{804}$, PHIS-PDiMPA2$_{804}$, L3 PDiMPA3$_{692}$, and adult PDiMPA3$_{676}$.

Another embodiment of the present invention is an isolated parasite nucleic acid molecule capable of hybridizing, under stringent conditions, with a *D. immitis* astacin metalloendopeptidase gene. As used herein, a *D. immitis* astacin metalloendopeptidase gene includes all nucleic acid sequences related to a natural *D. immitis* astacin metalloendopeptidase gene such as regulatory regions that control production of a *D. immitis* astacin metalloendopeptidase protein encoded by that gene (such as, but not limited to, transcription, translation or post-translation control regions) as well as the coding region itself. A parasite astacin metalloendopeptidase nucleic acid molecule of the present invention can include any isolated natural parasite astacin metalloendopeptidase gene or a homologue thereof. A nucleic acid molecule of the present invention can include one or more regulatory regions, full-length or partial coding regions, or combinations thereof. The minimal size of a parasite astacin metalloendopeptidase nucleic acid molecule of the present invention is the minimal size capable of forming a stable hybrid under stringent hybridization conditions. Suitable and preferred parasites are disclosed above.

In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated parasite astacin metalloendopeptidase nucleic acid molecule of the present invention can be obtained from its natural source either as an entire (i.e., complete) gene or a portion thereof capable of forming a stable hybrid with that gene. An isolated parasite astacin metalloendopeptidase nucleic acid molecule can also be produced using recombinant DNA technology (e.g., polymerase chain reaction (PCR) amplification, cloning) or chemical synthesis. Isolated parasite astacin metalloendopeptidase nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a parasite astacin metalloendopeptidase protein of the present invention or to form stable hybrids under stringent conditions with natural isolates.

A parasite astacin metalloendopeptidase nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., astacin metalloendopeptidase activity or ability to elicit an immune response against at least one epitope of a parasite astacin metalloendopeptidase protein) and/or by hybridization with isolated parasite astacin metalloendopeptidase nucleic acids under stringent conditions.

An isolated nucleic acid molecule of the present invention can include a nucleic acid sequence that encodes at least one parasite astacin metalloendopeptidase protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. As heretofore disclosed, parasite astacin metalloendopeptidase proteins of the present invention include, but are not limited to, proteins having full-length astacin metalloendopeptidase coding regions, proteins having partial astacin metalloendopeptidase coding regions, fusion proteins, multivalent protective proteins and combinations thereof.

One embodiment of the present invention is a parasite astacin metalloendopeptidase nucleic acid molecule that is capable of hybridizing under stringent conditions with nucleic acid molecule nDiMPA1$_{1299}$, with nucleic acid molecule nDiMPA2$_{2126}$, with nucleic acid molecule L3 nDiMPA3$_{2292}$, with nucleic acid molecule L3 nDiMPA3$_{2076}$, with nucleic acid molecule adult nDiMPA3$_{2032}$, and/or with nucleic acid molecule adult nDiMPA3$_{2028}$. As such, preferred astacin metalloendopeptidase nucleic acid molecules are capable of forming stable hybrids with nucleic acid molecules represented by SEQ ID NO:1, SEQ ID NO:2, SEQ ID NO:29, SEQ ID NO:30, SEQ ID NO:32 and/or SEQ ID NO:33. Particularly preferred astacin metalloendopeptidase nucleic acid molecules comprise at least a portion of nucleic acid molecule nDiMPA1$_{1299}$, nucleic acid molecule nDiMPA2$_{2126}$, nucleic acid molecule L3 nDiMPA3$_{2292}$, nucleic acid molecule L3 nDiMPA3$_{2076}$, adult nDiMPA3$_{2032}$, and/or adult nDiMPA3$_{2028}$. As such, a preferred nucleic acid molecule of the present invention includes a nucleic acid sequence including at least a portion of SEQ ID NO:1, SEQ ID NO:2, SEQ ID NO:29, SEQ ID NO:30, SEQ ID NO:32 and/or SEQ ID NO:33. Such a nucleic acid molecule can be nDiMPA1$_{1299}$, nDiMPA2$_{2126}$L3 nDiMPA3$_{2292}$, L3 nDiMPA3$_{2076}$, adult nDiMPA3$_{2032}$, and/or adult nDiMPA3$_{2028}$, can include nucleotides in addition to nDiMPA1$_{1299}$, nDiMPA2$_{2126}$, L3 nDiMPA3$_{2292}$, L3 nDiMPA3$_{2076}$, adult nDiMPA3$_{2032}$, and/or adult nDiMPA3$_{2028}$, or can be a truncation fragment of nDiMPA1$_{1299}$, nDiMPA2$_{2126}$, L3 nDiMPA3$_{2292}$, L3 nDiMPA3$_{2076}$, adult nDiMPA3$_{2032}$, and/or adult nDiMPA3$_{2028}$. Particularly preferred nucleic acid molecules include nDiMPA1$_{689}$, nDiMPA1$_{1299}$, nDiMPA2$_{2126}$, nDiMPA2$_{804}$, nDiMPA2$_{271}$, L3 nDiMPA3$_{2292}$, L3 nDiMPA3$_{2076}$, adult nDiMPA3$_{2032}$, adult nDiMPA3$_{2028}$, and BvMPA2, the production of which are disclosed in the Examples.

One preferred embodiment of the present invention is a parasite astacin metalloendopeptidase nucleic acid molecule capable of hybridizing to the complement of the coding strand of a nucleic acid molecule encoding at least one open reading frame encoding at least one of the following amino acid sequences: SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:31 and SEQ ID NO:34. Preferably, such a nucleic acid molecule encodes a protein that shares at least about 35 percent, more preferably at least about 45 percent, even more preferably at least about 60 percent and even more preferably at least about 75 percent amino acid homology with SEQ ID NO:11. Even more preferably, such a nucleic acid molecule encodes a protein that shares at least about 40 percent, more preferably at least about 45 percent, even more preferably at least about 60 percent and even more preferably at least about 75 percent amino acid homology with SEQ ID NO:31 and/or SEQ ID NO:34. More preferred astacin metalloendopeptidase nucleic acid molecules encode at least a portion of at least one of such open reading frames. Particularly preferred astacin metalloendopeptidase nucleic acid molecules are capable of forming stable hybrids with nucleic acid molecules encoding an extended zinc-binding domain motif (i.e., to the carboxyl terminus of the motif as well as to the general zinc-binding domain) and, more preferably, also with nucleic acid molecules encoding other disclosed conserved domains of astacin metalloendopeptidases, such as the motif that contains the tyrosine believed to bind to zinc.

Knowing the nucleic acid sequence of certain parasite astacin metalloendopeptidase nucleic acid molecules of the present invention allows one skilled in the art to make copies of those nucleic acid molecules as well as to obtain nucleic acid molecules including at least a portion of such nucleic acid molecules and other parasite astacin metalloendopeptidase nucleic acid molecule homologues. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify include parasite larval (especially L3, L4) and adult cDNA libraries as well as genomic DNA libraries. Similarly, preferred DNA sources to screen or from which to amplify include parasite larval (especially L3, L4) and adult cDNA and genomic DNA. Techniques to clone and amplify genes are disclosed, for example, in Sambrook et al., ibid.

The present invention also includes nucleic acid molecules that are oligonucleotides capable of hybridizing, under stringent conditions, with complementary regions of other, preferably longer, nucleic acid molecules of the present invention, such as to complementary regions of a parasite astacin metalloendopeptidase gene, including complementary regions of a D. immitis astacin metalloendopeptidase gene. Such oligonucleotides can hybridize under stringent conditions with complementary regions of nDiMPA1$_{1299}$, nDiMPA2$_{2126}$, L3 nDiMPA3$_{2292}$, L3 nDiMPA3$_{2076}$, adult nDiMPA3$_{2032}$, or adult nDiMPA3$_{2028}$, complementary regions of nucleic acid molecules that include at least a portion of nDiMPA1$_{1299}$, nDiMPA2$_{2126}$, L3 nDiMPA3$_{2292}$, L3 nDiMPA3$_{2076}$, adult nDiMPA3$_{2032}$, or adult nDiMPA3$_{2028}$, and complementary regions of nucleic acid molecules that hybridize under stringent conditions with nDiMPA1$_{1299}$, nDiMPA2$_{2126}$, L3 nDiMPA3$_{2292}$, L3 nDiMPA3$_{2076}$, adult nDiMPA3$_{2032}$, or adult nDiMPA3$_{2028}$. Such oligonucleotides can be RNA, DNA, or derivatives of either. The minimal size of such oligonucleotides is the size required to form a stable hybrid between a given oligonucleotide and the complementary sequence on another nucleic acid molecule of the present invention. As such, the size is dependent on nucleic acid composition and percent homology between the oligonucleotide and complementary sequence as well as upon hybridization conditions per se (e.g., temperature, salt concentration). For AT-rich nucleic acid sequences, such as those of parasitic helminths, oligonucleotides typically are at least about 15 to about 17 bases in length. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit, for example, expression of astacin metalloendopeptidases by a parasite. Such therapeutic applications include the use of such oligonucleotides in, for example, antisense-, triplex formation-, ribozyme- and/or RNA drug-based technologies.

The present invention, therefore, includes such oligonucleotides and methods to interfere with the production of astacin metalloendopeptidase proteins by use of one or more of such technologies. Appropriate oligonucleotide-containing therapeutic compositions can be administered to an animal, using techniques known to those skilled in the art, either prior to or after infection by a parasite such as *D. immitis*, in order to protect the animal from disease.

Another embodiment of the present invention is an isolated filariid nematode cysteine protease protein or a mimetope thereof. As used herein, an isolated filariid nematode, or filariid, cysteine protease protein can be a full-length filariid cysteine protease protein or any homologue of such a protein. Filariid nematode cysteine protease proteins, including homologues thereof, can be isolated and produced according to the methods disclosed herein for parasite astacin metalloendopeptidase proteins. Homologues and mimetopes of filariid cysteine protease proteins are defined in a similar manner as are homologues and mimetopes of parasite astacin metalloendopeptidase proteins. Filariid cysteine protease proteins (including homologues) and mimetopes thereof each are capable of eliciting an immune response (i.e., having at least one epitope capable of eliciting an immune response) against a filariid cysteine protease protein and/or are capable of effecting cysteine protease activity. Cysteine protease activity, as well as the ability of a protein to effect an immune response, can be measured using techniques known to those skilled in the art. Cysteine protease activity can be measured by its ability to cleave peptides having a cysteine protease cleavage site, such as z-Val-Leu-Arg-AMC; such activity can be inhibited by, for example, by the cysteine protease inhibitor E-64 (available from Boehringer Mannheim, Indianapolis, Ind.). Preferred filariids are disclosed herein. A particularly preferred filariid is *D. immitis*.

A filariid cysteine protease protein of the present invention, including any homologue thereof, has the additional characteristic of being encoded by a nucleic acid molecule that is capable of hybridizing, under stringent conditions, with the complement of the coding strand of a nucleic acid molecule comprising at least a portion of a nucleic acid sequence encoding a filariid cysteine protease protein. Preferred proteins are encoded by a nucleic acid molecule that forms stable hybrids with at least a portion of $nDiCP_{1431}$, the production of which is described in detail in the Examples. SEQ ID NO:12 represents the deduced sequence of $nDiCP_{143}$, the deduced translation product of which is a 47 amino acid sequence represented in SEQ ID NO:13, the protein being denoted $PDiCP_{143}$. It should be noted that since nucleic acid sequencing technology is not entirely error-free, SEQ ID NO:12, at best, represents an apparent nucleic acid sequence of a nucleic acid molecule encoding at least a portion of full-length *D. immitis* cysteine protease. Furthermore, SEQ ID NO:13 apparently represents an internal amino acid sequence of *D. immitis* cysteine protease since SEQ ID NO:12 apparently has neither a start nor stop codon. SEQ ID NO:13, however, includes amino acid sequences that are conserved among a number of cysteine proteases.

A comparison of SEQ ID NO:13 with the corresponding regions of known parasite cysteine protease genes indicates that SEQ ID NO:13 shares about 16 percent, about 22 percent, about 24 percent, about 35 percent, about 39 percent, about 44 percent and about 49 percent homology at the amino acid level with cysteine proteases from, respectively, *H. contortus* (a nematode), *Schistosoma mansoni* (a trematode), *C. elegans* (a nematode), *Fasciola hepatica* (a trematode), *Entamoeba histolytica* (a protozoa), *Trypanosoma cruzi* (a protozoa) and *T. brucie*. SEQ ID NO:13 also shares about 50 percent amino acid homology with human cathepsin L, about 45 percent amino acid homology with chicken cathepsin L and about 56 percent amino acid homology with a *Paragonimus westermani* (trematode) cysteine protease. The serine at about position 30 and the cysteine at about position 37 of SEQ ID NO:13 are conserved in all of these cysteine proteases. Please see, for example, the following for listings of the above-referenced sequences: Heussler et al., 1994, *Mol. Biochem. Parasitol.* 64, 11–23; Eakin et al., 1990, *Mol. Biochem. Parasitol.* 39, 1–8; Ray et al., ibid., Pratt et al., ibid., Sakanari et al., ibid.; European Patent Application Publication No. 0524834A2, by Hamajima et al., published Jan. 27, 1993.

Preferred filariid cysteine protease proteins of the present invention include amino acid sequences that share at least about 60 percent, more preferably at least about 70 percent, and even more preferably at least about 80 percent, homology with SEQ ID NO:13. Particularly preferred filariid cysteine protease proteins of the present invention include $PDiCP_{142}$, proteins that include $PDiCP_{142}$ (including, but not limited to full-length proteins, fusion proteins and multivalent protective proteins), and proteins that include at least a portion of $PDiCP_{142}$.

A preferred filariid cysteine protease protein or mimetope thereof is a compound that when administered to an animal in an effective manner, is capable of protecting that animal from disease caused by a parasite that is susceptible to treatment with a composition that inhibits cysteine protease activity. A suitable parasite to target is any parasite that produces a protein having one or more epitopes that can be targeted by a humoral and/or cellular response against a filariid nematode cysteine protease protein of the present invention and/or that can be targeted by a compound that is capable of substantially inhibiting filariid cysteine protease activity, thereby resulting in the reduced ability of the parasite to cause disease in an animal. Suitable and preferred parasites are disclosed above. A preferred class of parasites to target include tissue-migrating parasitic helminths. A particularly preferred nematode to target is *D. immitis*, which causes heartworm.

Also included in the present invention are fusion proteins and multivalent protective proteins that include at least one filariid cysteine protease protein. Such proteins can comprise fusion segments and/or multiple protective domains similar as disclosed for parasite astacin metalloendopeptidase proteins and can be produced in a similar manner as described for parasite astacin metalloendopeptidase proteins of the present invention. Particularly preferred fusion proteins include $PHIS-PDiCP_{142}$.

Yet another embodiment of the present invention is an isolated filariid nematode nucleic acid molecule capable of hybridizing, under stringent conditions, with a *D. immitis* cysteine protease gene. Such a nucleic acid molecule is referred to as a filariid nematode, or filariid, cysteine protease nucleic acid molecule. As used herein, a filariid cysteine protease gene includes all nucleic acid sequences related to a natural filariid cysteine protease gene such as regulatory regions that control production of a *D. immitis* cysteine protease protein encoded by that gene as well as the coding region itself. A filariid cysteine protease nucleic acid molecule of the present invention can include an isolated natural filariid cysteine protease gene or a homologue thereof. A nucleic acid molecule of the present invention can include one or more regulatory regions, full-length or partial coding regions, or combinations thereof. The minimal size of a filariid cysteine protease nucleic acid molecule of the present invention is the minimal size capable of forming a stable hybrid under stringent hybridization conditions with a D. immitis cysteine protease gene. Filariid immitis cysteine protease nucleic acid molecules can be isolated and produced according to the methods taught herein for the production and isolation of parasite astacin metalloendopeptidase nucleic acid molecules. Cysteine protease nucleic acid molecule homologues can be selected from a mixture of modified nucleic acids by screening for the function of the protein encoded by the nucleic acid (e.g., cysteine protease activity and/or ability to elicit an immune response against at least one epitope of a filariid cysteine protease protein) and/or by hybridization with isolated D. immitis cysteine protease nucleic acids under stringent conditions.

An isolated filariid cysteine protease nucleic acid molecule of the present invention can include a nucleic acid sequence that encodes at least one filariid cysteine protease protein of the present invention, examples of such proteins being disclosed herein. As heretofore disclosed, filariid cysteine protease proteins of the present invention include, but are not limited to, proteins having full-length filariid cysteine protease coding regions, proteins having partial filariid cysteine protease coding regions, fusion proteins, multivalent protective proteins and combinations thereof. The present invention also includes nucleic acid molecules encoding filariid cysteine protease proteins that have been modified to accommodate codon usage properties of the cells in which such nucleic acid molecules are to be expressed.

One embodiment of the present invention is a filariid cysteine protease nucleic acid molecule that includes a nucleic acid sequence that is capable of hybridizing under stringent conditions with D. immitis nucleic acid molecule $nDiCP_{143}$, the deduced sequence of which is disclosed in SEQ ID NO:12. Preferred filariid cysteine protease nucleic acid molecules encode proteins having at least about 60 percent, more preferably at least about 70 percent and even more preferably at least about 80 percent, amino acid homology with SEQ ID NO:13. More preferred is a nucleic acid molecule that encodes a D. immitis cysteine protease protein that comprises at least a portion of SEQ ID NO:13.

A preferred nucleic acid molecule of the present invention includes at least a portion of D. immitis nucleic acid molecule $nDiCP_{143}$. Such a nucleic acid molecule can be $nDiCP_{143}$, can include nucleotides in addition to $nDiCP_{143}$ (such as, but not limited to, a nucleic acid molecule encoding a full-length protein, a nucleic acid molecule encoding a fusion protein, or a nucleic acid molecule encoding a multivalent protective compound), or can be a truncation fragment of $nDiCP_{143}$. Particularly preferred filariid cysteine protease nucleic acid molecules include $nDiCP_{143}$ and $nDiCP_{142}$.

The inventors of the present invention had difficulty isolating a D. immitis cysteine protease nucleic acid molecule despite the wide variety of cysteine protease genes that have been cloned. Primers designed by the inventors using consensus sequences derived from known cysteine protease genes, including from known parasite cysteine protease genes, had a degeneracy that was essentially too great to pull out a D. immitis cysteine protease gene. The inventors discovered that use of primers that incorporated D. immitis codon usage bias enabled the identification of the first D. immitis cysteine protease nucleic acid molecule, namely $nDiCP_{143}$.

Having identified the nucleic acid molecule $nDiCP_{143}$, it is likely that one skilled in the art can make copies of that nucleic acid molecule as well as obtain other filariid nematode cysteine protease nucleic acid molecules including full-length genes and homologues thereof. Such nucleic acid molecules can be obtained in a variety of ways such as those described for the isolation and production of parasite astacin metalloendopeptidase nucleic acid molecules of the present invention. Preferred libraries to screen or from which to amplify include filariid larval (especially L3, L4) and adult cDNA libraries and filariid genomic DNA libraries. Similarly, preferred DNA sources to screen or from which to amplify include filariid larval (especially L3, L4) and adult cDNA, as well as filariid genomic DNA. Preferred primers and probes to use are codon-biased for the given filariid.

The present invention also includes nucleic acid molecules that are oligonucleotides capable of hybridizing, under stringent conditions, with complementary regions of other, preferably longer, nucleic acid molecules of the present invention, such as to complementary regions of a filariid cysteine protease gene. Such oligonucleotides can hybridize under stringent conditions with complementary regions of $nDiCP_{143}$, complementary regions of nucleic acid molecules that include at least a portion of $nDiCP_{143}$, and complementary regions of nucleic acid molecules that hybridize under stringent conditions with $nDiCP_{143}$. Such oligonucleotides can be RNA, DNA, or derivatives of either. Other criteria, such as minimal size, as well as methods to produce and use such oligonucleotides are as disclosed for parasite astacin metalloendopeptidase oligonucleotides of the present invention.

The present invention also includes a recombinant vector, which includes at least one nucleic acid molecule of the present invention (e.g., a parasite astacin metalloendopeptidase nucleic acid molecule and/or a filariid cysteine protease nucleic acid molecule, examples of which are disclosed herein) inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of parasite, including D. immitis, nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell.

Preferred nucleic acid molecules to include in recombinant vectors of the present invention include at least one of the following: a nucleic acid molecule that includes at least a portion of $nDiMPA1_{1299}$, a nucleic acid molecule that includes at least a portion of $nDiMPA2_{2126}$, a nucleic acid molecule that includes at least a portion of L3 $nDiMPA3_{2292}$, a nucleic acid molecule that includes at least a portion of L3 $nDiMPA3_{2076}$, a nucleic acid molecule that includes at least a portion of adult $nDiMPA3_{2032}$, a nucleic acid molecule that includes at least a portion of adult $nDiMPA3_{2028}$, or a nucleic acid molecule that includes at least a portion of $nDiCP_{143}$. Particularly preferred nucleic acid molecules to include in recombinant vectors of the present invention include $nDiMPA1_{689}$, $nDiMPA1_{1299}$, $nDiMPA2_{2126}$, $nDiMPA2_{804}$, $nDiMPA2_{271}$, L3 $nDiMPA3_{2292}$, L3 $nDiMPA3_{2076}$, adult $nDiMPA3_{2032}$, adult $nDiMPA3_{2028}$, BvMPA2 $nDiCP_{143}$ and $nDiCPl_{142}$.

Isolated proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell that is capable of expressing the protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. A preferred nucleic acid molecule with which to transform a cell is a nucleic acid molecule that includes a parasite astacin metalloendopeptidase nucleic acid molecule and/or a filariid cysteine protease nucleic acid molecule of the present invention. Particularly preferred nucleic acid molecules with which to transform cells include nDiMPA1$_{689}$ (characterized by a coding strand having the nucleic acid sequence of SEQ ID NO:20), nDiMPA1$_{1299}$ (characterized by a coding strand having the nucleic acid sequence of SEQ ID NO:1), nDiMPA2$_{2126}$ (characterized by a coding strand having the nucleic acid sequence of SEQ ID NO:2), nDiMPA2$_{804}$ (characterized by a coding strand having the nucleic acid sequence of SEQ ID NO:21), nDiMPA2$_{271}$ (characterized by a coding strand having the nucleic acid sequence of SEQ ID NO:22), L3 nDiMPA3$_{2292}$ (characterized by a coding strand having the nucleic acid sequence of SEQ ID NO:29), L3 nDiMPA$_{2076}$ (characterized by a coding strand having the nucleic acid sequence of SEQ ID NO:30), adult nDiMPA3$_{2032}$ (characterized by a coding strand having the nucleic acid sequence SEQ ID NO:32), adult nDiMPA3$_{2028}$ (characterized by a coding strand having the nucleic acid sequence SEQ ID NO:33), BvMPA2, nDiCP$_{143}$ (characterized by a coding strand having the nucleic acid sequence of SEQ ID NO:12) and nDiCP$_{142}$ (characterized by a coding strand having the nucleic acid sequence of SEQ ID NO:23).

Suitable host cells to transform include any cell that can be transformed. Host cells can be either untransformed cells or cells that are already transformed with at least one nucleic acid molecule. Host cells of the present invention either can be endogenously (i.e., naturally) capable of producing parasite, including *D. immitis*, proteins of the present invention or can be capable of producing such proteins after being transformed with at least one nucleic acid molecule of the present invention. Host cells of the present invention can be any cell capable of producing at least one protein of the present invention, including bacterial, fungal (including yeast), animal parasite (including helminth, protozoa and ectoparasite), insect, animal and plant cells. Preferred host cells include bacterial, mycobacterial, yeast, helminth, insect and mammalian cells. More preferred host cells include Salmonella, Escherichia, Bacillus, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation) and COS cells. Particularly preferred host cells are *Escherichia coli*, including *E. coli* K-12 derivatives; *Salmonella typhi*; *Salmonella typhimurium*, including attenuated strains such as UK-1 $_x$3987 and SR-11 $_x$4072; *Spodoptera frugiperda*; *Trichoplusia ni*; BHK cells; MDCK cells; CRFK cells and non-tumorigenic mouse myoblast G8 cells (e.g., ATCC CRL 1246). Additional appropriate mammalian cell hosts include other kidney cell lines (e.g., CV-1 monkey kidney cell lines), other fibroblast cell lines (e.g., human, murine or chicken embryo fibroblast cell lines), myeloma cell lines, Chinese hamster ovary cells and/or HeLa cells.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, animal parasite, insect, animal, and plant cells. Preferred expression vectors of the present invention can direct gene expression in bacterial, yeast, helminth or other parasite, insect and mammalian cells and more preferably in the cell types heretofore disclosed.

Expression vectors of the present invention may also (a) contain secretory signals (i.e., signal segment nucleic acid sequences) to enable an expressed protein of the present invention (i.e., a parasite astacin metalloendopeptidase protein and/or a filariid cysteine protease protein) to be secreted from the cell that produces the protein and/or (b) contain fusion sequences which lead to the expression of inserted nucleic acid molecules of the present invention as fusion proteins. Eukaryotic recombinant molecules may include intervening and/or untranslated sequences surrounding and/ or within the nucleic acid sequences of nucleic acid molecules of the present invention. Examples of suitable fusion segments encoded by fusion segment nucleic acids have been disclosed. Suitable signal segments include natural signal segments (e.g., a parasite astacin metalloendopeptidase or cysteine protease signal segment) or any heterologous signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments.

Nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other parasite, insect and mammalian cells, such as, but not limited to, tac, lac, trp, trc, oxy-pro, omp/lpp, rrnB, bacteriophage lambda ($\lambda$) (such as $\lambda p_L$ and $\lambda p_R$ and fusions that include such promoters), bacteriophage T7, T71ac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, *Heliothis zea* insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a parasitic helminth, such as a *D. immitis*, molecule prior to isolation.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. Particularly preferred recombinant molecules include pβgal-nDiMPA1$_{1299}$, pβgal-nDiMPA2$_{2126}$, ptrcHis-nDiMPA2$_{804}$, pλP$_R$His-nDiMPA2$_{804}$, pBBIII-nDiMPA2$_{2126}$, pβgal-L3-nDiMPA3$_{2292}$, pβgal-L3-nDiMPA3$_{2076}$, pβgal-adult-nDiMPA3$_{2032}$, pβgal-adult-nDiMPA3$_{2028}$ and ptrcHis-nDiCP$_{142}$. Details regarding the production of such recombinant molecules is disclosed herein.

A recombinant cell of the present invention includes any cell transformed with at least one of any nucleic acid molecule of the present invention. A preferred recombinant cell is a cell transformed with a nucleic acid molecule that includes at least a portion of a parasite astacin metalloendopeptidase nucleic acid molecule, such as nDiMPA1$_{689}$, nDiMPA1$_{1299}$, nDiMPA2$_{2126}$, nDiMPA2$_{804}$, nDiMPA2$_{271}$, L3 nDiMPA3$_{2292}$, L3 nDiMPA3$_{2076}$, adult nDiMPA3$_{2032}$, adult nDiMPA3$_{2028}$, or BvMPA2 and/or at least a portion of a filariid cysteine protease nucleic acid molecule, such as a nucleic acid molecule including nDiCP$_{143}$ or nDiCP$_{142}$. Particularly preferred recombinant cells include *E. coli*:pβgal-nDiMPA1$_{1299}$, *E. coli*:pβgal-nDiMPA2$_{21261}$, *E. coli*:ptrcHis-nDiMPA2$_{804}$, *E. coli*:pλP$_R$His-nDiMPA2$_{804}$, *S. frugiperda*:pBBIII-nDiMPA2$_{2126}$, *E. coli*:pβgal-L3-nDiMPA3$_{2292}$, *E. coli*:pβgal-L3-nDiMPA3$_{2076}$, *E. coli*:pβgal-adult-nDiMPA3$_{2032}$ *E. coli*:pβgal-adult-nDiMPA3$_{2028}$, and *E. coli*: ptrcHis-nDiCP$_{142}$. Details regarding the production of these recombinant cells is disclosed herein.

Recombinant cells of the present invention can also be co-transformed with one or more recombinant molecules including nucleic acid molecules encoding one or more proteins of the present invention (e.g., parasite astacin metalloendopeptidase proteins and/or filariid cysteine protease proteins) and one or more other proteins useful in the production of multivalent vaccines which can include one or more protective compounds.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

In accordance with the present invention, recombinant cells of the present invention can be used to produce one or more proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate medium refers to any medium in which a cell of the present invention, when cultured, is capable of producing a parasite protein, including a *D. immitis* protein, of the present invention. An effective medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein" refers simply to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A vaccine for animals, for example, should exhibit no substantial toxicity and should be capable of stimulating the production of antibodies in a vaccinated animal.

The present invention also includes isolated antibodies capable of selectively binding to a protein of the present invention or to a mimetope thereof. Antibodies capable of selectively binding to a parasite astacin metalloendopeptidase protein of the present invention are referred to as anti-parasite astacin metalloendopeptidase antibodies. A particularly preferred antibody of this embodiment is an anti-$D.$ $immitis$ astacin metalloendopeptidase antibody. Antibodies capable of selectively binding to a filariid cysteine protease protein of the present invention are referred to as anti-filariid cysteine protease antibodies. A particularly preferred antibody of this embodiment is an anti-$D.$ $immitis$ cysteine protease antibody. Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees. As used herein, the term "selectively binds to" refers to the ability of such antibodies to preferentially bind to specified proteins and mimetopes thereof of the present invention. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Preferred antibodies are raised in response to proteins, or mimetopes thereof, that are encoded, at least in part, by a nucleic acid molecule of the present invention.

A preferred method to produce antibodies of the present invention includes (a) administering to an animal an effective amount of a protein or mimetope thereof of the present invention to produce the antibodies and (b) recovering the antibodies. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as vaccines to passively immunize an animal in order to protect the animal from parasites susceptible to treatment by such antibodies, (b) as reagents in assays to detect infection by such parasites and/or (c) as tools to recover desired proteins of the present invention from a mixture of proteins and other contaminants.

Furthermore, antibodies of the present invention can be used to target cytotoxic agents to parasites of the present invention in order to directly kill such parasites. Targeting can be accomplished by conjugating (i.e., stably joining) such antibodies to the cytotoxic agents using techniques known to those skilled in the art. Suitable cytotoxic agents include, but are not limited to: double-chain toxins (i.e., toxins having A and B chains), such as diphtheria toxin, ricin toxin, Pseudomonas exotoxin, modeccin toxin, abrin toxin, and shiga toxin; single-chain toxins, such as pokeweed antiviral protein, α-amanitin, and ribosome inhibiting proteins; and chemical toxins, such as melphalan, methotrexate, nitrogen mustard, doxorubicin and daunomycin. Preferred double-chain toxins are modified to include the toxic domain and translocation domain of the toxin but lack the toxin's intrinsic cell binding domain.

One embodiment of the present invention is a therapeutic composition that, when administered to an animal in an effective manner, is capable of protecting that animal from disease caused by a parasite that is susceptible to at least one of the following treatments: immunization with an isolated parasite astacin metalloendopeptidase of the present invention, immunization with an isolated filariid cysteine protease of the present invention, administration of an inhibitor of astacin metalloendopeptidase activity or administration of an inhibitor of cysteine protease activity. As used herein, a parasite that is susceptible to such a treatment is a parasite that, if such treatment is administered to an animal in an effective manner, shows substantially reduced ability to cause disease in the animal. It is to be understood that such parasite can be susceptible to treatments other than just those listed immediately above. Such treatments can include, but are not limited to, additional treatments, or therapeutic compositions, disclosed herein.

Therapeutic compositions of the present invention include at least one of the following protective compounds: (a) an isolated parasite astacin metalloendopeptidase protein or a mimetope thereof; (b) an isolated parasite nucleic acid molecule capable of hybridizing under stringent conditions with a $D.$ $immitis$ astacin metalloendopeptidase gene; (c) an anti-parasite astacin metalloendopeptidase antibody; (d) an inhibitor of astacin metalloendopeptidase activity identified by its ability to inhibit parasite astacin metalloendopeptidase activity; (e) an isolated filariid nematode cysteine protease protein or a mimetope thereof; (f) an isolated filariid nematode nucleic acid molecule capable of hybridizing under stringent conditions with a $D.$ $immitis$ cysteine protease gene; (g) an anti-filariid nematode cysteine protease antibody; and (h) an inhibitor of cysteine protease activity identified by its ability to inhibit filariid nematode cysteine protease activity. As used herein, a protective compound refers to a compound that, when administered to an animal in an effective manner, is able to treat, ameliorate, and/or prevent disease caused by a parasite of the present invention. Preferred parasites to target are heretofore disclosed. Examples of proteins, nucleic acid molecules and antibodies of the present invention are disclosed herein. Astacin metalloendopeptidase inhibitors and cysteine protease inhibitors of the present invention are described in more detail below.

The present invention also includes a therapeutic composition comprising at least one astacin parasite metalloendopeptidase-based or filariid nematode cysteine protease-based protective compound of the present invention in combination with at least one additional compound protective against one or more infectious agents. Examples of such compounds and infectious agents are heretofore disclosed.

Therapeutic compositions of the present invention can be administered to any animal susceptible to such therapy, preferably to mammals, and more preferably to dogs, cats, humans, ferrets, horses, cattle, sheep and other pets and/or economic food animals. Preferred animals to protect include dogs, cats, humans and ferrets, with dogs and cats being particularly preferred.

In one embodiment, a therapeutic composition of the present invention can be administered to the vector in which the parasite develops from a microfilaria into L3, such as to a mosquito in order to prevent the spread of heartworm. Such administration could be orally or by developing transgenic vectors capable of producing at least one therapeutic composition of the present invention. In another embodiment, a vector, such as a mosquito, can ingest therapeutic compositions present in the blood of a host that has been administered a therapeutic composition of the present invention.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the therapeutic composition can also include an immunopotentiator, such as an adjuvant or a carrier. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

In order to protect an animal from disease caused by a parasite of the present invention, a therapeutic composition of the present invention is administered to the animal in an effective manner such that the composition is capable of protecting that animal from a disease caused by a parasite. For example, an isolated protein or mimetope thereof, when administered to an animal in an effective manner, is able to elicit (i.e., stimulate) an immune response, preferably including both a humoral and cellular response, that is sufficient to protect the animal from the disease. Similarly, an antibody of the present invention, when administered to an animal in an effective manner, is administered in an amount so as to be present in the animal at a titer that is sufficient to protect the animal from the disease, at least temporarily. Oligonucleotide nucleic acid molecules of the present invention can also be administered in an effective manner, thereby reducing expression of astacin metalloendopeptidase or cysteine protease proteins in order to interfere with development of parasites targeted in accordance with the present invention.

Therapeutic compositions of the present invention can be administered to animals prior to infection in order to prevent infection and/or can be administered to animals after infection in order to treat disease caused by the parasite. For example, proteins, mimetopes thereof, and antibodies thereof can be used as immunotherapeutic agents. Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster vaccinations preferably are administered when the immune response of the animal becomes insufficient to protect the animal from disease. A preferred administration schedule is one in which from about 10 $\mu$g to about 1 mg of the vaccine per kg body weight of the animal is administered from about one to about two times over a time period of from about 2 weeks to about 12 months. Modes of administration can include, but are not limited to, subcutaneous, intradermal, intravenous, nasal, oral, transdermal and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme or RNA drug) in the animal to be protected from disease. Nucleic acid molecules can be delivered to an animal in a variety of methods including, but not limited to, (a) direct injection (e.g., as "naked" DNA or RNA molecules, such as is taught, for example in Wolff et al., 1990, *Science* 247, 1465–1468) or (b) packaged as a recombinant virus particle vaccine or as a recombinant cell vaccine (i.e., delivered to a cell by a vehicle selected from the group consisting of a recombinant virus particle vaccine and a recombinant cell vaccine).

A recombinant virus particle vaccine of the present invention includes a recombinant molecule of the present invention that is packaged in a viral coat and that can be expressed in an animal after administration. Preferably, the recombinant molecule is packaging-deficient. A number of recombinant virus particles can be used, including, but not limited to, those based on alphaviruses, poxviruses, adenoviruses, herpesviruses, and retroviruses. Preferred recombinant particle viruses are those based on alphaviruses (such as Sindbis virus), herpesviruses and poxviruses. Methods to produce and use recombinant virus particle vaccines are disclosed in U.S. patent application Ser. No. 08/015,414, filed Feb. 8, 1993, entitled "Recombinant Virus Particle Vaccines", which is incorporated by reference herein in its entirety.

When administered to an animal, a recombinant virus particle vaccine of the present invention infects cells within the immunized animal and directs the production of a protective protein or RNA nucleic acid molecule that is capable of protecting the animal from disease caused by a parasite of the present invention. For example, a recombinant virus particle comprising a *D. immitis* astacin metalloendopeptidase nucleic acid molecule and/or a *D. immitis* cysteine protease nucleic acid molecule of the present invention is administered according to a protocol that results in the animal producing a sufficient immune response to protect itself from heartworm. A preferred single dose of a recombinant virus particle vaccine of the present invention is from about $1\times10^4$ to about $1\times10^7$ virus plaque forming units (pfu) per kilogram body weight of the animal. Administration protocols are similar to those described herein for protein-based vaccines.

A recombinant cell vaccine of the present invention includes recombinant cells of the present invention that express at least one protein of the present invention. Preferred recombinant cells include Salmonella, *E. coli*, Mycobacterium, *S. frugiperda*, baby hamster kidney, myoblast G8, COS, MDCK and CRFK recombinant cells, with Salmonella recombinant cells being more preferred. Such recombinant cells can be administered in a variety of ways but have the advantage that they can be administered orally, preferably at doses ranging from about $10^8$ to about $10^{12}$ bacteria per kilogram body weight. Administration protocols are similar to those described herein for protein-based vaccines. Recombinant cell vaccines can comprise whole cells or cell lysates.

In common with most other enteric pathogens, Salmonella strains normally enter the host orally. Once in the intestine, they interact with the mucosal surface, normally to establish an invasive infection. Most Salmonella infections are controlled at the epithelial surface, causing the typical Salmonella-induced gastroenteritis. Some strains of Salmonella, including *S. typhi* and some *S. typhimurium* isolates, have evolved the ability to penetrate deeper into the host, causing a disseminated systemic infection. It appears such strains have the capacity to resist the killing actions of macrophages and other immune cells. *S. typhi* can exist for long periods as a facultative intracellular parasite. Some of the live vaccine strains can also persist for long periods in the mononuclear phagocyte system. Hosts infected in such a manner develop, in addition to a mucosal immune response, systemic cellular and serum antibody responses to the Salmonella. Thus, invading Salmonella, whether virulent or attenuated, can stimulate strong immune responses, unlike many other enteric pathogens which only set up local, noninvasive gut infections. The potent immunogenicity of live Salmonella makes them attractive candidates for carrying nucleic acid molecules of the present invention, and the proteins they encode, to the immune system.

A preferred recombinant cell-based vaccine is one in which the cell is attenuated. *Salmonella typhimurium* strains, for example, can be attenuated by introducing mutations into genes critical for in vivo growth and survival. For example, genes encoding cyclic adenosine monophosphate (cAMP) receptor protein or adenylate cyclase are deleted to produce avirulent, vaccine strains. Such strains can deliver antigens to lymphoid tissue in the gut but demonstrate reduced capacity to invade the spleen and mesenteric lymph nodes. These strains are still capable of stimulating both humoral and cellular immunity in mammalian hosts.

Recombinant cell vaccines can be used to introduce proteins of the present invention into the immune systems of animals. For example, recombinant molecules comprising nucleic acid molecules of the present invention operatively linked to expression vectors that function in Salmonella can be transformed into Salmonella host cells. The resultant recombinant cells are then introduced into the animal to be protected. Preferred Salmonella host cells are those for which survival depends on their ability to maintain the recombinant molecule (i.e., a balanced-lethal host-vector system). An example of such a preferred host recombinant molecule combination is a Salmonella strain (e.g., UK-1 $\chi$3987 or SR-11 $\chi$4072) which is unable to produce aspartate β-semialdehyde dehydrogenase in combination with a recombinant molecule also capable of encoding the enzyme. Aspartate β-semialdehyde dehydrogenase, encoded by the asd gene, is an important enzyme in the pathway to produce diaminopimelic acid (DAP). DAP is an essential component of the peptidoglycan of the cell wall of Gram-negative bacteria, such as Salmonella, and, as such, is necessary for survival of the cell. Thus, Salmonella lacking a functional asd gene can only survive if they maintain a recombinant molecule that is also capable of expressing a functional asd gene.

In one embodiment, a nucleic acid molecule of the present invention is inserted into expression vector pTECH-1 (available from Medeva, London, U.K.) and the resulting recombinant molecule is transfected into a Salmonella strain, such as BRD 509 (available from Medeva), to form a recombinant cell. Such recombinant cells can be used to produce the corresponding encoded protein or can be used as recombinant cell vaccines.

One preferred embodiment of the present invention is the use of nucleic acid molecules and proteins of the present invention, and particularly *D. immitis* nucleic acid molecules and proteins of the present invention, to protect an animal from heartworm. Preferred therapeutic compositions are those that are able to inhibit at least one step in the portion of the parasite's development cycle that includes L3 larvae, third molt, L4 larvae, fourth molt and immature adult prior to entering the circulatory system. In dogs, this portion of the development cycle is about 70 days. As such, preferred therapeutic compositions include *D. immitis* astacin metalloendopeptidase-based and *D. immitis* cysteine protease-based therapeutic compounds of the present invention. Such compositions are administered to animals in a manner effective to protect the animals from heartworm. Additional protection may be obtained by administering additional protective compounds, including other *D. immitis* proteins, nucleic acid molecules and antibodies as heretofore disclosed.

One embodiment of the present invention is the use of enzymatically active parasite astacin metalloendopeptidase and/or filariid nematode cysteine protease proteins of the present invention to identify inhibitors of such enzyme activity. While not being bound by theory, it is believed that parasites use such proteases in a number of ways, including, but not limited to, to effect embryonic and larval development, to effect molting and to effect tissue migration both as larvae and adults. Such proteases are capable of degrading cutaneous connective tissue macromolecules as well as other proteinaceous material to facilitate such functions. It is also of interest that astacin metalloendopeptidases identified in sea urchins, Drosophila and Xenopus have been linked with development and maturation of the respectively organisms. As such, inhibitors of astacin metalloendopeptidase and/or cysteine protease activity could be particularly beneficial in disrupting embryonic and/or larval development or molting by parasites in general and tissue migration by those parasites capable of such migration. Use of parasite enzymes to develop such inhibitors is also advantageous because inhibitors can be identified that are highly selective for the parasite without causing undue side effects to the animal being treated.

One therapeutic composition of the present invention includes an inhibitor of parasite astacin metalloendopeptidase activity, i.e., a compound capable of substantially interfering with the function of a parasite astacin metalloendopeptidase susceptible to inhibition by an inhibitor of *D. immitis* astacin metalloendopeptidase activity. An inhibitor of astacin metalloendopeptidase can be identified using enzymatically active parasite and preferably *D. immitis*, astacin metalloendopeptidase proteins of the present invention.

One embodiment of the present invention is a method to identify a compound capable of inhibiting astacin metalloendopeptidase activity of a parasite. Such a method includes the steps of (a) contacting (e.g., combining, mixing) an isolated parasite, preferably *D. immitis*, astacin metalloendopeptidase protein with a putative inhibitory compound under conditions in which, in the absence of the compound, the protein has astacin metalloendopeptidase activity, and (b) determining if the putative inhibitory compound inhibits the astacin metalloendopeptidase activity. Putative inhibitory compounds to screen include organic molecules, antibodies (including functional equivalents thereof) and substrate analogs. Methods to determine astacin metalloendopeptidase activity are known to those skilled in the art; see, for example, Gomis-Ruth, et al. ibid., and referenced cited therein.

The present invention also includes a test kit to identify a compound capable of inhibiting astacin metalloendopeptidase activity of a parasite. Such a test kit includes an isolated parasite, preferably *D. immitis*, astacin metalloendopeptidase protein having astacin metalloendopeptidase activity and a means for determining the extent of inhibition of astacin metalloendopeptidase activity in the presence of (i.e., effected by) a putative inhibitory compound.

Astacin metalloendopeptidase inhibitors isolated by such a method, and/or test kit, can be used to inhibit any astacin metalloendopeptidase that is susceptible to such an inhibitor. Preferred astacin metalloendopeptidase enzymes to inhibit are those produced by parasites. A particularly preferred astacin metalloendopeptidase inhibitor of the present invention is capable of protecting an animal from heartworm. It is also within the scope of the present invention to use inhibitors of the present invention to target astacin metalloendopeptidase-related disorders in animals. Therapeutic compositions comprising astacin metalloendopeptidase inhibitory compounds of the present invention can be administered to animals in an effective manner to protect animals from disease caused by the targeted astacin metalloendopeptidase enzymes, and preferably to protect animals from heartworm. Effective amounts and dosing regimens can be determined using techniques known to those skilled in the art.

Another therapeutic composition of the present invention includes an inhibitor of parasite cysteine protease activity, i.e., a compound capable of substantially interfering with the function of a parasite cysteine protease susceptible to inhibition by an inhibitor of filariid nematode cysteine protease activity. A cysteine protease inhibitor can be identified using enzymatically active filariid nematode, and preferably *D. immitis*, cysteine protease proteins of the present invention.

One embodiment of the present invention is a method to identify a compound capable of inhibiting cysteine protease activity of a parasite. Such a method includes the steps of (a) contacting (e.g., combining, mixing) an isolated filariid nematode, preferably *D. immitis*, cysteine protease protein with a putative inhibitory compound under conditions in which, in the absence of the compound, the protein has cysteine protease activity, and (b) determining if the putative inhibitory compound inhibits the cysteine protease activity. Putative inhibitory compounds to screen include organic molecules, antibodies (including functional equivalents thereof) and substrate analogs. Methods to determine cysteine protease activity are known to those skilled in the art, as heretofore disclosed.

The present invention also includes a test kit to identify a compound capable of inhibiting cysteine protease activity of a parasite. Such a test kit includes an isolated filariid nematode, preferably *D. immitis*, cysteine protease protein having cysteine protease activity and a means for determining the extent of inhibition of cysteine protease activity in the presence of (i.e., effected by) a putative inhibitory compound.

Inhibitors isolated by such a method, and/or test kit, can be used to inhibit any cysteine protease that is susceptible to such an inhibitor. Preferred cysteine protease enzymes to inhibit are those produced by parasites. A particularly preferred cysteine protease inhibitor of the present invention is capable of protecting an animal from heartworm. It is also within the scope of the present invention to use inhibitors of the present invention to target cysteine protease-related disorders in animals. Therapeutic compositions comprising cysteine protease-inhibitory compounds of the present invention can be administered to animals in an effective manner to protect animals from disease caused by the targeted cysteine protease. Effective amounts and dosing regimens can be determined using techniques known to those skilled in the art.

The efficacy of a therapeutic composition of the present invention to protect an animal from disease caused by a parasite can be tested in a variety of ways including, but not limited to, detection of protective antibodies (using, for example, proteins or mimetopes of the present invention), detection of cellular immunity within the treated animal, or challenge of the treated animal with the parasite to determine whether the treated animal is resistant to disease. Such techniques are known to those skilled in the art.

In accordance with the present invention, the inventors have shown that protease inhibitors can inhibit parasite larval development. For example, bestatin and phosphoramidon have been shown to inhibit molting of *D. immitis* larvae, as described in more detail in the Examples.

Another embodiment of the present invention includes the isolation of proteases, including metalloproteases and cysteine proteases from parasitic larval excretory/secretory (ES) products. Using a modified version of the protocol first described in U.S. patent application Ser. No. 08/153,554, ibid., the inventors have, for example, isolated a fraction comprising a protein of approximately 60 kD (as determined by Tris-glycine sodium dodecyl sulfate polyacrylamide gel electrophoresis (SDS-PAGE) that has metalloprotease activity as determined by the protein's ability to cleave H-Phe-AMC. When submitted to size-exclusion chromatography, the active fraction elutes with bovine serum albumin, indicating an approximate molecular weight of from about 62 to about 66 kD. The modified protocol, which is described in more detail in the Examples, includes submitting parasitic, preferably *D. immitis,* larval ES, to anion exchange chromatography, followed by size exclusion chromatography and isoelectric focussing. The active fraction has a pI of about 6.8.

In another embodiment, the inventors have identified at least one parasite metalloprotease from the ES that is capable of degrading collagen. For example, electrophoresis of *D. immitis* larval ES through a gelatin-based matrix leads to isolated active fractions that migrate with apparent molecular weights of about 60, 95 and at least about 200 kD. The proteolytic activity of such fractions is essentially completely inhibited by EDTA.

It is also within the scope of the present invention to use isolated proteins, mimetopes, nucleic acid molecules and antibodies of the present invention as diagnostic reagents to detect infection by parasites. Such diagnostic reagents can be supplemented with additional compounds that can detect other phases of the parasite's life cycle.

The following examples are provided for the purposes of illustration and are not intended to limit the scope of the present invention.

EXAMPLES

The following examples include a number of recombinant DNA and protein chemistry techniques which are known to those skilled in the art; see, for example, Sambrook et al., ibid.

Example 1

This Example discloses the cloning and sequencing of two parasite astacin metalloendopeptidase nucleic acid molecules of the present invention. This Example also discloses the production of a recombinant molecule and recombinant cell of the present invention.

A *D. immitis* third stage larvae cDNA expression library was prepared in the following manner. Total RNA was extracted from *D.immitis* third stage larvae (L3) using an acid-guanidinium-phenol-chloroform method similar to that described by Chomczynski and Sacchi, 1987, *Anal. Biochem.* 162, p. 156–159. Approximately 230,000 L3 were used in the RNA preparation. Poly A+ selected RNA was separated from total RNA by oligo-dT cellulose chromatography using Oligo dT cellulose from Collaborative Research Inc., Waltham, Mass., according to the method recommended by the manufacturer.

The expression library was constructed by inserting the L3 poly A+ RNA into the expression vector lambda ($\lambda$) Uni-ZAP™ XR (available from Stratagene Cloning Systems, La Jolla, Calif.) using Stratagene's ZAP-CDNA Synthesis Kit® protocol and about 6–7 µg of L3 poly A+ RNA. The resultant library was amplified to a titer of about $4.88 \times 10^9$ pfu/ml with about 96% recombinants. Ten minilibraries were generated by one further round of amplification of randomly selected aliquots of the original L3 cDNA amplified library. These minilibrary phage were collected in phage dilution buffer (e.g., 10 mM Tris-HCl, pH 7.5, 10 mM magnesium sulfate) and stored at 4° C.

A *D. immitis* astacin metalloendopeptidase nucleic acid molecule of about 689 nucleotides, representing a partial *D. immitis* astacin metalloendopeptidase gene and denoted nDiMPA1$_{689}$, was PCR amplified from *D. immitis* L3 cDNA expression minilibraries using the following two primers: a 4-fold degenerate primer having SEQ ID NO:14, namely 5' ACWCATGAAATIGSICAT 3' (denoted MP1; W can be A or T; S can be C or G; I is inosine) and an antisense oligonucleotide having SEQ ID NO:15, namely 5' AATACGACTCACTATAG 3' (denoted T7). Primer MP1 was designed from published sequences of the metalloprotease conserved zinc binding domain. Primer T7 is complementary to the pBluescript® vector (available from Stratagene).

A nucleic acid molecule amplified from minilibrary number 10, which was denoted nDiMPA1$_{689}$, was gel-purified, electroeluted and cloned into the cloning vector pCRII (available from Invitrogen, San Diego, Calif.) following manufacturer's instructions, thereby forming recombinant vector pCRII-nDiMPA1$_{689}$. The nucleotide sequence of nDiMPA1$_{689}$ (characterized by a coding strand having the nucleic acid sequence of SEQ ID NO:20) was determined and found to include nucleotides spanning from about nucleotide position 610 through the 3' end of SEQ ID NO:1, the production of which is described in more detail below.

The L3 cDNA minilibrary number 10 was screened with the radiolabeled MP1 oligonucleotide as a probe, using stringent (i.e., standard) hybridization conditions as described in Sambrook et al., ibid. Plaques which hybridized to the probe were rescreened and plaque-purified. The plaque-purified clone including *D. immitis* nucleic acid molecule nDiMPA1$_{1299}$ was converted into a double stranded recombinant molecule, herein denoted as p$\beta$gal-nDiMPA1$_{1299}$, using R408 helper phage and XL1-Blue *E. coli* according to the in vivo excision protocol described in the Stratagene ZAP-cDNA Synthesis Kit®. Double-stranded plasmid DNA was prepared using an alkaline lysis protocol, such as that described in Sambrook et al., ibid. Recombinant molecule p$\beta$gal-nDiMPA1$_{1299}$ was transformed into *E. coli* to form recombinant cell *E. coli*:p$\beta$gal-nDiMPA1$_{1299}$.

Recombinant molecule p$\beta$gal-nDiMPA1$_{1299}$ was submitted to nucleic acid sequencing using the Sanger dideoxy chain termination method, as described in Sambrook et al., ibid. An about 1299 nucleotide consensus sequence of nucleic acid molecule nDiMPA1$_{1299}$ was determined and is presented as SEQ ID NO:1. SEQ ID NO:1 apparently encodes three overlapping open reading frames. The first open reading frame, denoted PDiMPA1$_{ORF1}$, is about 191 amino acids (presented in SEQ ID NO:3) and encompasses about nucleotide number 18–590 of SEQ ID NO:1. The second open reading frame, denoted PDiMPA1$_{ORF2}$, is about 141 amino acids (presented in SEQ ID NO:4) and encompasses about nucleotide number 508–930 of SEQ ID:1. Open reading frame PDiMPA1$_{ORF2}$ includes the extended zinc binding domain and hydrophilic region HEIGHTLGIFHE beginning at about amino acid 36 of SEQ ID NO:4, as well as the domain YDTGSVMHY (beginning at about amino acid position 87) that includes the tyrosine that is thought to bind to zinc at about amino acid position 95. The third open reading frame, denoted PDiMPA1$_{ORF3}$, is about 121 amino acids (presented in SEQ ID NO: 5) and encompasses nucleotide number 785–1147 of SEQ ID:1.

A homology search of the non-redundant protein sequence database was performed through the National Center for Biotechnology Information using the BLAST network. This database includes +SwissProt+PIR+SPUpdate+GenPept+GPUpdate. The search, which was performed using SEQ ID NO:3, SEQ ID NO:4 and SEQ ID NO:5, showed significant homology at the amino acid level by all three open reading frames to members of the astacin family of metalloendopeptidases. Significant homology throughout all three amino acid open reading frames is also associated with a *C. elegans* R151.5 gene product, Genbank accession number U00036.

It was apparent from the pBluescript vector sequences at and near the 5' end of nucleic acid molecule nDiMPA1$_{1299}$ that two cDNA fragments had ligated to each other via their 5' ends to form that nucleic acid molecule. A comparison of the nucleotide sequence of SEQ ID NO:1 to that of SEQ ID NO:2 (the apparent nucleotide sequence of independently-isolated astacin metalloendopeptidase nucleic acid molecule nDiMPA2$_{2126}$ described in Example 2) as well as to nucleotide sequences of other members the astacin family of metalloendopeptidases, showed that nucleotide number 56 of SEQ ID NO:1 corresponds to the first nucleotide on the 5' end of nDiMPA2$_{2126}$ suggesting that nucleotide number 56 represents the junction of the two different cDNA sequences in nDiMPA1$_{1299}$. Therefore, nucleotides 1 through 55 of nDiMPA1$_{1299}$ most likely represent a non-astacin related cDNA sequence which ligated to the 5' end of the astacin metalloendopeptidase cDNA fragment prior to cloning. Astacin homology at the amino acid level can be found starting with amino acid number 125 of the first open reading frame of nDiMPA1$_{1299}$, namely PDiMPA1$_{ORF1}$.

Example 2

This Example discloses the cloning and sequencing of an additional parasite astacin metalloendopeptidase nucleic acid molecule of the present invention. This Example also discloses the production of a recombinant molecule and recombinant cell of the present invention.

Due to the unusual sequences on the 5' end of astacin metalloendopeptidase nucleic acid molecule nDiMPA1$_{1299}$, a second astacin metalloendopeptidase nucleic acid molecule, denoted nDiMPA2$_{2126}$, was isolated from the L3 cDNA expression library described in Example 1, as follows.

A D. immitis astacin metalloendopeptidase nucleic acid molecule of about 271 nucleotides, denoted nDiMPA2$_{271}$ (characterized by a coding strand having the nucleic acid sequence of SEQ ID NO:22), was PCR amplified from D. immitis L3 cDNA expression minilibrary number 9 using the following two primers: an oligonucleotide having SEQ ID NO:16, namely 5¹′ TGGTATTATATCACATGAAATTGGT-CATAC 3′ (denoted ZNSEN) and an antisense oligonucleotide having SEQ ID NO:17, namely 5′ CCCCATTGTG-TACTGTTGAAATTTATCAC 3′ (denoted MP14). Primer ZNSEN was designed from the nucleotide sequence encoding the metalloprotease conserved zinc binding domain in nDiMPA1$_{1299}$ and spans from about nucleotide 600 through about nucleotide 629 of SEQ ID NO:1. Primer MP14 is an antisense primer complementary to a region spanning from about nucleotide 842 through about nucleotide 870 of nDiMPA1$_{1299}$.

Nucleic acid molecule nDiMPA2$_{271}$ was radiolabeled and used as a probe to screen L3 cDNA minilibrary number 9. Plaques which hybridized under stringent hybridization conditions to the probe were rescreened and plaque purified. A plaque-purified clone including D. immitis nucleic acid molecule nDiMPA2$_{2126}$, was converted into a double-stranded recombinant molecule, herein denoted as pβgal-nDiMPA2$_{2126}$, using R408 helper phage and XL1-Blue E. coli according to the in vivo excision protocol described in the Stratagene ZAP-cDNA Synthesis Kit®. Double-stranded plasmid DNA was prepared using an alkaline lysis protocol, such as that described in Sambrook et al., ibid. Recombinant molecule pβgal-nDiMPA2$_{2126}$ was transformed into E. coli to form recombinant cell E. coli:pβgal-nDiMPA2$_{2126}$.

Recombinant molecule pβgal-nDiMPA2$_{2126}$ was submitted to nucleic acid sequencing using the Sanger dideoxy chain termination method, as described in Sambrook et al., ibid. An about 2126-nucleotide consensus sequence of nucleic acid molecule nDiMPA2$_{2126}$ was determined and is presented as SEQ ID NO:2. SEQ ID NO:2 apparently encodes five overlapping open reading frames. The first open reading frame, denoted PDiMPA2$_{ORF1}$, is about 178 amino acids (presented in SEQ ID NO:6) and encompasses about nucleotide numbers 2–535 of SEQ ID:2. The second open reading frame, denoted PDiMPA2$_{ORF2}$, is about 145 amino acids (presented in SEQ ID NO:7) and encompasses about nucleotide numbers 453–887 of SEQ ID:2. PDiMPA2$_{ORF2}$ includes the extended zinc binding domain, beginning at about amino acid 36 of SEQ ID NO:7 as well as the tyrosine-containing motif, beginning at about amino acid 87. The third open reading frame, denoted PDiMPA2$_{ORF3}$, is about 134 amino acids (presented in SEQ ID NO:8) and encompasses nucleotide number 730–1131 of SEQ ID:2. The fourth open reading frame, denoted PDiMPA2$_{ORF4}$, is about 154 amino acids (presented in SEQ ID NO:9) and encompasses nucleotide number 1112–1573 of SEQ ID:2. The fifth open reading frame, denoted PDiMPA2$_{ORF5}$, is about 163 amino acids (presented in SEQ ID NO:10) and encompasses nucleotide number 1429–1917 of SEQ ID:2.

A comparison of the deduced nucleic acid sequences of nDiMPA1$_{1299}$ (SEQ ID NO: 1) and nDiMPA2$_{2126}$ (SEQ ID NO: 2) indicates that nDiMPA2$_{2126}$ does not contain the stretch of nucleotides from about positions 1 through 55 of nDiMPA1$_{1299}$ (as numbered in SEQ ID NO:1). As discussed above, it is believed that this stretch of nucleotides represents an unrelated cDNA clone that ligated to the 5' end of the astacin metalloendopeptidase nucleic acid molecule. The stretch of nucleotides spanning from about positions 56 through 907 of nDiMPA1$_{1299}$ (as numbered in SEQ ID NO:1) share 100% homology with the stretch of nucleotides spanning from about positions 1 through 852 of nDiMPA2$_{2126}$ (as numbered in SEQ ID NO:2). The stretch of nucleotides spanning from about positions 908 through 970 of nDiMPA1$_{1299}$ (as numbered in SEQ ID NO:1) are missing from nDiMPA2$_{2126}$. The stretch of nucleotides spanning from about positions 971 through 1133 of nDiMPA1$_{1299}$ (as numbered in SEQ ID NO:1) share 100% homology with the stretch of nucleotides spanning from about positions 853 through 1015 of nDiMPA2$_{2126}$ (as numbered in SEQ ID NO:2). Nucleic acid molecule nDiMPA2$_{2126}$ has a significantly longer 3' end than does nDiMPA1$_{1299}$.

A homology search of the non-redundant protein sequence database was performed through the National Center for Biotechnology Information using the BLAST network. This database includes +SwissProt+PIR+SPUpdate+GenPept+GPUpdate. The search, which was performed using SEQ ID NO:7, SEQ ID NO:8, SEQ ID NO:9 and SEQ ID NO:10 and SEQ ID NO:11, showed that SEQ ID NO: 7, SEQ ID NO: 8, SEQ ID NO: 9 and SEQ ID NO:10 each shared significant homology at the amino acid level with known members of the astacin family of metalloendopeptidases. SEQ ID NO:11, in contrast did not show significant homology to a known astacin metalloendopeptidase.

A composite D. immitis ORF of the five open reading frames encoded by nDiMPA2$_{2126}$ was produced by lining up the five ORFs in relation to known astacin metalloendopeptidase sequences. The composite D. immitis ORF, which spans a region significantly larger than the 200-amino acid astacin protein, is presented in SEQ ID NO:11. A comparison between the astacin domain of SEQ ID NO:11 and crayfish astacin showed about 29% homology at the amino acid level. The astacin domain of SEQ ID NO:11 also shared about 30 percent, 31 percent, 33 percent and 33 percent homology at the amino acid level with the astacin domains of, respectively, human bone morphogenetic protein 1, mouse kidney brush border metalloendopeptidase, human intestinal brush border metalloendopeptidases and Xenopus laevis embryonic protein UVS.2.

Comparison of SEQ ID NO:11 and the *C. elegans* R151.5 gene product, (Genbank accession number U00036) showed an about 24% homology between the two sequences. The *C. elegans* gene product also includes a well-conserved extended zinc binding domain motif and tyrosine-containing motif. It is interesting that although the *C. elegans* R151.5 gene product was identified by Wilson et al., ibid., as an open reading frame, the authors of that publication describing a 2.2 megabase contiguous nucleotide sequence from the free-living nematode *C. elegans* failed to appreciate the homology between R151.5 and the family of astacin metalloendopeptidases. The present inventors are apparently the first to note such a homology and the likelihood that *C. elegans* encodes an astacin metalloendopeptidase.

Example 3

This Example discloses the production of a recombinant cell of the present invention and its use to produce a parasitic astacin metalloendopeptidase protein of the present invention.

Recombinant molecule ptrcHis-nDiMPA2$_{804}$, containing nucleotides from about positions 119 through 922 of nDiMPA2$_{2126}$ (as numbered in SEQ ID NO:2, the sequence of nDiMPA2$_{804}$ characterized by a coding strand having the nucleic acid sequence of SEQ ID NO:21) operatively linked to trc transcription control sequences and to a fusion sequence encoding a poly-histidine segment comprising 6 histidines was produced in the following manner. An about 804-nucleotide DNA fragment containing nucleotides spanning from about 119 through about 922 of nDiMPA2$_{2126}$ (as numbered in SEQ ID NO:2), denoted nDiMPA2$_{804}$ was cleaved from recombinant molecule pβgal-nDiMPA2$_{2126}$, with BamHI restriction endonuclease, gel purified and subcloned into expression vector pTrcHisB (available from Invitrogen) that had been cleaved with BamHI. The resulting recombinant molecule ptrcHis-nDiMPA2$_{804}$ was transformed into *E. coli* to form recombinant cell *E. coli*:ptrcHis-nDiMPA2$_{804}$.

Recombinant cell *E. coli*:ptrcHis-nDiMPA2$_{804}$ is cultured in shake flasks containing an enriched bacterial growth medium containing about 0.1 mg/ml ampicillin at about 37° C. When the cells reach an OD$_{600}$ of about 0.3, expression of *E. coli*:ptrcHis-nDiMPA2$_{804}$ is induced by addition of about 1 mM isopropyl-β-D-thiogalactoside (IPTG), and the cells cultured for about 3 hours at about 37° C. Protein production is monitored by SDS-PAGE of recombinant cell lysates, followed by Coomassie blue staining, using standard techniques. Recombinant cell *E. coli*:ptrcHis-nDiMPA2$_{804}$ produces a fusion protein, denoted herein as PHIS-PDiMPA2$_{804}$, that is not produced by cells transformed with the pTrcHisB plasmid lacking a parasite nucleic acid molecule insert.

Example 4

This Example discloses the production of another recombinant cell of the present invention capable of producing a parasitic astacin metalloendopeptidase protein of the present invention.

Recombinant molecule pλP$_R$His-nDiMPA2$_{804}$, containing nucleotides from about positions 119 through 922 of nDiMPA2$_{2126}$ (as numbered in SEQ ID NO:2) operatively linked to λP$_R$ transcription control sequences and to a fusion sequence encoding a poly-histidine segment comprising 6 histidines was produced in the following manner. Nucleic acid molecule nDiMPA2$_{804}$, produced as described in Example 3, was ligated into the BamHI restriction site of the λP$_R$/T7/RSET-B expression vector. The vector, which is about 3455 base pairs (bp), contains an about 1990-bp pair PvuII to AatII fragment from pUC19 containing the ampicillin resistance gene and *E. coli* origin of replication; an about 1100 bp BglII to BglII DNA fragment from vector pRK248cIts (available as ATCC #33766) with a PvuII linker added to one end, containing the λP$_R$ promoter, the cI$^{857}$ λ repressor gene and 22 amino acids of the cro gene regulating lytic growth; an about 55-bp BglII to XbaI segment from pGEMEX-1 (available from Promega, Madison, Wis.) which contains the T7 promoter; an about 170-bp XbaI to EcoRI segment from pRSET-B (available from Invitrogen) which contains the T7-S10 translational enhancer, the His6 fusion, the 11 amino acid S10 leader fusion, an enterokinase cleavage site and the multiple cloning site; and an about 140-bp fragment containing synthetic translational and transcription termination signals including the T$_1$ translation terminators in all three reading frames, RNA stabilization sequence from *Bacillus thurengiensis* crystal protein and the T$_2$ rho-independent transcription terminator from the trpA operon. The resulting recombinant molecule, denoted pλP$_R$His-nDiMPA2$_{804}$, was transformed into *E. coli* to form recombinant cell *E. coli*: pλP$_R$His-nDiMPA2$_{804}$.

Example 5

This Example describes another recombinant cell of the present invention and its use to produce a parasitic astacin metalloendopeptidase protein of the present invention.

Recombinant molecule pBBIII-nDiMPA2$_{2126}$, containing nucleic acid molecule nDiMPA2$_{2126}$ (produced as described in Example 2) operatively linked to baculovirus polyhedron transcription control sequences was produced in the following manner. In order to produce a baculovirus recombinant molecule capable of directing the production of the protein encoded by nDiMPA2$_{2126}$, recombinant molecule pβgal-nDiMPA2$_{2126}$, produced as described in Example 2, was digested with XhoI, end-filled with Klenow DNA Polymerase, digested with PstI, gel purified and referred to as BvMPA2. The baculovirus shuttle plasmid, BlueBacIII (BBIII) (available from Invitrogen) was digested with NcoI, end-filled, digested with PstI and treated with calf intestinal phosphatase. The resulting vector fragment was gel purified and ligated to BvMPA2. The resultant recombinant molecule, denoted pBBIII-nDiMPA2$_{2126}$, was verified for proper insert orientation by restriction mapping. This construct and linear Baculogold baculovirus DNA (Pharmingen) were cotransfected into *Spodoptera frugiperda* Sf9 host cells (donated by Colorado Bioprocessing Center, Fort Collins, Colo.). The resulting recombinant virus termed BvMPA, was cultivated for increased production of recombinant virus and to verify expression of nDiMPA2$_{2126}$ by Western blot.

Example 6

This Example describes the cloning and sequencing of additional parasite astacin metalloendopeptidase nucleic acid molecules of the present invention. This Example also discloses the production of recombinant molecules of the present invention.

Due to the unusual overlapping reading frames within both previously isolated astacin L3 cDNA clones, an astacin metalloendopeptidase nucleic acid molecule, denoted L3 nDiMPA3$_{2292}$ was isolated from the L3 cDNA expression library described in Example 1, as follows.

A *D. immitis* astacin metalloendopeptidase nucleic acid molecule of about 341 nucleotides, denoted nDiMPA2$_{341}$ (represented by nucleotides 504 through 844 of SEQ ID NO:2) was PCR amplified from pβgal-nDiMPA2$_{2126}$ using the following two primers: an oligonucleotide having the following sequence: 5'GTCGGATCCGCAGGAGGGAATTTCAATTTCAACA-3' (denoted Astacin 1$^+$ SEQ ID NO:25) and an antisense oligonucleotide have the following sequence: 5'TCAA-GATCTAATCCAGAAATGATGGCCCTTCACG 3' (denoted Astacin 1$^-$ SEQ ID NO:26). The primers Astacin 1$^+$ and Astacin 1$^-$ were designed based on the nucleotide sequence encoding regions surrounding the conserved zinc binding domain and hydrophilic region of the molecule nDiMPA2$_{2126}$ described in Example 2 above, the consensus nucleic acid sequence of which is denoted SEQ ID NO:2. The portion of SEQ ID NO:2 encoding a zinc binding domain and hydrophilic region spans from about nucleotide 558 through about nucleotide 614. Primer astacin 1$^+$ (SEQ ID NO:25) was designed from the nucleotide sequence of nDiMPA2$_{2126}$, and spans from about nucleotide 504 through about nucleotide 527 of SEQ ID NO:2. Primer astacin 1$^-$ (SEQ ID NO:26) is an antisense primer complementary to a region spanning from about nucleotide 819 through about nucleotide 844 of SEQ ID NO:2.

Nucleic acid molecule nDiMPA2$_{341}$ was radiolabeled and used as a probe to screen the L3 cDNA library. Plaques which hybridized under stringent hybridization conditions (see, for example, Sambrook et al., supra, and/or Meinkoth et al., supra) to the probe were isolated and rescreened by PCR analysis using phage vector primers that flank the vector multiple cloning site containing the D. immitis insert cDNAs. These primers included an oligonucleotide having the following sequence: 5'GGAAACAGCTATGACCATG3' (denoted M13 rev, SEQ ID NO:27), and an antisense oligonucleotide having the following sequence: 5'GTAAAAC-GACGGCCAGT3' (denoted M13 univ, SEQ ID NO:28). The phage corresponding to the largest PCR product which hybridized under stringent hybridization conditions to the astacin probe was rescreened and plaque purified. A plaque-purified clone including D. immitis nucleic acid molecule L3 nDiMPA3$_{2292}$ was converted into a double-stranded recombinant molecule, herein denoted as pβgal-L3-nDiMPA3$_{2292}$, using Exassist helper phage and SOLR E. coli according to the in vivo excision protocol described in the Stratagene ZAP-cDNA Synthesis Kit®. Double stranded plasmid DNA was prepared using an alkaline lysis protocol, such as that described in Sambrook et al., ibid. Recombinant molecule pβgal-L3-nDiMPA3$_{2292}$ was transformed into E. coli to form recombinant cell E. coli:pβgal-L3-nDiMPA3$_{2292}$.

Recombinant molecule pBgal-L3-nDiMPA3$_{2292}$ was submitted to nucleic acid sequencing using the Sanger dideoxy chain termination method, as described in Sambrook et al., ibid. An about 2292-nucleotide consensus sequence of the coding strand of nucleic acid molecule nDiMPA3$_{2292}$ was determined and is presented herein as SEQ ID NO:29. SEQ ID NO:29 apparently encodes a single open reading frame. This open reading frame, denoted L3 nDiMPA3$_{2076}$ (SEQ ID NO:30), encodes a protein, denoted PDiMPA3$_{692}$, that is about 692 amino acids long (presented as SEQ ID NO:31). SEQ ID NO:30 encompasses nucleotide numbers from about 72 through about 2147 of SEQ ID NO:29.

A comparison of the deduced nucleic acid sequences of nDiMPA1$_{1299}$ (SEQ ID NO:1) and L3 nDiMPA3$_{2292}$ (SEQ ID NO:29), indicates that L3 nDiMPA3$_{2292}$ does not contain the stretch of nucleotides from about positions 1 through 15 of nDiMPA1$_{1299}$ (as numbered in SEQ ID NO:1). As discussed above with regard to the comparison of SEQ ID NO:1 and SEQ ID NO:2, it is believed that this stretch of nucleotides in SEQ ID NO:1 represents an unrelated cDNA clone that ligated to the 5' end of the astacin metalloendopeptidase nucleic acid molecule. Additionally, the stretch of nucleotides spanning from about positions 908 through 970 of nDiMPA1$_{1299}$ (as numbered in SEQ ID NO:1) are missing from L3 nDiMPA3$_{2292}$ and nDiMPA2$_{2126}$.

A comparison of the deduced nucleic acid sequences of nDiMPA2$_{2126}$ (SEQ ID NO:2) and L3 nDiMPA3$_{2292}$ (SEQ ID NO:29), indicates that the stretch of nucleotides spanning from about positions 1 through 510 of nDiMPA2$_{2126}$ (as numbered in SEQ ID NO:2) share greater than 99% homology with the stretch of nucleotides spanning from about positions 146 through 655 of L3 nDiMPA3$_{2292}$ (as numbered in SEQ ID NO:29). The stretch of nucleotides spanning from about positions 511 through 2126 of nDiMPA2$_{2126}$ (as numbered in SEQ ID NO:2) share greater than 99% homology with the stretch of nucleotides spanning from about positions 664 through 2282 of L3 nDiMPA3$_{2292}$ (as numbered in SEQ ID NO:29). nDiMPA1$_{1299}$ (SEQ ID NO:1) and nDiMPA2$_{2126}$ (SEQ ID NO:2) do not contain the stretch of nucleotides from about positions 656 through 663 of L3 nDiMPA3$_{2292}$ (as numbered in SEQ ID NO:29). Additionally, nDiMPA2$_{2126}$ does not contain nucleotides at positions 1261, 1264 and 1715 of L3 nDiMPA3$_{2292}$ (as numbered in SEQ ID NO:29); and L3 nDiMPA3$_{2292}$ does not contain the nucleotide at position 852 of nDiMPA2$_{2126}$ (as numbered in SEQ ID NO:2).

A homology search of the non-redundant protein sequence database was performed through the National Center for Biotechnology Information using the BLAST network. This database includes +SwissProt+PIR+SPUpdate+GenPept+GPUpdate. The search, which was performed using SEQ ID NO:31, showed that SEQ ID NO:31 shared significant homology at the amino acid level with known members of the astacin family of metalloendopeptidases. A comparison between the astacin domain of SEQ ID NO:31 (amino acid positions from about 122 through 326) and crayfish astacin showed about 27.3% homology at the amino acid level. The astacin domain of SEQ ID NO:31 also shared about 31.7% and 34.1% homology at the amino acid level with the astacin domains of, respectively, quail astacin and the C. elegans R151.5 gene product, (Genbank accession number U00036). SEQ ID NO:31 shows about 81.7% homology with the composite amino acid sequence derived from the five open reading frames encoded by nDiMPA2$_{2126}$ (SEQ ID NO:11).

Example 7

This Example describes the cloning and sequencing of an adult parasite astacin metalloendopeptidase nucleic acid molecule of the present invention.

Another astacin metalloendopeptidase nucleic acid molecule, denoted adult nDiMPA3$_{2032}$, was isolated from an adult D. immitis cDNA expression library, the adult expression library being produced as described for the L3 cDNA library in Example 1, as follows.

An adult D. immitis astacin metalloendopeptidase nucleic acid molecule was isolated by PCR from an adult male D. immitis cDNA expression library, using the sequence information obtained from SEQ ID NO:29. The primers used to amplify the adult nucleic acid molecule included an oligonucleotide having the following sequence: 5'CATCTC-GAGATCAGTGGAAAATTATCGAACG3' (SEQ ID NO:35, also denoted as Asta+ and corresponding to nucleotides 119–141 of SEQ ID NO:29), and an antisense oligonucleotide having the following sequence: 5'ATTGAAT- TCACTTCTTTTTCGAGTCAGGCAA3' (SEQ ID NO:36, also denoted as Asta1 and corresponding to nucleotides 2127–2150 of SEQ ID NO:29). A recombinant molecule containing a *D. immitis* astacin metalloendopeptidase nucleic acid molecule, denoted adult $nDiMPA3_{2032}$, was submitted to nucleic acid sequencing using the Sanger dideoxy chain termination method, as described in Sambrook et al., ibid. An about 2032-nucleotide consensus sequence of the coding strand of adult $nDiMPA3_{2032}$ was determined and is presented as SEQ ID NO:32. SEQ ID NO:32 apparently encodes a single open reading frame, denoted adult $nDiMPA3_{2028}$ (SEQ ID NO:33). This open reading frame encodes a protein, denoted adult $PDiMPA3_{676}$, that is about 676 amino acids long, the amino acid sequence of which is presented as SEQ ID NO:34. SEQ ID NO:33 encompasses from about nucleotide numbers 2 through about 2029 of SEQ ID NO:32.

A comparison of the deduced nucleic acid sequences of L3 $nDiMPA3_{2292}$ (SEQ ID NO:29) and adult $nDiMPA3_{2032}$ (SEQ ID NO:32) indicates that the nucleotides spanning from about positions 119 through 2150 of L3 $nDiMPA3_{2292}$ (as numbered in SEQ ID NO:29) share greater than 99% homology with the stretch of nucleotides spanning from about positions 1 through 2032 of adult $nDiMPA3_{2032}$ (as numbered in SEQ ID NO:32). Apparent differences between the L3 and adult sequences occur at about nucleotide positions 593, 596, 607, 612, 661, 1456, and 1745 of SEQ ID NO:29, and nucleotide positions 475, 478, 489, 494, 543, 1338 and 1627 of SEQ ID NO:32. These nucleotide differences result in apparent amino acid sequence differences at positions 179, 181, 197 and 462 of SEQ ID NO:31, and positions 163, 165, 181 and 446 of SEQ ID NO:34.

A homology search of the non-redundant protein sequence database was performed through the National Center for Biotechnology Information using the BLAST network. This database includes +SwissProt+PIR+SPUpdate+GenPept+GPUpdate. The search, which was performed using SEQ ID NO:34, showed that SEQ ID NO:34 shared significant homology at the amino acid level with known members of the astacin family of metalloendopeptidases. A comparison between the astacin domain of SEQ ID NO:34 (from about amino acid positions 122 through 326) and crayfish astacin showed about 26.3% homology at the amino acid level. The astacin domain of SEQ ID NO:34 also shared about 31.2% and 34.6% homology at the amino acid level with the astacin domains of, respectively, quail astacin and the *C. elegans* R151.5 gene product, (Genbank accession number U00036). SEQ ID NO:34 shows about 81.3% homology with the composite amino acid sequence derived from the five open reading frames encoded by $nDiMPA2_{2126}$ (SEQ ID NO:11).

Comparison with the regions of homology in all known astacins (as discussed in detail above), indicated that the amino acid sequences presented as SEQ ID NO:31 (L3 $PDiMPA3_{692}$, described above in Example 6) and SEQ ID NO:34 (adult $PDiMPA3_{676}$) contain three regions of homology which are conserved within about a 61 amino acid region of all known astacins. In L3 $PDiMPA3_{692}$ and adult $PDiMPA3_{676}$, these three regions span about a 60 amino acid sequence corresponding to amino acid positions 214 through 273 of L3 $PDiMPA3_{692}$ and positions 198 through 257 of adult $PDiMPA3_{676}$, (as numbered in SEQ ID NO:31 and SEQ ID NO:34, respectively). The first region of homology includes the zinc binding domain, which spans positions from about 214 through 224 of SEQ ID NO:31 and positions 198 through 208 of SEQ ID NO:34. This first region includes three histidines which are present in all astacins for zinc binding (imidazole zinc ligands) at positions 214, 218 and 224 of SEQ ID NO:31 and positions 198, 202 and 208 of SEQ ID NO:34, and a glutamate at position 215 of SEQ ID NO:31 and position 199 of SEQ ID NO:34, which is assumed to be catalytically important in all astacins. In addition, this first region includes a glycine which is important for secondary structure of the protein at position 221 of SEQ ID NO:31 and position 205 of SEQ ID NO:34, and a glutamate which forms a salt bridge with the amino terminus of the mature astacin protein at position 225 of SEQ ID NO:31 and position 209 of SEQ ID NO:34.

The second region found in L3 $PDiMPA3_{692}$ and adult $PDiMPA3_{676}$ that is conserved in all known astacins spans amino acid positions 228 through 232 of SEQ ID NO:31 and positions 212 through 216 of SEQ ID NO:34. This second region is a hydrophilic region common to all astacins.

The third region found in L3 $PDiMPA3_{692}$ and adult $PDiMPA3_{676}$ that is conserved in all known astacins spans amino acid positions 265 through 273 of SEQ ID NO:31 and positions 249 through 257 of SEQ ID NO:34, and contains a portion of the zinc binding domain. In particular, the tyrosine at position 273 of SEQ ID NO:31 and position 257 of SEQ ID NO:34 is the fourth amino acid zinc ligand. In many astacins, this tyrosine is typically at position 61 from the first amino acid of the zinc binding domain (i.e., 61 amino acids from the first histidine in the first region). In L3 $PDiMPA3_{692}$ and adult $PDiMPA3_{676}$, this tyrosine is at position 60 from the first amino acid of the zinc binding domain (i.e., 60 amino acids from the first histidine in the first region at position 214 of SEQ ID NO:31 and position 198 of SEQ ID NO:34).

Example 8

This Example describes the cloning and sequencing of a filariid nematode cysteine protease nucleic acid molecule of the present invention.

A *D. immitis* cysteine protease nucleic acid molecule of about 143 nucleotides, denoted $nDiCP_{431}$, representing a partial *D. immitis* cysteine protease gene, was PCR amplified from *D. immitis* genomic DNA that had been extracted from adult female *D.immitis* worms using standard protocols similar to that described in Sambrook et al, ibid. The two primers used in the PCR amplification reaction included a 4-fold degenerate primer having SEQ ID NO:18, namely 5'CGGGATCCTGTGGWTCATGYTGGGC 3' (denoted 25C; BamHI site in bold; W is A or T; Y is C or T) and an 8-fold degenerate antisense primer having SEQ ID No:19, namely 5'TAICCICCRTTRCAICCYTC 3' (denoted G65; R is A or G; Y is C or T; I is inosine). Both primers were designed from published sequence of cysteine proteases. Primer 25C was further refined in that *D. immitis* codon bias was incorporated into 25C to reduce the degeneracy. The inventors found such codon bias was necessary to effectively isolate *D. immitis* cysteine protease nucleic acid molecules of the present invention.

The amplified PCR fragment, namely $nDiCP_{143}$, was gel purified and cloned into the pCRII cloning vector (available from Invitrogen, San Diego, Calif.), following manufacturer's instructions. An about 143 nucleotide sequence of $nDiCPI_{143}$ was determined and is presented as SEQ ID NO:12. SEQ ID NO:12 apparently encodes a protein of about 47 amino acids, which is presented as SEQ ID NO:13. The translation initiation site of the protein and the translation termination codon are not contained within this genomic clone.

A homology search of the non-redundant protein sequence database was performed through the National Center for Biotechnology Information using the BLAST network. This database includes +SwissProt+PIR+SPUpdate+GenPept+GPUpdate. The search was performed using SEQ ID NO:13 and showed significant homology to numerous cysteine proteinases. The highest scoring matches at the amino acid level include soybean probable thiol protease precursor (Genbank accession number P22895), barley cysteine proteinase EP-B 1 precursor (Genbank accession number P25249) and barley cysteine proteinase EP-B 4 precursor (Genbank accession number P25250). Parasite specific cysteine proteases having homology to SEQ ID NO:13 include cysteine proteases from *Trypanosoma brucei* (Genbank accession numbers S07051 and S12099), *Leishmania pifanoi* (Genbank accession number B48566), *L. mexicana* (Genbank accession number S25003), *T. congolense* (Genbank accession number (37048), and *Trichomonas vaginalis* (Genbank accession number X77220). SEQ ID NO:13 shared about 16 percent, about 22 percent, about 24 percent, about 35 percent, about 39 percent, about 44 percent and about 49 percent homology at the amino acid level with cysteine proteases from, respectively, *H. contortus* (a nematode), *Schistosoma mansoni* (a trematode), *C. elegans* (a nematode), *Fasciola hepatica* (a trematode), *Entamoeba histolytica* (a protozoa), *Trypanosoma cruzi* (a protozoa) and *T. brucie*. SEQ ID NO:13 also shared about 50 percent amino acid homology with human cathepsin. SEQ ID NO:13 also shared about 56 percent amino acid homology with a *Paragonimus westermani* cysteine protease reported in European Patent Application Publication No. 0524834A2, by Hamajima et al., published Jan. 27, 1993. The serine at about position 30 and the cysteine at about position 37 of SEQ ID NO:13 were conserved in all of these cysteine proteases. Note that these homology calculations did not include the amino acids encoded by DNA primers SEQ ID NO:18 and SEQ ID NO:19. As such, the region used in the homology calculations spanned from about amino acid position 6 through 41 of SEQ ID NO:13.

Example 9

This Example discloses the production of a recombinant cell of the present invention and its use to produce a filariid nematode cysteine protease protein of the present invention.

Recombinant molecule ptrcHis-nDiCP$_{421}$, containing nucleotides from about positions 2 through 143 of nDiCP$_{143}$ (as numbered in SEQ ID NO:12) operatively linked to trc transcription control sequences and to a fusion sequence encoding a poly-histidine segment comprising 6 histidines was produced in the following manner. An about 142-nucleotide DNA fragment containing nucleotides spanning from about 2 through about 143 of nDiCP$_{143}$ (as numbered in SEQ ID NO:12), denoted nDiCP$_{142}$ (characterized by a coding strand having the nucleic acid sequence of SEQ ID NO:23), was sequentially digested from nDiCP$_{143}$ with BamHI restriction endonuclease followed by digestion with EcoRI. Nucleic acid molecule nDiCP$_{142}$ was gel purified and directionally subcloned into expression vector pTrcHisA (available from Invitrogen) that had been cleaved with BamHI and EcoRI and subsequently been gel purified. The resulting recombinant molecule, namely ptrcHis-nDiCP$_{142}$ was transformed into *E. coli* to form recombinant cell *E. coli*: ptrcHis-nDiCP$_{142}$.

Recombinant cell *E. coli*:ptrcHis-nDiCP$_{142}$ is cultured in shake flasks containing an enriched bacterial growth medium containing about 0.1 mg/ml ampicillin at about 37° C. When the cells reach an OD$_{600}$ of about 0.3, expression of *E. coli*:ptrcHis-nDiCP$_{142}$ is induced by addition of about 1 mM isopropyl-β-D-thiogalactoside (IPTG), and the cells cultured for about 3 hours at about 37° C. Protein production is monitored by SDS-PAGE of recombinant cell lysates, followed by Coomassie blue staining, using standard techniques. Recombinant cell *E. coli*:ptrcHis-nDiCP$_{142}$ produces a fusion protein, denoted herein as PHIS-PDiCP$_{142}$, the deduced amino acid sequence of which is presented as SEQ ID NO:24, that is not produced by cells transformed with the pTrcHisA plasmid lacking a filariid nucleic acid molecule insert.

Example 10

This Example demonstrates that the protease inhibitors bestatin and phosphoramidon are able to inhibit *D. immitis* larval development, particularly molting. Bestatin (available from Enzyme Systems Products, Livermore, Calif.) primarily, if not exclusively, inhibits amino peptidases and other exopeptidases. Phosphoramidon (also available from Enzyme Systems Products) specifically inhibits thermolysin and collagenase as well as metalloendoproteases from *Bacillus subtilis, Streptomyces griseus* and *Pseudomonas aeruginosa* microorganisms.

*D. immitis* larvae were cultured in NI media as described, for example, in U.S. patent application Ser. No. 08/153,554, ibid. NI medium contains a 1:1 mixture of NCTC-135 and Iscove's modified Dulbecco medium (available from Sigma Chemical Co., St. Louis, Mo.), 20% SeruMax, 2.5 micrograms (μg) of amphotericin B per ml, 0.1 nanograms (ng) of gentamicin per ml, 50 μg of sulfadiazine per ml and 10 μg of trimethoprim per ml. Larvae, at a concentration of about 200 L3 per milliliter (ml) of NI medium, were distributed in 0.5-ml aliquots into the wells of a 24-well plate. The volume in each well was adjusted to 1 ml using NI medium and 10-millimolar (mM) stocks of bestatin or phosphoramidon, each of which was dissolved in NI media. The final concentration of inhibitor in the culture wells was either 0, 1, 2.5 or 5 mM. Larvae were incubated at about 37° C., 5% CO2 and 95% relative humidity. Larvae were observed daily and the percent molt (% molt) was evaluated at 72 hours. The percent molt was calculated for each well by dividing the number of cuticles by the number of larvae per well and multiplying by 100. There were three wells for each inhibitor concentration and six wells for the untreated control. The results of this study appear in Table 1.

TABLE 1

Effect of protease Inhibitors on Larval Molting

| Group | Concentration | % molt | s.d. | % reduction | Fi | Sc |
|---|---|---|---|---|---|---|
| Control | NA | 82.6 | 15.8 | NA | NA | NA |
| Bestatin | 1.0 mM | 60.0 | 9.0 | 27.3 | * | |
| | 2.5 mM | 34.8 | 4.3 | 57.9 | * | * |
| | 5.0 mM | 4.9 | 0.9 | 94.1 | * | * |
| Phosphoramidon | 1.0 mM | 42.6 | 2.1 | 48.4 | * | * |
| | 2.5 mM | 12.3 | 1.2 | 85.1 | * | * |
| | 5.0 mM | 0.0 | 0.0 | 100.0 | * | * |

The results indicate that treatment of L3 by bestatin and phosphoramidon significantly reduces the ability of the larvae to molt. An analysis of variance was performed using % molt. The difference overall was significant (P=0.0001). Fisher PLSD (Fi) and Scheffe F-test (Sc) multiple comparisons comparing each group to the control were done after the ANOVA (* represent significant differences of p≦0.05, NA=not applicable).

It was also observed that, in general, bestatin-treated larvae moved much more slowly throughout the study compared to controls whereas phosphoramidon-treated larvae were very active compared to controls. Cuticle separation appeared to be occurring in the phosphoramidon-treated larvae, but the larvae could not open up the old cuticle and escape. The phosphoramidon-treated larvae were in poor shape by the end of the study. While not being bound by theory, it is believed that these phenomena suggest two distinct effects and that the inhibitors may be targeting different enzymes.

Example 11

Example 11 describes the isolation and characterization of protein-containing fractions from excretory/secretory (ES) products of D. immitis larvae.

ES products from about 11,600 D. immitis L3/L4 were collected and concentrated as described, for example, in U.S. patent application Serial No. 08/153,554, ibid. The buffer was exchanged to 20 mM piperazine-HCl, pH 6.0, 0.005% Brij 35 using a Centriprep 10 (available from Amicon Inc., Beverly, Mass.). The resulting mixture was separated on a Mono-Q column (anion exchange) (available from Pharmacia Biotech Inc., Piscataway, N.J.) equilibrated in 20 mM piperazine-HCl, pH 6.0 using an increasing gradient of sodium chloride. Each fraction was then brought to 0.005% Brij 35. Buffer A was 20 mM piperazine-HCl, pH 6.0. Buffer B was 1 M sodium chloride in 20 mM piperazine-HCl, pH 6.0. The chromatography program was: (a) 0% B for 5 minutes; (b) 0% to about 50% B over 25 minutes; (c) hold 3 minutes; (d) about 50% to 100% B over 5 minutes. The flow rate was 0.5 ml per minute. Fractions were collected every minute.

The collected fractions were assayed for metalloprotease activity using the fluorogenic compound H-phenylalanine-7-amido-4-methylcoumarin (H-Phe-AMC). The assay was conducted as follows. A stock solution of 10 mM H-Phe-AMC in dimethyl sulfoxide (DMSO) was diluted 1:200 with 100 mM Tris-HCl, pH 7.0. About 100 microliters ($\mu$l) of the diluted stock solution was placed in each of a desired number of wells in a 96-well microtiter plate. To each well was added 25 $\mu$l of the fractions, or control samples, to be tested. The resulting mixture was incubated at about 37° C. for at least 2 hours. The microtiter plate was then placed on a UV light box and photographed to identify fractions in which AMC was cleaved (released AMC glows under such conditions).

Fractions 20 and 21 collected from the anion exchange both exhibited metalloproteolytic activity. An aliquot of fraction 21 was concentrated and evaluated by SDS-PAGE (14% Tris-glycine). One major band was detected that migrated with an apparently molecule weight of about 60 kD.

Anion exchange fraction 21 was then applied to size exclusion chromatography as described in U.S. patent application Ser. No. 08/153,554, ibid. Specifically, Fraction 21 from the anion exchange column was applied to a TSK 3000 SW column (available from Beckman Instruments Inc., Fullerton, Calif) in 50 mM Tris-HCl, pH 7.5, 150 mM sodium chloride, at a flow rate of 0.5 ml per minute. Fractions were collected every 0.5 minutes. When assayed using the microtiter plate fluorescent assay, fractions 21 and 22 were positive. The relative time of elution of these fractions was very close to the elution time of bovine serum albumin, which has a molecular weight of about 62 to 66 kD.

Anion exchange fraction 21 was also submitted to isoelectric focussing under "native" conditions. The resultant gel was sliced into 1 mm fractions and the strips assayed by the microtiter plate fluorescent assay. The active fraction was in a region having a pI of about 6.8.

In a separate study, ES from about 2500 larvae was submitted to electrophoresis through each of two lanes of Novex Zymogel (available from Novex, San Diego, Calif.). Zymogel contains about 0.1 percent gelatin. The two lanes were soaked in 2.5% Triton X-100 for about 30 minutes and subsequently washed in reaction buffer (50 mM Tris-HCl, pH 7.0, 5 mM calcium chloride, 0.02% Brij 35 and 200 mM sodium chloride) for about 30 minutes. One lane was then incubated in reaction buffer at about 37° C. for 66 hours. The other lane was incubated in reaction buffer containing 2 mM EDTA for the same amount of time. Both lanes were then stained in 0.5% CBB-R250, 40% methanol, 10% acetic acid and destained in 40% methanol, 10% acetic acid in order to detect collagenase activity. Activity was identified by a clear zone in a blue background. ES proteins displaying metalloprotease activity that was completely inhibited by EDTA migrated with apparent molecular weights of about 60 kD, about 95 kD and at least about 200 kD.

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 1299 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

TTTTTTTTTT TTTTTTTTGT TTCATTGTTC AGTCAGTGGA AAATTATCGA ACGCAGAAAG    60

-continued

| | |
|---|---|
| CATCACGAAA TACGTTAGAT CACATCAAAC AACTTATCAC CTTGAACGTA CAAAGAGAGA | 120 |
| TTGGAAACAT AGATGATAAG ACATTAGCTG ATGAAATAGT ATTACAACGA CGGGATCCTG | 180 |
| AGGCAAAATG GCATCATAAT GAACTATTCA TTAATGATCC AGATGCATAC TATCAAGGCG | 240 |
| ATGTCGATTT GTCGGAAAAA CAAGCCGAAA TTCTAAGCGA ACATTTTAAA AATGAAATTG | 300 |
| CTTTAACAGA GAAAGACGAC ACAATAATAC GGCGAAAAAA GAGCATTGGT CGTGAACCAT | 360 |
| TTTACGTAAG ATGGAATCAT AAACGTCCCA TTAGCTATGA ATTTGCGGAA AGTATTCCAT | 420 |
| TAGAAACACG TAGAAAAATT CGTTCAGCAA TAGCAATGTG GGAAGAACGA ACATGCATAC | 480 |
| GATTCCAAGA AAATGGCCCA AATGTAGATC GAATTGAATT TTACGACGGT GGCGGTTGTT | 540 |
| CAAGTTTTGT CGGCCGAACA GGAGGGAATT TCAATTTCAA CACCAGGATG TGATATTATT | 600 |
| GGTATTATAT CACATGAAAT TGGTCATACT TTAGGAATAT TTCATGAGCA AGCACGTCGT | 660 |
| GATCAAAAAA ATCATATTTT TATTAATTAC AACAATATTC CATCAAGCCG TTGGAACAAT | 720 |
| TTTTTTCCAT TATCAGAATA TGAAGCTGAT ATGTTTAATT TACCTTATGA TACAGGATCA | 780 |
| GTAATGCACT ATGGTTCATA CGGATTTGCA AGAAATCCGT ATGAACCAAC TATTACAACA | 840 |
| CGTGATAAAT TTCAACAGTA CACAATTGGG CAACGTGAAG GGCCATCATT TCTGGATTAT | 900 |
| GCATCTGTTA AGCTTTATCT ACAAACGCAT AATGATATAT GTTATCAAAT GGATGATAAT | 960 |
| TTCAATAAGT ATAAACAGCG CTTATCGTTG TACAGAACAA TGTGCTGATA TGCACTGCGA | 1020 |
| TCATAATGGT TATCCGGATC CTAATAATTG CGCGAAATGC TTGTGTCCAG ATGGTTTTGC | 1080 |
| TGGTCGTACC TGTCAATTTG TTCAATATAC ATCTTGCGGA GCTCTCATTA AGGTAAGTAT | 1140 |
| TGTCTTTTGA CCTCTTCTCT GACTAAAATA TAAGTTAAGC ATATGTATCT TCCGTCTAAT | 1200 |
| GATTTTCTTG ATTTTGATTT GTTCAATGCT CTTCTTGATA ATAATATAAA AATTTTTGAA | 1260 |
| AATAAAGTTA ACTTTTGGTC AAAAAAAAAA AAAAAAAA | 1299 |

(2) INFORMATION FOR SEQ ID NO:2:

(i) SEQUENCE CHARACTERISTICS:
        (A) LENGTH: 2126 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

| | |
|---|---|
| GAAAGCATCA CGAAATACGT TAGATCACAT CAAACAACTT ATCACCTTGA ACGTACAAAG | 60 |
| AGAGATTGGA AACATAGATG ATAAGACATT AGCTGATGAA ATAGTATTAC AACGACGGGA | 120 |
| TCCTGAGGCA AAATGGCATC ATAATGAACT ATTCATTAAT GATCCAGATG CATACTATCA | 180 |
| AGGCGATGTC GATTTGTCGG AAAAACAAGC CGAAATTCTA AGCGAACATT TTAAAAATGA | 240 |
| AATTGCTTTA ACAGAGAAAG ACGACACAAT AATACGGCGA AAAAGAGCA TTGGTCGTGA | 300 |
| ACCATTTTAC GTAAGATGGA ATCATAAACG TCCCATTAGC TATGAATTTG CGGAAAGTAT | 360 |
| TCCATTAGAA ACACGTAGAA AAATTCGTTC AGCAATAGCA ATGTGGGAAG AACGAACATG | 420 |
| CATACGATTC AAGAAAATG GCCCAAATGT AGATCGAATT GAATTTTACG ACGGTGGCGG | 480 |
| TTGTTCAAGT TTTGTCGGCC GAACAGGAGG GAATTTCAAT TTCAACACCA GGATGTGATA | 540 |
| TTATTGGTAT TATATCACAT GAAATTGGTC ATACTTTAGG AATATTTCAT GAGCAAGCAC | 600 |
| GTCGTGATCA AAAAATCAT ATTTTTATTA ATTACAACAA TATTCCATCA AGCCGTTGGA | 660 |
| ACAATTTTTT TCCATTATCA GAATATGAAG CTGATATGTT TAATTTACCT TATGATACAG | 720 |

-continued

```
GATCAGTAAT GCACTATGGT TCATACGGAT TTGCAAGAAA TCCGTATGAA CCAACTATTA        780

CAACACGTGA TAAATTTCAA CAGTACACAA TTGGGCAACG TGAAGGGCCA TCATTTCTGG        840

ATTATGCATC TGATAAACAG CGCTTATCGT TGTACAGAAC AATGTGCTGA TATGCACTGC        900

GATCATAATG GTTATCCGGA TCCTAATAAT GCGCGAAAT GCTTGTGTCC AGATGGTTTT         960

GCTGGTCGTA CCTGTCAATT TGTTCAATAT ACATCTTGCG GAGCTCTCAT TAAGGCGAGG       1020

AAAATGCCTG TTACGATTTC GAGCCCAAAT TATCCAAACT TCTTCAATGT TGGTGATCAA       1080

TGTATTTGGT TGCTTACAGC TCCACGCGTG ATTCGTAAAT TTGCAGTTTG TTGAACAATT       1140

TCAATTACAA TGTGAAGATA CGTGTGATAA ATCCTATGTA GAAGTGAAAG CTGACGCTGA       1200

TTTTCGACCT ACTGGATATC GATTTTGTTG TTCGCGAGTG CCACGTCATA TTTTTCAATC       1260

TGCGACAAAC GAGATGGTAG TAATATTTCG CGGTTTTGGT GATGCGGGAA ATGGCTTTAA       1320

AGCTAAAATT TGGTCAAACG TAGATGATGA TATAGCTAAT ACAATTGTAA CAACTGAAAT       1380

GGCAAAAATT TCGGAAAAAA TACCGAAGCT AACAGTTCCA ATAGTTAAAA CTATTACCAC       1440

TCCTACAATA ACAACTACTA CTGCTTTCAT GATATCACCC AAGAAAGGCA ATGTCACCGC       1500

CACGAGAGTT GCTATCACTA CTACGCCGAC TACTACAATT ACTACGACTA TTGCCGGTAC       1560

GTACCAATCA CCGTAACTAA TAATACTACA CCTGTAGTAA GTGAAACTTT ACCATCATTG       1620

CCAGTCAAGA TTCGAAACAA AATAGGTGCA TGCGAATGTG GTGAATGGAC AGAATGGACA       1680

GGTCCATGCT CTCAAGAATG TGGCGGTTGC GGAAAACGTC TTCGAACACG TCAGTGTTCA       1740

TCAGATACGG AATGTAGAAC AGAAGAAAAA CGTGCGTGTG CTTTTAAGTT TGCCCATACG       1800

GGACTAATTT CCTTATCAAT AATGGAGAGT TTCATATACT TTGGAAGGGC TGCTGTGTTG       1860

GTCTATTCCG ATCGGGAGAT ATGTGTTCAG CACTTGATGA TAACGAGAAT CCATTTCTGA       1920

AATTTCTAGA ATCACTGTTG AACATGCAAG ATTCTCGAAA AAACGATAAT TTGCCTGACT       1980

CGAAAAAGAA GTGATTGAAT GATTCGATAA TATTGATTAA TAAAACGGGT TGTATTCTCG       2040

TCATAGAGTA TCCGTTGATG TTTTTATCCA AAAAATTCTC TTGCTTTTAA TTATTGTGAA       2100

TAAAACTTTT GTTTACCCAA AAAAA                                             2126
```

(2) INFORMATION FOR SEQ ID NO:3:

(i) SEQUENCE CHARACTERISTICS:
        (A) LENGTH: 191 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

```
Cys Phe Ile Val Gln Ser Val Glu Asn Tyr Arg Thr Gln Lys Ala Ser
1               5                  10                  15

Arg Asn Thr Leu Asp His Ile Lys Gln Leu Ile Thr Leu Asn Val Gln
            20                  25                  30

Arg Glu Ile Gly Asn Ile Asp Asp Lys Thr Leu Ala Asp Glu Ile Val
        35                  40                  45

Leu Gln Arg Arg Asp Pro Glu Ala Lys Trp His His Asn Glu Leu Phe
    50                  55                  60

Ile Asn Asp Pro Asp Ala Tyr Tyr Gln Gly Asp Val Asp Leu Ser Glu
65                  70                  75                  80

Lys Gln Ala Glu Ile Leu Ser Glu His Phe Lys Asn Glu Ile Ala Leu
                85                  90                  95
```

-continued

```
Thr Glu Lys Asp Asp Thr Ile Ile Arg Arg Lys Lys Ser Ile Gly Arg
            100                 105                 110

Glu Pro Phe Tyr Val Arg Trp Asn His Lys Arg Pro Ile Ser Tyr Glu
            115                 120                 125

Phe Ala Glu Ser Ile Pro Leu Glu Thr Arg Arg Lys Ile Arg Ser Ala
            130                 135                 140

Ile Ala Met Trp Glu Arg Thr Cys Ile Arg Phe Gln Glu Asn Gly
145                 150                 155                 160

Pro Asn Val Asp Arg Ile Glu Phe Tyr Asp Gly Gly Cys Ser Ser
                    165                 170                 175

Phe Val Gly Arg Thr Gly Gly Asn Phe Asn Phe Asn Thr Arg Met
                    180                 185                 190
```

(2) INFORMATION FOR SEQ ID NO:4:

(i) SEQUENCE CHARACTERISTICS:
       (A) LENGTH: 141 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:4:

```
Ile Glu Leu Asn Phe Thr Thr Val Ala Val Gln Val Leu Ser Ala
1               5                   10                  15

Glu Gln Glu Gly Ile Ser Ile Ser Thr Pro Gly Cys Asp Ile Ile Gly
                20                  25                  30

Ile Ile Ser His Glu Ile Gly His Thr Leu Gly Ile Phe His Glu Gln
            35                  40                  45

Ala Arg Arg Asp Gln Lys Asn His Ile Phe Ile Asn Tyr Asn Asn Ile
50                  55                  60

Pro Ser Ser Arg Trp Asn Asn Phe Phe Pro Leu Ser Glu Tyr Glu Ala
65                  70                  75                  80

Asp Met Phe Asn Leu Pro Tyr Asp Thr Gly Ser Val Met His Tyr Gly
                85                  90                  95

Ser Tyr Gly Phe Ala Arg Asn Pro Tyr Glu Pro Thr Ile Thr Thr Arg
                100                 105                 110

Asp Lys Phe Gln Gln Tyr Thr Ile Gly Gln Arg Glu Gly Pro Ser Phe
            115                 120                 125

Leu Asp Tyr Ala Ser Val Lys Leu Tyr Leu Gln Thr His
            130                 135                 140
```

(2) INFORMATION FOR SEQ ID NO:5:

(i) SEQUENCE CHARACTERISTICS:
       (A) LENGTH: 121 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:5:

```
Cys Thr Met Val His Thr Asp Leu Gln Glu Ile Arg Met Asn Gln Leu
1               5                   10                  15

Leu Gln His Val Ile Asn Phe Asn Ser Thr Gln Leu Gly Asn Val Lys
                20                  25                  30

Gly His His Phe Trp Ile Met His Leu Leu Ser Phe Ile Tyr Lys Arg
            35                  40                  45
```

```
Ile Asn Asp Ile Val Ile Lys Trp Met Ile Ile Ser Ile Ser Ile Asn
    50                  55                  60

Ser Ala Tyr Arg Cys Thr Glu Gln Cys Ala Asp Met His Cys Asp His
65                  70                  75                  80

Asn Gly Tyr Pro Asp Pro Asn Asn Cys Ala Lys Cys Leu Cys Pro Asp
                85                  90                  95

Gly Phe Ala Gly Arg Thr Cys Gln Phe Val Gln Tyr Thr Ser Cys Gly
                100                 105                 110

Ala Leu Ile Lys Val Ser Ile Val Phe
            115                 120
```

(2) INFORMATION FOR SEQ ID NO:6:

(i) SEQUENCE CHARACTERISTICS:
        (A) LENGTH: 178 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

```
Lys Ala Ser Arg Asn Thr Leu Asp His Ile Lys Gln Leu Ile Thr Leu
1               5                   10                  15

Asn Val Gln Arg Glu Ile Gly Asn Ile Asp Asp Lys Thr Leu Ala Asp
                20                  25                  30

Glu Ile Val Leu Gln Arg Arg Asp Pro Glu Ala Lys Trp His His Asn
                35                  40                  45

Glu Leu Phe Ile Asn Asp Pro Asp Ala Tyr Tyr Gln Gly Asp Val Asp
    50                  55                  60

Leu Ser Glu Lys Gln Ala Glu Ile Leu Ser Glu His Phe Lys Asn Glu
65                  70                  75                  80

Ile Ala Leu Thr Glu Lys Asp Asp Thr Ile Ile Arg Arg Lys Lys Ser
                85                  90                  95

Ile Gly Arg Glu Pro Phe Tyr Val Arg Trp Asn His Lys Arg Pro Ile
                100                 105                 110

Ser Tyr Glu Phe Ala Glu Ser Ile Pro Leu Glu Thr Arg Arg Lys Ile
                115                 120                 125

Arg Ser Ala Ile Ala Met Trp Glu Glu Arg Thr Cys Ile Arg Phe Gln
130                 135                 140

Glu Asn Gly Pro Asn Val Asp Arg Ile Glu Phe Tyr Asp Gly Gly Gly
145                 150                 155                 160

Cys Ser Ser Phe Val Gly Arg Thr Gly Gly Asn Phe Asn Phe Asn Thr
                165                 170                 175

Arg Met
```

(2) INFORMATION FOR SEQ ID NO:7:

(i) SEQUENCE CHARACTERISTICS:
        (A) LENGTH: 145 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

```
Ile Glu Leu Asn Phe Thr Thr Val Ala Val Val Gln Val Leu Ser Ala
1               5                   10                  15
```

```
Glu Gln Glu Gly Ile Ser Ile Ser Thr Pro Gly Cys Asp Ile Ile Gly
                20                  25                  30

Ile Ile Ser His Glu Ile Gly His Thr Leu Gly Ile Phe His Glu Gln
            35                  40                  45

Ala Arg Arg Asp Gln Lys Asn His Ile Phe Ile Asn Tyr Asn Asn Ile
 50                      55                  60

Pro Ser Ser Arg Trp Asn Asn Phe Phe Pro Leu Ser Glu Tyr Glu Ala
 65                  70                  75                  80

Asp Met Phe Asn Leu Pro Tyr Asp Thr Gly Ser Val Met His Tyr Gly
                 85                  90                  95

Ser Tyr Gly Phe Ala Arg Asn Pro Tyr Glu Pro Thr Ile Thr Thr Arg
                100                 105                 110

Asp Lys Phe Gln Gln Tyr Thr Ile Gly Gln Arg Glu Gly Pro Ser Phe
            115                 120                 125

Leu Asp Tyr Ala Ser Asp Lys Gln Arg Leu Ser Leu Tyr Arg Thr Met
        130                 135                 140

Cys
145

(2) INFORMATION FOR SEQ ID NO:8:

(i) SEQUENCE CHARACTERISTICS:
        (A) LENGTH: 134 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

Cys Thr Met Val His Thr Asp Leu Gln Glu Ile Arg Met Asn Gln Leu
 1               5                  10                  15

Leu Gln His Val Ile Asn Phe Asn Ser Thr Gln Leu Gly Asn Val Lys
                20                  25                  30

Gly His His Phe Trp Ile Met His Leu Ile Asn Ser Ala Tyr Arg Cys
            35                  40                  45

Thr Glu Gln Cys Ala Asp Met His Cys Asp His Asn Gly Tyr Pro Asp
 50                      55                  60

Pro Asn Asn Cys Ala Lys Cys Leu Cys Pro Asp Gly Phe Ala Gly Arg
 65                  70                  75                  80

Thr Cys Gln Phe Val Gln Tyr Ser Cys Gly Ala Leu Ile Lys Ala
                 85                  90                  95

Arg Lys Met Pro Val Thr Ile Ser Ser Pro Asn Tyr Pro Asn Phe Phe
                100                 105                 110

Asn Val Gly Asp Gln Cys Ile Trp Leu Leu Thr Ala Pro Arg Val Ile
            115                 120                 125

Arg Lys Phe Ala Val Cys
        130

(2) INFORMATION FOR SEQ ID NO:9:

(i) SEQUENCE CHARACTERISTICS:
        (A) LENGTH: 154 amino acids
        (B) TYPE: amino acid
        (C) STRANDEDNESS:
        (D) TOPOLOGY: linear (ii) MOLECULE TYPE: protein
```

(xi) SEQUENCE DESCRIPTION: SEQ ID NO:9:

```
Phe Val Asn Leu Gln Phe Val Glu Gln Phe Gln Leu Gln Cys Glu Asp
 1               5                  10                  15

Thr Cys Asp Lys Ser Tyr Val Glu Val Lys Ala Asp Ala Asp Phe Arg
                20                  25                  30

Pro Thr Gly Tyr Arg Phe Cys Cys Ser Arg Val Pro Arg His Ile Phe
            35                  40                  45

Gln Ser Ala Thr Asn Glu Met Val Val Ile Phe Arg Gly Phe Gly Asp
        50                  55                  60

Ala Gly Asn Gly Phe Lys Ala Lys Ile Trp Ser Asn Val Asp Asp Asp
65                  70                  75                  80

Ile Ala Asn Thr Ile Val Thr Thr Glu Met Ala Lys Ile Ser Glu Lys
                85                  90                  95

Ile Pro Lys Leu Thr Val Pro Ile Val Lys Thr Ile Thr Thr Pro Thr
            100                 105                 110

Ile Thr Thr Thr Thr Ala Phe Met Ile Ser Pro Lys Lys Gly Asn Val
        115                 120                 125

Thr Ala Thr Arg Asx Ala Ile Thr Thr Thr Pro Thr Thr Thr Ile Thr
    130                 135                 140

Thr Thr Ile Ala Gly Thr Tyr Gln Ser Pro
145                 150
```

(2) INFORMATION FOR SEQ ID NO:10:

(i) SEQUENCE CHARACTERISTICS:
        (A) LENGTH: 163 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

```
Asn Tyr Tyr His Ser Tyr Asn Asn Tyr Tyr Cys Phe His Asp Ile
 1               5                  10                  15

Thr Gln Glu Arg Gln Cys His Arg His Glu Ser Cys Tyr His Tyr Tyr
                20                  25                  30

Ala Asp Tyr Tyr Asn Tyr Tyr Asp Tyr Cys Arg Tyr Val Pro Ile Thr
            35                  40                  45

Val Thr Asn Asn Thr Thr Pro Val Val Ser Glu Thr Leu Pro Ser Leu
        50                  55                  60

Pro Val Lys Ile Arg Asn Lys Ile Gly Ala Cys Glu Cys Gly Glu Trp
65                  70                  75                  80

Thr Glu Trp Thr Gly Pro Cys Ser Gln Glu Cys Gly Cys Gly Lys
                85                  90                  95

Arg Leu Arg Thr Arg Gln Cys Ser Ser Asp Thr Glu Cys Arg Thr Glu
            100                 105                 110

Glu Lys Arg Ala Cys Ala Phe Lys Phe Ala His Thr Gly Leu Ile Ser
        115                 120                 125

Leu Ser Ile Met Glu Ser Phe Ile Tyr Phe Gly Arg Ala Ala Val Leu
    130                 135                 140

Val Tyr Ser Asp Arg Glu Ile Cys Val Gln His Leu Met Ile Thr Arg
145                 150                 155                 160

Ile His Phe
```

(2) INFORMATION FOR SEQ ID NO:11:

(i) SEQUENCE CHARACTERISTICS:
   (A) LENGTH: 638 amino acids
   (B) TYPE: amino acid
   (C) STRANDEDNESS:
   (D) TOPOLOGY: linear (ii) MOLECULE TYPE: protein (xi) SEQUENCE DESCRIPTION: SEQ ID NO:11:

```
Lys Ala Ser Arg Asn Thr Leu Asp His Ile Lys Gln Leu Ile Thr Leu
1               5                   10                  15

Asn Val Gln Arg Glu Ile Gly Asn Ile Asp Asp Lys Thr Leu Ala Asp
            20                  25                  30

Glu Ile Val Leu Gln Arg Arg Asp Pro Glu Ala Lys Trp His His Asn
        35                  40                  45

Glu Leu Phe Ile Asn Asp Pro Asp Ala Tyr Tyr Gln Gly Asp Val Asp
    50                  55                  60

Leu Ser Glu Lys Gln Ala Glu Ile Leu Ser Glu His Phe Lys Leu Asn
65                  70                  75                  80

Glu Ile Ala Leu Thr Glu Lys Asp Asp Thr Ile Ile Arg Arg Lys Lys
                85                  90                  95

Ser Ile Gly Arg Glu Pro Phe Tyr Val Arg Trp Asn His Lys Arg Pro
            100                 105                 110

Ile Ser Tyr Glu Phe Ala Glu Ser Ile Pro Leu Glu Thr Arg Arg Lys
        115                 120                 125

Ile Arg Ser Ala Ile Ala Met Trp Glu Glu Arg Thr Cys Ile Arg Phe
    130                 135                 140

Gln Glu Asn Gly Pro Asn Val Asp Arg Ile Glu Phe Tyr Asp Gly Gly
145                 150                 155                 160

Gly Cys Ser Ser Phe Val Gly Arg Gln Glu Gly Ile Ser Ile Ser Thr
                165                 170                 175

Pro Gly Cys Asp Ile Ile Gly Ile Ile Ser His Glu Ile Gly His Thr
            180                 185                 190

Leu Gly Ile Phe His Glu Gln Ala Arg Arg Asp Gln Lys Asn His Ile
        195                 200                 205

Phe Ile Asn Tyr Asn Asn Ile Pro Ser Ser Arg Trp Asn Asn Phe Phe
    210                 215                 220

Pro Leu Ser Glu Tyr Glu Ala Asp Met Phe Asn Leu Pro Tyr Asp Thr
225                 230                 235                 240

Gly Ser Val Met His Tyr Gly Ser Tyr Gly Phe Ala Arg Asn Pro Tyr
                245                 250                 255

Glu Pro Thr Ile Thr Thr Arg Asp Lys Phe Gln Gln Tyr Thr Ile Gly
            260                 265                 270

Gln Arg Glu Gly Pro Ser Phe Leu Asp Met His Leu Ile Asn Ser Ala
        275                 280                 285

Tyr Arg Cys Thr Glu Gln Cys Ala Asp Met His Cys Asp His Asn Gly
    290                 295                 300

Tyr Pro Asp Pro Asn Asn Cys Ala Lys Cys Leu Cys Pro Asp Gly Phe
305                 310                 315                 320

Ala Gly Arg Thr Cys Gln Phe Val Gln Tyr Thr Ser Cys Gly Ala Leu
                325                 330                 335

Ile Lys Ala Arg Lys Met Pro Val Thr Ile Ser Ser Pro Asn Tyr Pro
            340                 345                 350

Asn Phe Phe Asn Tyr Gly Asp Gln Cys Ile Trp Leu Leu Thr Ala Pro
        355                 360                 365
```

```
Arg Val Phe Val Asn Leu Gln Phe Val Glu Gln Phe Gln Leu Gln Cys
    370                 375                 380
Glu Asp Thr Cys Asp Lys Ser Tyr Val Glu Val Lys Ala Asp Ala Asp
385                 390                 395                 400
Phe Arg Pro Thr Gly Tyr Arg Phe Cys Cys Ser Arg Val Pro Arg His
            405                 410                 415
Ile Phe Gln Ser Ala Thr Asn Glu Met Val Val Ile Phe Arg Gly Phe
                420                 425                 430
Gly Asp Ala Gly Asn Gly Phe Lys Ala Lys Ile Trp Ser Asn Val Asp
            435                 440                 445
Asp Asp Ile Ala Asn Thr Ile Val Thr Thr Glu Met Ala Lys Ile Ser
450                 455                 460
Glu Lys Ile Pro Lys Leu Thr Val Pro Ile Val Lys Thr Ile Thr Thr
465                 470                 475                 480
Pro Thr Ile Thr Thr Thr Thr Ala Phe Met Ile Ser Pro Lys Lys Gly
                485                 490                 495
Asn Val Thr Ala Thr Arg Val Ala Ile Thr Thr Thr Pro Thr Thr Thr
            500                 505                 510
Ile Thr Thr Thr Ile Ala Gly Thr Tyr Gln Ser Val Thr Asn Asn Thr
        515                 520                 525
Thr Pro Val Val Ser Glu Thr Leu Pro Ser Leu Pro Val Lys Ile Arg
530                 535                 540
Asn Lys Ile Gly Ala Cys Glu Cys Gly Glu Trp Thr Glu Trp Thr Gly
545                 550                 555                 560
Pro Cys Ser Gln Glu Cys Gly Cys Gly Lys Arg Leu Arg Thr Arg
                565                 570                 575
Gln Cys Ser Ser Asp Thr Glu Cys Arg Thr Glu Lys Arg Ala Cys
            580                 585                 590
Ala Phe Lys Phe Ala His Thr Gly Leu Ile Ser Leu Ser Ile Met Glu
        595                 600                 605
Ser Phe Ile Tyr Phe Gly Arg Ala Ala Val Leu Val Tyr Ser Asp Arg
        610                 615                 620
Glu Ile Cys Val Gln His Leu Met Ile Thr Arg Ile His Phe
625                 630                 635

(2) INFORMATION FOR SEQ ID NO:12:

(i) SEQUENCE CHARACTERISTICS:
        (A) LENGTH: 143 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..143

(xi) SEQUENCE DESCRIPTION: SEQ ID NO:12:

GGA TCC TGT GGT TCA TGT TGG GCT TTT TCT GTT ACT GGC AAT ATT GCA    48
Gly Ser Cys Gly Ser Cys Trp Ala Phe Ser Val Thr Gly Asn Ile Ala
  1               5                  10                  15

AGT CTC TGG GCT ATT AAA ACA GGT GAT TTG ATA TCG CTT TCC GAG CAA    96
Ser Leu Trp Ala Ile Lys Thr Gly Asp Leu Ile Ser Leu Ser Glu Gln
             20                  25                  30

GAA TTG ATT GAT TGT GAT GTG GTT GAT GAG GGC TGC AAC GGC GGC TA    143
Glu Leu Ile Asp Cys Asp Val Val Asp Glu Gly Cys Asn Gly Gly
```

```
              35                  40                  45
```

(2) INFORMATION FOR SEQ ID NO:13:

(i) SEQUENCE CHARACTERISTICS:
        (A) LENGTH: 47 amino acids
        (B) TYPE: amino acid
        (D) TOPOLOGY: linear (ii) MOLECULE TYPE: protein (xi) SEQUENCE DESCRIPTION: SEQ ID NO:13:

```
Gly Ser Cys Gly Ser Cys Trp Ala Phe Ser Val Thr Gly Asn Ile Ala
 1               5                  10                  15

Ser Leu Trp Ala Ile Lys Thr Gly Asp Leu Ile Ser Leu Ser Glu Gln
             20                  25                  30

Glu Leu Ile Asp Cys Asp Val Val Asp Glu Gly Cys Asn Gly Gly
             35                  40                  45
```

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 12
        (D) OTHER INFORMATION: /label= INOSINE (ix) FEATURE:
        (A) NAME/KEY: misc_feature
        (B) LOCATION: 15
        (D) OTHER INFORMATION: /label= INOSINE (xi) SEQUENCE DESCRIPTION: SEQ ID NO:14:

ACWCATGAAA TNGSNCAT                                            18

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

AATACGACTC ACTATAG                                             17

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

TGGTATTATA TCACATGAAA TTGGTCATAC                             30

(2) INFORMATION FOR SEQ ID NO:17:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
CCCAATTGTG TACTGTTGAA ATTTATCAC                                29
```

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
CGGGATCCTG TGGWTCATGY TGGGC                                    25
```

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
TANCCNCCRT TRCANCCYTC                                          20
```

(2) INFORMATION FOR SEQ ID NO:20:

(i) SEQUENCE CHARACTERISTICS:
        (A) LENGTH: 689 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

```
TCACATGAAA TTGGTCATAC TTTAGGAATA TTTCATGAGC AAGCACGTCG TGATCAAAAA    60
AATCATATTT TTATTAATTA CAACAATATT CCATCAAGCC GTTGAACAA TTTTTTTCCA    120
TTATCAGAAT ATGAAGCTGA TATGTTTAAT TTACCTTATG ATACAGGATC AGTAATGCAC   180
TATGGTTCAT ACGGATTTGC AAGAAATCCG TATGAACCAA CTATTACAAC ACGTGATAAA   240
TTTCAACAGT ACACAATTGG GCAACGTGAA GGGCCATCAT TTCTGGATTA TGCATCTGTT   300
AAGCTTTATC TACAAACGCA TTAATGATAT TGTTATCAAA TGGATGATAA TTTCAATAAG   360
TATAAACAGC GCTTATCGTT GTACAGAACA ATGTGCTGAT ATGCACTGCG ATCATAATGG   420
TTATCCGGAT CCTAATAATT GCGCGAAATG CTTGTGTCCA GATGGTTTTG CTGGTCGTAC   480
CTGTCAATTT GTTCAATATA CATCTTGCGG AGCTCTCATT AAGGTAAGTA TTGTCTTTTG   540
ACCTCTTCTC TGACTAAAAT ATAAGTTAAG CATATGTATC TTCCGTCTAA TGATTTTCTT   600
GATTTTGATT TGTTCAATGC TCTTCTTGAT AATAATATAA AAATTTTTGA AAATAAAGTT   660
```

```
AACTTTTGGT CAAAAAAAAA AAAAAAAA                                            689

(2) INFORMATION FOR SEQ ID NO:21:

(i) SEQUENCE CHARACTERISTICS:
        (A) LENGTH: 804 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

GATCCTGAGG CAAAATGGCA TCATAATGAA CTATTCATTA ATGATCCAGA TGCATACTAT    60

CAAGGCGATG TCGATTTGTC GGAAAAACAA GCCGAAATTC TAAGCGAACA TTTTAAAAAT   120

GAAATTGCTT TAACAGAGAA AGACGACACA ATAATACGGC GAAAAAGAG CATTGGTCGT    180

GAACCATTTT ACGTAAGATG GAATCATAAA CGTCCCATTA GCTATGAATT TGCGGAAAGT   240

ATTCCATTAG AAACACGTAG AAAAATTCGT TCAGCAATAG CAATGTGGGA AGAACGAACA   300

TGCATACGAT TCCAAGAAAA TGGCCCAAAT GTAGATCGAA TTGAATTTTA CGACGGTGGC   360

GGTTGTTCAA GTTTTGTCGG CCGAACAGGA GGGAATTTCA ATTTCAACAC CAGGATGTGA   420

TATTATTGGT ATTATATCAC ATGAAATTGG TCATACTTTA GGAATATTTC ATGAGCAAGC   480

ACGTCGTGAT CAAAAAAATC ATATTTTTAT TAATTACAAC AATATTCCAT CAAGCCGTTG   540

GAACAATTTT TTTCCATTAT CAGAATATGA AGCTGATATG TTTAATTTAC CTTATGATAC   600

AGGATCAGTA ATGCACTATG GTTCATACGG ATTTGCAAGA AATCCGTATG AACCAACTAT   660

TACAACACGT GATAAATTTC AACAGTACAC AATTGGGCAA CGTGAAGGGC CATCATTTCT   720

GGATTATGCA TCTGATAAAC AGCGCTTATC GTTGTACAGA ACAATGTGCT GATATGCACT   780

GCGATCATAA TGGTTATCCG GATC                                          804

(2) INFORMATION FOR SEQ ID NO:22:

(i) SEQUENCE CHARACTERISTICS:
        (A) LENGTH: 271 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

TGGTATTATA TCACATGAAA TTGGTCATAC TTTAGGAATA TTTCATGAGC AAGCACGTCG    60

TGATCAAAAA AATCATATTT TTATTAATTA CAACAATATT CCATCAAGCC GTTGGAACAA   120

TTTTTTTCCA TTATCAGAAT ATGAAGCTGA TATGTTTAAT TTACCTTATG ATACAGGATC   180

AGTAATGCAC TATGGTTCAT ACGGATTTGC AAGAAATCCG TATGAACCAA CTATTACAAC   240

ACGTGATAAA TTTCAACAGT ACACAATTGG G                                  271

(2) INFORMATION FOR SEQ ID NO:23:

(i) SEQUENCE CHARACTERISTICS:
        (A) LENGTH: 142 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
```

(B) LOCATION: 3..140

(xi) SEQUENCE DESCRIPTION: SEQ ID NO:23:

```
GA TCC TGT GGT TCA TGT TGG GCT TTT TCT GTT ACT GGC AAT ATT GCA        47
   Ser Cys Gly Ser Cys Trp Ala Phe Ser Val Thr Gly Asn Ile Ala
    1               5                  10                  15

AGT CTC TGG GCT ATT AAA ACA GGT GAT TTG ATA TCG CTT TCC GAG CAA       95
Ser Leu Trp Ala Ile Lys Thr Gly Asp Leu Ile Ser Leu Ser Glu Gln
            20                  25                  30

GAA TTG ATT GAT TGT GAT GTG GTT GAT GAG GGC TGC AAC GGC GGC          140
Glu Leu Ile Asp Cys Asp Val Val Asp Glu Gly Cys Asn Gly Gly
        35                  40                  45

TA                                                                   142
```

(2) INFORMATION FOR SEQ ID NO:24:

(i) SEQUENCE CHARACTERISTICS:
        (A) LENGTH: 46 amino acids
        (B) TYPE: amino acid
        (D) TOPOLOGY: linear (ii) MOLECULE TYPE: protein (xi) SEQUENCE DESCRIPTION: SEQ ID NO:24:

```
Ser Cys Gly Ser Cys Trp Ala Phe Ser Val Thr Gly Asn Ile Ala Ser
 1               5                  10                  15

Leu Trp Ala Ile Lys Thr Gly Asp Leu Ile Ser Leu Ser Glu Gln Glu
            20                  25                  30

Leu Ile Asp Cys Asp Val Val Asp Glu Gly Cys Asn Gly Gly
        35                  40                  45
```

(2) INFORMATION FOR SEQ ID NO:25:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:25:

GTCGGATCCG CAGGAGGGAA TTTCAATTTC AACA                      34

(2) INFORMATION FOR SEQ ID NO:26:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:26:

TCAAGATCTA ATCCAGAAAT GATGGCCCTT CACG                      34

(2) INFORMATION FOR SEQ ID NO:27:

(i) SEQUENCE CHARACTERISTICS:
        (A) LENGTH: 19 base pairs
        (B) TYPE: nucleic acid
        (C) STRANDEDNESS: single
        (D) TOPOLOGY: linear

```
    (ii) MOLECULE TYPE: other nucleic acid
         (A) DESCRIPTION: /desc = "primer"

(xi) SEQUENCE DESCRIPTION: SEQ ID NO:27:

GGAAACAGCT ATGACCATG                                                  19

(2) INFORMATION FOR SEQ ID NO:28:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "primer"

(xi) SEQUENCE DESCRIPTION: SEQ ID NO:28:

GTAAAACGAC GGCCAGT                                                    17

(2) INFORMATION FOR SEQ ID NO:29:

(i) SEQUENCE CHARACTERISTICS:
        (A) LENGTH: 2292 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: misc_feature
         (B) LOCATION: 1459
         (D) OTHER INFORMATION: /note= "1459:S=C or G;
             aa463:Xaa=Alanine or Glycine"

(xi) SEQUENCE DESCRIPTION: SEQ ID NO:29:

TAGATTTCGA TTCGTCTTTG TTAATTCATC TTCGTCAGAT TTATTAGAGA AAAATAAAAA      60

TTTTGATCGC AATGAAGCAG GTTATCATCT TCCTCAGCT TTTCATTTGT TTCATTGTTC     120

AGTCAGTGGA AAATTATCGA ACGCAGAAAG CATCACGAAA TACGTTAGAT CACATCAAAC    180

AACTTATCAC CTTGAACGTA CAAAGAGAGA TTGGAAACAT AGATGATAAG ACATTAGCTG    240

ATGAAATAGT ATTACAACGA CGGGATCCTG AGGCAAAATG GCATCATAAT GAACTATTCA    300

TTAATGATCC AGATGCATAC TATCAAGGCG ATGTCGATTT GTCGGAAAAA CAAGCCGAAA    360

TTCTAAGCGA ACATTTTAAA AATGAAATTG CTTTAACAGA GAAAGACGAC ACAATAATAC    420

GGCGAAAAAA GAGCATTGGT CGTGAACCAT TTTACGTAAG ATGGAATCAT AAACGTCCCA    480

TTAGCTATGA ATTTGCGGAA AGTATTCCAT TAGAAACACG TAGAAAAATT CGTTCAGCAA    540

TAGCAATGTG GGAAGAACGA ACATGCATAC GATTCCAAGA AAATGGCCCA AATGTTGATC    600

GAATTGAATT TTACGACGGT GGCGGTTGTT CAAGTTTTGT CGGCCGAACA GGAGGCACGC    660

AAGGAATTTC AATTTCAACA CCAGGATGTG ATATTATTGG TATTATATCA CATGAAATTG    720

GTCATACTTT AGGAATATTT CATGAGCAAG CACGTCGTGA TCAAAAAAAT CATATTTTTA    780

TTAATTACAA CAATATTCCA TCAAGCCGTT GGAACAATTT TTTTCCATTA TCAGAATATG    840

AAGCTGATAT GTTTAATTTA CCTTATGATA CAGGATCAGT AATGCACTAT GGTTCATACG    900

GATTTGCAAG AAATCCGTAT GAACCAACTA TTACAACACG TGATAAATTT CAACAGTACA    960

CAATTGGGCA ACGTGAAGGG CCATCATTTC TGGATTATGC ATCTATAAAC AGCGCTTATC   1020

GTTGTACAGA ACAATGTGCT GATATGCACT GCGATCATAA TGGTTATCCG GATCCTAATA   1080
```

-continued

```
ATTGCGCGAA ATGCTTGTGT CCAGATGGTT TTGCTGGTCG TACCTGTCAA TTTGTTCAAT    1140

ATACATCTTG CGGAGCTCTC ATTAAGGCGA GGAAAATGCC TGTTACGATT TCGAGCCCAA    1200

ATTATCCAAA CTTCTTCAAT GTTGGTGATC AATGTATTTG GTTGCTTACA GCTCCACGCG    1260

GTGGATTCGT AAATTTGCAG TTTGTTGAAC AATTTCAATT ACAATGTGAA GATACGTGTG    1320

ATAAATCCTA TGTAGAAGTG AAAGCTGACG CTGATTTTCG ACCTACTGGA TATCGATTTT    1380

GTTGTTCGCG AGTGCCACGT CATATTTTTC AATCTGCGAC AAACGAGATG GTAGTAATAT    1440

TTCGCGGTTT TGGTGATGCG GGAAATGGCT TTAAAGCTAA AATTTGGTCA AACGTAGATG    1500

ATGATATAGC TAATACAATT GTAACAACTG AAATGGCAAA AATTTCGGAA AAAATACCGA    1560

AGCTAACAGT TCCAATAGTT AAAACTATTA CCACTCCTAC AATAACAACT ACTACTGCTT    1620

TCATGATATC ACCCAAGAAA GGCAATGTCA CCGCCACGAG AGTTGCTATC ACTACTACGC    1680

CGACTACTAC AATTACTACG ACTATTGCCG GTACGGTACC AATCACCGTA ACTAATAATA    1740

CTACACCTGT AGTAAGTGAA ACTTTACCAT CATTGCCAGT CAAGATTCGA ACAAAATAG    1800

GTGCATGCGA ATGTGGTGAA TGGACAGAAT GGACAGGTCC ATGCTCTCAA GAATGTGGCG    1860

GTTGCGGAAA ACGTCTTCGA ACACGTCAGT GTTCATCAGA TACGGAATGT AGAACAGAAG    1920

AAAAACGTGC GTGTGCTTTT AAAGTTTGCC CATACGGGAC TAATTTCCTT ATCAATAATG    1980

GAGAGTTTCA TATACTTTGG AAGGGCTGCT GTGTTGGTCT ATTCCGATCG GGAGATATGT    2040

GTTCAGCACT TGATGATAAC GAGAATCCAT TTCTGAAATT TCTAGAATCA CTGTTGAACA    2100

TGCAAGATTC TCGAAAAAAC GATAATTTGC CTGACTCGAA AAAGAAGTGA TTGAATGATT    2160

CGATAATATT GATTAATAAA ACGGGTTGTA TTCTCGTCAT AGAGTATCCG TTGATGTTTT    2220

TATCCAAAAA ATTCTCTTGC TTTTAATTAT TGTGAATAAA ACTTTTGTTT ACCCAAAAAA    2280

AAAAAAAAAA AA                                                        2292
```

(2) INFORMATION FOR SEQ ID NO:30:

(i) SEQUENCE CHARACTERISTICS:
        (A) LENGTH: 2076 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2076

(xi) SEQUENCE DESCRIPTION: SEQ ID NO:30:

```
ATG AAG CAG GTT ATC ATC TTT CCT CAG CTT TTC ATT TGT TTC ATT GTT           48
Met Lys Gln Val Ile Ile Phe Pro Gln Leu Phe Ile Cys Phe Ile Val
  1               5                  10                  15

CAG TCA GTG GAA AAT TAT CGA ACG CAG AAA GCA TCA CGA AAT ACG TTA           96
Gln Ser Val Glu Asn Tyr Arg Thr Gln Lys Ala Ser Arg Asn Thr Leu
             20                  25                  30

GAT CAC ATC AAA CAA CTT ATC ACC TTG AAC GTA CAA AGA GAG ATT GGA          144
Asp His Ile Lys Gln Leu Ile Thr Leu Asn Val Gln Arg Glu Ile Gly
         35                  40                  45

AAC ATA GAT GAT AAG ACA TTA GCT GAT GAA ATA GTA TTA CAA CGA CGG          192
Asn Ile Asp Asp Lys Thr Leu Ala Asp Glu Ile Val Leu Gln Arg Arg
     50                  55                  60

GAT CCT GAG GCA AAA TGG CAT CAT AAT GAA CTA TTC ATT AAT GAT CCA          240
Asp Pro Glu Ala Lys Trp His His Asn Glu Leu Phe Ile Asn Asp Pro
 65                  70                  75                  80
```

```
GAT GCA TAC TAT CAA GGC GAT GTC GAT TTG TCG GAA AAA CAA GCC GAA      288
Asp Ala Tyr Tyr Gln Gly Asp Val Asp Leu Ser Glu Lys Gln Ala Glu
                    85                  90                  95

ATT CTA AGC GAA CAT TTT AAA AAT GAA ATT GCT TTA ACA GAG AAA GAC      336
Ile Leu Ser Glu His Phe Lys Asn Glu Ile Ala Leu Thr Glu Lys Asp
            100                 105                 110

GAC ACA ATA ATA CGG CGA AAA AAG AGC ATT GGT CGT GAA CCA TTT TAC      384
Asp Thr Ile Ile Arg Arg Lys Lys Ser Ile Gly Arg Glu Pro Phe Tyr
        115                 120                 125

GTA AGA TGG AAT CAT AAA CGT CCC ATT AGC TAT GAA TTT GCG GAA AGT      432
Val Arg Trp Asn His Lys Arg Pro Ile Ser Tyr Glu Phe Ala Glu Ser
    130                 135                 140

ATT CCA TTA GAA ACA CGT AGA AAA ATT CGT TCA GCA ATA GCA ATG TGG      480
Ile Pro Leu Glu Thr Arg Arg Lys Ile Arg Ser Ala Ile Ala Met Trp
145                 150                 155                 160

GAA GAA CGA ACA TGC ATA CGA TTC CAA GAA AAT GGC CCA AAT GTT GAT      528
Glu Glu Arg Thr Cys Ile Arg Phe Gln Glu Asn Gly Pro Asn Val Asp
                165                 170                 175

CGA ATT GAA TTT TAC GAC GGT GGC GGT TGT TCA AGT TTT GTC GGC CGA      576
Arg Ile Glu Phe Tyr Asp Gly Gly Gly Cys Ser Ser Phe Val Gly Arg
            180                 185                 190

ACA GGA GGC ACG CAA GGA ATT TCA ATT TCA ACA CCA GGA TGT GAT ATT      624
Thr Gly Gly Thr Gln Gly Ile Ser Ile Ser Thr Pro Gly Cys Asp Ile
        195                 200                 205

ATT GGT ATT ATA TCA CAT GAA ATT GGT CAT ACT TTA GGA ATA TTT CAT      672
Ile Gly Ile Ile Ser His Glu Ile Gly His Thr Leu Gly Ile Phe His
    210                 215                 220

GAG CAA GCA CGT CGT GAT CAA AAA AAT CAT ATT TTT ATT AAT TAC AAC      720
Glu Gln Ala Arg Arg Asp Gln Lys Asn His Ile Phe Ile Asn Tyr Asn
225                 230                 235                 240

AAT ATT CCA TCA AGC CGT TGG AAC AAT TTT TTT CCA TTA TCA GAA TAT      768
Asn Ile Pro Ser Ser Arg Trp Asn Asn Phe Phe Pro Leu Ser Glu Tyr
                245                 250                 255

GAA GCT GAT ATG TTT AAT TTA CCT TAT GAT ACA GGA TCA GTA ATG CAC      816
Glu Ala Asp Met Phe Asn Leu Pro Tyr Asp Thr Gly Ser Val Met His
            260                 265                 270

TAT GGT TCA TAC GGA TTT GCA AGA AAT CCG TAT GAA CCA ACT ATT ACA      864
Tyr Gly Ser Tyr Gly Phe Ala Arg Asn Pro Tyr Glu Pro Thr Ile Thr
        275                 280                 285

ACA CGT GAT AAA TTT CAA CAG TAC ACA ATT GGG CAA CGT GAA GGG CCA      912
Thr Arg Asp Lys Phe Gln Gln Tyr Thr Ile Gly Gln Arg Glu Gly Pro
    290                 295                 300

TCA TTT CTG GAT TAT GCA TCT ATA AAC AGC GCT TAT CGT TGT ACA GAA      960
Ser Phe Leu Asp Tyr Ala Ser Ile Asn Ser Ala Tyr Arg Cys Thr Glu
305                 310                 315                 320

CAA TGT GCT GAT ATG CAC TGC GAT CAT AAT GGT TAT CCG GAT CCT AAT     1008
Gln Cys Ala Asp Met His Cys Asp His Asn Gly Tyr Pro Asp Pro Asn
                325                 330                 335

AAT TGC GCG AAA TGC TTG TGT CCA GAT GGT TTT GCT GGT CGT ACC TGT     1056
Asn Cys Ala Lys Cys Leu Cys Pro Asp Gly Phe Ala Gly Arg Thr Cys
            340                 345                 350

CAA TTT GTT CAA TAT ACA TCT TGC GGA GCT CTC ATT AAG GCG AGG AAA     1104
Gln Phe Val Gln Tyr Thr Ser Cys Gly Ala Leu Ile Lys Ala Arg Lys
        355                 360                 365

ATG CCT GTT ACG ATT TCG AGC CCA AAT TAT CCA AAC TTC TTC AAT GTT     1152
Met Pro Val Thr Ile Ser Ser Pro Asn Tyr Pro Asn Phe Phe Asn Val
    370                 375                 380

GGT GAT CAA TGT ATT TGG TTG CTT ACA GCT CCA CGC GGT GGA TTC GTA     1200
Gly Asp Gln Cys Ile Trp Leu Leu Thr Ala Pro Arg Gly Gly Phe Val
385                 390                 395                 400
```

```
AAT TTG CAG TTT GTT GAA CAA TTT CAA TTA CAA TGT GAA GAT ACG TGT      1248
Asn Leu Gln Phe Val Glu Gln Phe Gln Leu Gln Cys Glu Asp Thr Cys
                405                 410                 415

GAT AAA TCC TAT GTA GAA GTG AAA GCT GAC GCT GAT TTT CGA CCT ACT      1296
Asp Lys Ser Tyr Val Glu Val Lys Ala Asp Ala Asp Phe Arg Pro Thr
            420                 425                 430

GGA TAT CGA TTT TGT TGT TCG CGA GTG CCA CGT CAT ATT TTT CAA TCT      1344
Gly Tyr Arg Phe Cys Cys Ser Arg Val Pro Arg His Ile Phe Gln Ser
            435                 440                 445

GCG ACA AAC GAG ATG GTA GTA ATA TTT CGC GGT TTT GGT GAT GCG GGA      1392
Ala Thr Asn Glu Met Val Val Ile Phe Arg Gly Phe Gly Asp Ala Gly
            450                 455                 460

AAT GGC TTT AAA GCT AAA ATT TGG TCA AAC GTA GAT GAT GAT ATA GCT      1440
Asn Gly Phe Lys Ala Lys Ile Trp Ser Asn Val Asp Asp Asp Ile Ala
465                 470                 475                 480

AAT ACA ATT GTA ACA ACT GAA ATG GCA AAA ATT TCG GAA AAA ATA CCG      1488
Asn Thr Ile Val Thr Thr Glu Met Ala Lys Ile Ser Glu Lys Ile Pro
            485                 490                 495

AAG CTA ACA GTT CCA ATA GTT AAA ACT ATT ACC ACT CCT ACA ATA ACA      1536
Lys Leu Thr Val Pro Ile Val Lys Thr Ile Thr Thr Pro Thr Ile Thr
            500                 505                 510

ACT ACT ACT GCT TTC ATG ATA TCA CCC AAG AAA GGC AAT GTC ACC GCC      1584
Thr Thr Thr Ala Phe Met Ile Ser Pro Lys Lys Gly Asn Val Thr Ala
            515                 520                 525

ACG AGA GTT GCT ATC ACT ACT ACG CCG ACT ACT ACA ATT ACT ACG ACT      1632
Thr Arg Val Ala Ile Thr Thr Thr Pro Thr Thr Thr Ile Thr Thr Thr
            530                 535                 540

ATT GCC GGT ACG GTA CCA ATC ACC GTA ACT AAT AAT ACT ACA CCT GTA      1680
Ile Ala Gly Thr Val Pro Ile Thr Val Thr Asn Asn Thr Thr Pro Val
545                 550                 555                 560

GTA AGT GAA ACT TTA CCA TCA TTG CCA GTC AAG ATT CGA AAC AAA ATA      1728
Val Ser Glu Thr Leu Pro Ser Leu Pro Val Lys Ile Arg Asn Lys Ile
            565                 570                 575

GGT GCA TGC GAA TGT GGT GAA TGG ACA GAA TGG ACA GGT CCA TGC TCT      1776
Gly Ala Cys Glu Cys Gly Glu Trp Thr Glu Trp Thr Gly Pro Cys Ser
            580                 585                 590

CAA GAA TGT GGC GGT TGC GGA AAA CGT CTT CGA ACA CGT CAG TGT TCA      1824
Gln Glu Cys Gly Gly Cys Gly Lys Arg Leu Arg Thr Arg Gln Cys Ser
            595                 600                 605

TCA GAT ACG GAA TGT AGA ACA GAA GAA AAA CGT GCG TGT GCT TTT AAA      1872
Ser Asp Thr Glu Cys Arg Thr Glu Glu Lys Arg Ala Cys Ala Phe Lys
            610                 615                 620

GTT TGC CCA TAC GGG ACT AAT TTC CTT ATC AAT AAT GGA GAG TTT CAT      1920
Val Cys Pro Tyr Gly Thr Asn Phe Leu Ile Asn Asn Gly Glu Phe His
625                 630                 635                 640

ATA CTT TGG AAG GGC TGC TGT GTT GGT CTA TTC CGA TCG GGA GAT ATG      1968
Ile Leu Trp Lys Gly Cys Cys Val Gly Leu Phe Arg Ser Gly Asp Met
            645                 650                 655

TGT TCA GCA CTT GAT GAT AAC GAG AAT CCA TTT CTG AAA TTT CTA GAA      2016
Cys Ser Ala Leu Asp Asp Asn Glu Asn Pro Phe Leu Lys Phe Leu Glu
            660                 665                 670

TCA CTG TTG AAC ATG CAA GAT TCT CGA AAA AAC GAT AAT TTG CCT GAC      2064
Ser Leu Leu Asn Met Gln Asp Ser Arg Lys Asn Asp Asn Leu Pro Asp
            675                 680                 685

TCG AAA AAG AAG                                                       2076
Ser Lys Lys Lys
    690
```

(2) INFORMATION FOR SEQ ID NO:31:

(i) SEQUENCE CHARACTERISTICS:
    (A) LENGTH: 692 amino acids
    (B) TYPE: amino acid
    (D) TOPOLOGY: linear (ii) MOLECULE TYPE: protein (xi) SEQUENCE DESCRIPTION: SEQ ID NO:31:

```
Met Lys Gln Val Ile Ile Phe Pro Gln Leu Phe Ile Cys Phe Ile Val
 1               5                  10                  15

Gln Ser Val Glu Asn Tyr Arg Thr Gln Lys Ala Ser Arg Asn Thr Leu
            20                  25                  30

Asp His Ile Lys Gln Leu Ile Thr Leu Asn Val Gln Arg Glu Ile Gly
        35                  40                  45

Asn Ile Asp Asp Lys Thr Leu Ala Asp Glu Ile Val Leu Gln Arg Arg
 50                  55                  60

Asp Pro Glu Ala Lys Trp His His Asn Glu Leu Phe Ile Asn Asp Pro
 65                  70                  75                  80

Asp Ala Tyr Tyr Gln Gly Asp Val Asp Leu Ser Glu Lys Gln Ala Glu
            85                  90                  95

Ile Leu Ser Glu His Phe Lys Asn Glu Ile Ala Leu Thr Glu Lys Asp
            100                 105                 110

Asp Thr Ile Ile Arg Arg Lys Lys Ser Ile Gly Arg Glu Pro Phe Tyr
        115                 120                 125

Val Arg Trp Asn His Lys Arg Pro Ile Ser Tyr Glu Phe Ala Glu Ser
130                 135                 140

Ile Pro Leu Glu Thr Arg Arg Lys Ile Arg Ser Ala Ile Ala Met Trp
145                 150                 155                 160

Glu Glu Arg Thr Cys Ile Arg Phe Gln Glu Asn Gly Pro Asn Val Asp
            165                 170                 175

Arg Ile Glu Phe Tyr Asp Gly Gly Cys Ser Ser Phe Val Gly Arg
            180                 185                 190

Thr Gly Gly Thr Gln Gly Ile Ser Ile Ser Thr Pro Gly Cys Asp Ile
        195                 200                 205

Ile Gly Ile Ile Ser His Glu Ile Gly His Thr Leu Gly Ile Phe His
210                 215                 220

Glu Gln Ala Arg Arg Asp Gln Lys Asn His Ile Phe Ile Asn Tyr Asn
225                 230                 235                 240

Asn Ile Pro Ser Ser Arg Trp Asn Asn Phe Phe Pro Leu Ser Glu Tyr
            245                 250                 255

Glu Ala Asp Met Phe Asn Leu Pro Tyr Asp Thr Gly Ser Val Met His
            260                 265                 270

Tyr Gly Ser Tyr Gly Phe Ala Arg Asn Pro Tyr Glu Pro Thr Ile Thr
        275                 280                 285

Thr Arg Asp Lys Phe Gln Gln Tyr Thr Ile Gly Gln Arg Glu Gly Pro
 290                 295                 300

Ser Phe Leu Asp Tyr Ala Ser Ile Asn Ser Ala Tyr Arg Cys Thr Glu
305                 310                 315                 320

Gln Cys Ala Asp Met His Cys Asp His Asn Gly Tyr Pro Asp Pro Asn
            325                 330                 335

Asn Cys Ala Lys Cys Leu Cys Pro Asp Gly Phe Ala Gly Arg Thr Cys
            340                 345                 350

Gln Phe Val Gln Tyr Thr Ser Cys Gly Ala Leu Ile Lys Ala Arg Lys
        355                 360                 365
```

```
Met Pro Val Thr Ile Ser Ser Pro Asn Tyr Pro Asn Phe Phe Asn Val
    370                 375                 380
Gly Asp Gln Cys Ile Trp Leu Leu Thr Ala Pro Arg Gly Gly Phe Val
385                 390                 395                 400
Asn Leu Gln Phe Val Glu Gln Phe Gln Leu Gln Cys Glu Asp Thr Cys
                405                 410                 415
Asp Lys Ser Tyr Val Glu Val Lys Ala Asp Ala Asp Phe Arg Pro Thr
                420                 425                 430
Gly Tyr Arg Phe Cys Cys Ser Arg Val Pro Arg His Ile Phe Gln Ser
            435                 440                 445
Ala Thr Asn Glu Met Val Val Ile Phe Arg Gly Phe Gly Asp Ala Gly
    450                 455                 460
Asn Gly Phe Lys Ala Lys Ile Trp Ser Asn Val Asp Asp Asp Ile Ala
465                 470                 475                 480
Asn Thr Ile Val Thr Thr Glu Met Ala Lys Ile Ser Glu Lys Ile Pro
                485                 490                 495
Lys Leu Thr Val Pro Ile Val Lys Thr Ile Thr Thr Pro Thr Ile Thr
                500                 505                 510
Thr Thr Thr Ala Phe Met Ile Ser Pro Lys Lys Gly Asn Val Thr Ala
            515                 520                 525
Thr Arg Val Ala Ile Thr Thr Thr Pro Thr Thr Thr Ile Thr Thr Thr
    530                 535                 540
Ile Ala Gly Thr Val Pro Ile Thr Val Thr Asn Asn Thr Thr Pro Val
545                 550                 555                 560
Val Ser Glu Thr Leu Pro Ser Leu Pro Val Lys Ile Arg Asn Lys Ile
                565                 570                 575
Gly Ala Cys Glu Cys Gly Glu Trp Thr Glu Trp Thr Gly Pro Cys Ser
            580                 585                 590
Gln Glu Cys Gly Gly Cys Gly Lys Arg Leu Arg Thr Arg Gln Cys Ser
            595                 600                 605
Ser Asp Thr Glu Cys Arg Thr Glu Glu Lys Arg Ala Cys Ala Phe Lys
    610                 615                 620
Val Cys Pro Tyr Gly Thr Asn Phe Leu Ile Asn Asn Gly Glu Phe His
625                 630                 635                 640
Ile Leu Trp Lys Gly Cys Cys Val Gly Leu Phe Arg Ser Gly Asp Met
                645                 650                 655
Cys Ser Ala Leu Asp Asp Asn Glu Asn Pro Phe Leu Lys Phe Leu Glu
                660                 665                 670
Ser Leu Leu Asn Met Gln Asp Ser Arg Lys Asn Asp Asn Leu Pro Asp
            675                 680                 685
Ser Lys Lys Lys
    690
```

(2) INFORMATION FOR SEQ ID NO:32:

(i) SEQUENCE CHARACTERISTICS:
        (A) LENGTH: 2032 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

```
TCAGTCAGTG GAAAATTATC GAACGCAGAA AGCATCACGA AATACGTTAG ATCACATCAA    60
ACAACTTATC ACCTTGAACG TACAAAGAGA GATTGGAAAC ATAGATGATA AGACATTAGC   120
```

-continued

```
TGATGAAATA GTATTACAAC GACGGGATCC TGAGGCAAAA TGGCATCATA ATGAACTATT      180

CATTAATGAT CCAGATGCAT ACTATCAAGG CGATGTCGAT TTGTCGGAAA ACAAGCCGA       240

AATTCTAAGC GAACATTTTA AAAATGAAAT TGCTTTAACA GAGAAAGACG ACACAATAAT      300

ACGGCGAAAA AAGAGCATTG GTCGTGAACC ATTTTACGTA AGATGGAATC ATAAACGTCC      360

CATTAGCTAT GAATTTGCGG AAAGTATTCC ATTAGAAACA CGTAGAAAAA TTCGTTCAGC      420

AATAGCAATG TGGGAAGAAC GAACATGCAT ACGATTCCAA GAAAATGGCC CAAACGTAGA      480

TCGAATTGTA TTTAACGACG GTGGCGGTTG TTCAAGTTTT GTCGGCCGAA CAGGAGGCAC      540

GCCAGGAATT TCAATTTCAA CACCAGGATG TGATATTATT GGTATTATAT CACATGAAAT      600

TGGTCATACT TTAGGAATAT TTCATGAGCA AGCACGTCGT GATCAAAAAA ATCATATTTT      660

TATTAATTAC AACAATATTC CATCAAGCCG TTGGAACAAT TTTTTTCCAT TATCAGAATA      720

TGAAGCTGAT ATGTTTAATT TACCTTATGA TACAGGATCA GTAATGCACT ATGGTTCATA      780

CGGATTTGCA AGAAATCCGT ATGAACCAAC TATTACAACA CGTGATAAAT TCAACAGTA       840

CACAATTGGG CAACGTGAAG GGCCATCATT TCTGGATTAT GCATCTATAA ACAGCGCTTA      900

TCGTTGTACA GAACAATGTG CTGATATGCA CTGCGATCAT AATGGTTATC CGGATCCTAA      960

TAATTGCGCG AAATGCTTGT GTCCAGATGG TTTTGCTGGT CGTACCTGTC AATTTGTTCA     1020

ATATACATCT TGCGGAGCTC TCATTAAGGC GAGGAAAATG CCTGTTACGA TTTCGAGCCC     1080

AAATTATCCA AACTTCTTCA ATGTTGGTGA TCAATGTATT TGGTTGCTTA CAGCTCCACG     1140

CGGTGGATTC GTAAATTTGC AGTTTGTTGA ACAATTTCAA TTACAATGTG AAGATACGTG     1200

TGATAAATCC TATGTAGAAG TGAAAGCTGA CGCTGATTTT CGACCTACTG GATATCGATT     1260

TTGTTGTTCG CGAGTGCCAC GTCATATTTT TCAATCTGCG ACAAACGAGA TGGTAGTAAT     1320

ATTTCGCGGT TTTGGTGGTG CGGGAAATGG CTTTAAAGCT AAAATTTGGT CAAACGTAGA     1380

TGATGATATA GCTAATACAA TTGTAACAAC TGAAATGGCA AAAATTTCGG AAAAAATACC     1440

GAAGCTAACA GTTCCAATAG TTAAAACTAT TACCACTCCT ACAATAACAA CTACTACTGC     1500

TTTCATGATA TCACCCAAGA AAGGCAATGT CACCGCCACG AGAGTTGCTA TCACTACTAC     1560

GCCGACTACT ACAATTACTA CGACTATTGC CGGTACGGTA CCAATCACCG TAACTAATAA     1620

TACTACCCCT GTAGTAAGTG AAACTTTACC ATCATTGCCA GTCAAGATTC GAAACAAAAT     1680

AGGTGCATGC GAATGTGGTG AATGGACAGA ATGGACAGGT CCATGCTCTC AAGAATGTGG     1740

CGGTTGCGGA AAACGTCTTC GAACACGTCA GTGTTCATCA GATACGGAAT GTAGAACAGA     1800

AGAAAAACGT GCGTGTGCTT TTAAAGTTTG CCCATACGGG ACTAATTTCC TTATCAATAA     1860

TGGAGAGTTT CATATACTTT GGAAGGGCTG CTGTGTTGGT CTATTCCGAT CGGGAGATAT     1920

GTGTTCAGCA CTTGATGATA ACGAGAATCC ATTTCTGAAA TTTCTAGAAT CACTGTTGAA     1980

CATGCAAGAT TCTCGAAAAA ACGATAATTT GCCTGACTCG AAAAGAAGT GA              2032
```

(2) INFORMATION FOR SEQ ID NO:33:

(i) SEQUENCE CHARACTERISTICS:
        (A) LENGTH: 2028 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2028

(xi) SEQUENCE DESCRIPTION: SEQ ID NO:33:

```
CAG TCA GTG GAA AAT TAT CGA ACG CAG AAA GCA TCA CGA AAT ACG TTA        48
Gln Ser Val Glu Asn Tyr Arg Thr Gln Lys Ala Ser Arg Asn Thr Leu
 1               5                  10                  15

GAT CAC ATC AAA CAA CTT ATC ACC TTG AAC GTA CAA AGA GAG ATT GGA        96
Asp His Ile Lys Gln Leu Ile Thr Leu Asn Val Gln Arg Glu Ile Gly
                 20                  25                  30

AAC ATA GAT GAT AAG ACA TTA GCT GAT GAA ATA GTA TTA CAA CGA CGG       144
Asn Ile Asp Asp Lys Thr Leu Ala Asp Glu Ile Val Leu Gln Arg Arg
             35                  40                  45

GAT CCT GAG GCA AAA TGG CAT CAT AAT GAA CTA TTC ATT AAT GAT CCA       192
Asp Pro Glu Ala Lys Trp His His Asn Glu Leu Phe Ile Asn Asp Pro
 50                  55                  60

GAT GCA TAC TAT CAA GGC GAT GTC GAT TTG TCG GAA AAA CAA GCC GAA       240
Asp Ala Tyr Tyr Gln Gly Asp Val Asp Leu Ser Glu Lys Gln Ala Glu
 65                  70                  75                  80

ATT CTA AGC GAA CAT TTT AAA AAT GAA ATT GCT TTA ACA GAG AAA GAC       288
Ile Leu Ser Glu His Phe Lys Asn Glu Ile Ala Leu Thr Glu Lys Asp
                 85                  90                  95

GAC ACA ATA ATA CGG CGA AAA AAG AGC ATT GGT CGT GAA CCA TTT TAC       336
Asp Thr Ile Ile Arg Arg Lys Lys Ser Ile Gly Arg Glu Pro Phe Tyr
             100                 105                 110

GTA AGA TGG AAT CAT AAA CGT CCC ATT AGC TAT GAA TTT GCG GAA AGT       384
Val Arg Trp Asn His Lys Arg Pro Ile Ser Tyr Glu Phe Ala Glu Ser
         115                 120                 125

ATT CCA TTA GAA ACA CGT AGA AAA ATT CGT TCA GCA ATA GCA ATG TGG       432
Ile Pro Leu Glu Thr Arg Arg Lys Ile Arg Ser Ala Ile Ala Met Trp
 130                 135                 140

GAA GAA CGA ACA TGC ATA CGA TTC CAA GAA AAT GGC CCA AAC GTA GAT       480
Glu Glu Arg Thr Cys Ile Arg Phe Gln Glu Asn Gly Pro Asn Val Asp
145                 150                 155                 160

CGA ATT GTA TTT AAC GAC GGT GGC GGT TGT TCA AGT TTT GTC GGC CGA       528
Arg Ile Val Phe Asn Asp Gly Gly Gly Cys Ser Ser Phe Val Gly Arg
                 165                 170                 175

ACA GGA GGC ACG CCA GGA ATT TCA ATT TCA ACA CCA GGA TGT GAT ATT       576
Thr Gly Gly Thr Pro Gly Ile Ser Ile Ser Thr Pro Gly Cys Asp Ile
             180                 185                 190

ATT GGT ATT ATA TCA CAT GAA ATT GGT CAT ACT TTA GGA ATA TTT CAT       624
Ile Gly Ile Ile Ser His Glu Ile Gly His Thr Leu Gly Ile Phe His
         195                 200                 205

GAG CAA GCA CGT CGT GAT CAA AAA AAT CAT ATT TTT ATT AAT TAC AAC       672
Glu Gln Ala Arg Arg Asp Gln Lys Asn His Ile Phe Ile Asn Tyr Asn
 210                 215                 220

AAT ATT CCA TCA AGC CGT TGG AAC AAT TTT TTT CCA TTA TCA GAA TAT       720
Asn Ile Pro Ser Ser Arg Trp Asn Asn Phe Phe Pro Leu Ser Glu Tyr
225                 230                 235                 240

GAA GCT GAT ATG TTT AAT TTA CCT TAT GAT ACA GGA TCA GTA ATG CAC       768
Glu Ala Asp Met Phe Asn Leu Pro Tyr Asp Thr Gly Ser Val Met His
                 245                 250                 255

TAT GGT TCA TAC GGA TTT GCA AGA AAT CCG TAT GAA CCA ACT ATT ACA       816
Tyr Gly Ser Tyr Gly Phe Ala Arg Asn Pro Tyr Glu Pro Thr Ile Thr
             260                 265                 270

ACA CGT GAT AAA TTT CAA CAG TAC ACA ATT GGG CAA CGT GAA GGG CCA       864
Thr Arg Asp Lys Phe Gln Gln Tyr Thr Ile Gly Gln Arg Glu Gly Pro
         275                 280                 285

TCA TTT CTG GAT TAT GCA TCT ATA AAC AGC GCT TAT CGT TGT ACA GAA       912
Ser Phe Leu Asp Tyr Ala Ser Ile Asn Ser Ala Tyr Arg Cys Thr Glu
 290                 295                 300
```

```
CAA TGT GCT GAT ATG CAC TGC GAT CAT AAT GGT TAT CCG GAT CCT AAT          960
Gln Cys Ala Asp Met His Cys Asp His Asn Gly Tyr Pro Asp Pro Asn
305                 310                 315                 320

AAT TGC GCG AAA TGC TTG TGT CCA GAT GGT TTT GCT GGT CGT ACC TGT         1008
Asn Cys Ala Lys Cys Leu Cys Pro Asp Gly Phe Ala Gly Arg Thr Cys
                325                 330                 335

CAA TTT GTT CAA TAT ACA TCT TGC GGA GCT CTC ATT AAG GCG AGG AAA         1056
Gln Phe Val Gln Tyr Thr Ser Cys Gly Ala Leu Ile Lys Ala Arg Lys
            340                 345                 350

ATG CCT GTT ACG ATT TCG AGC CCA AAT TAT CCA AAC TTC TTC AAT GTT         1104
Met Pro Val Thr Ile Ser Ser Pro Asn Tyr Pro Asn Phe Phe Asn Val
        355                 360                 365

GGT GAT CAA TGT ATT TGG TTG CTT ACA GCT CCA CGC GGT GGA TTC GTA         1152
Gly Asp Gln Cys Ile Trp Leu Leu Thr Ala Pro Arg Gly Gly Phe Val
    370                 375                 380

AAT TTG CAG TTT GTT GAA CAA TTT CAA TTA CAA TGT GAA GAT ACG TGT         1200
Asn Leu Gln Phe Val Glu Gln Phe Gln Leu Gln Cys Glu Asp Thr Cys
385                 390                 395                 400

GAT AAA TCC TAT GTA GAA GTG AAA GCT GAC GCT GAT TTT CGA CCT ACT         1248
Asp Lys Ser Tyr Val Glu Val Lys Ala Asp Ala Asp Phe Arg Pro Thr
                405                 410                 415

GGA TAT CGA TTT TGT TGT TCG CGA GTG CCA CGT CAT ATT TTT CAA TCT         1296
Gly Tyr Arg Phe Cys Cys Ser Arg Val Pro Arg His Ile Phe Gln Ser
            420                 425                 430

GCG ACA AAC GAG ATG GTA GTA ATA TTT CGC GGT TTT GGT GGT GCG GGA         1344
Ala Thr Asn Glu Met Val Val Ile Phe Arg Gly Phe Gly Gly Ala Gly
        435                 440                 445

AAT GGC TTT AAA GCT AAA ATT TGG TCA AAC GTA GAT GAT GAT ATA GCT         1392
Asn Gly Phe Lys Ala Lys Ile Trp Ser Asn Val Asp Asp Asp Ile Ala
    450                 455                 460

AAT ACA ATT GTA ACA ACT GAA ATG GCA AAA ATT TCG GAA AAA ATA CCG         1440
Asn Thr Ile Val Thr Thr Glu Met Ala Lys Ile Ser Glu Lys Ile Pro
465                 470                 475                 480

AAG CTA ACA GTT CCA ATA GTT AAA ACT ATT ACC ACT CCT ACA ATA ACA         1488
Lys Leu Thr Val Pro Ile Val Lys Thr Ile Thr Thr Pro Thr Ile Thr
                485                 490                 495

ACT ACT ACT GCT TTC ATG ATA TCA CCC AAG AAA GGC AAT GTC ACC GCC         1536
Thr Thr Thr Ala Phe Met Ile Ser Pro Lys Lys Gly Asn Val Thr Ala
            500                 505                 510

ACG AGA GTT GCT ATC ACT ACT ACG CCG ACT ACT ACA ATT ACT ACG ACT         1584
Thr Arg Val Ala Ile Thr Thr Thr Pro Thr Thr Thr Ile Thr Thr Thr
        515                 520                 525

ATT GCC GGT ACG GTA CCA ATC ACC GTA ACT AAT AAT ACT ACC CCT GTA         1632
Ile Ala Gly Thr Val Pro Ile Thr Val Thr Asn Asn Thr Thr Pro Val
    530                 535                 540

GTA AGT GAA ACT TTA CCA TCA TTG CCA GTC AAG ATT CGA AAC AAA ATA         1680
Val Ser Glu Thr Leu Pro Ser Leu Pro Val Lys Ile Arg Asn Lys Ile
545                 550                 555                 560

GGT GCA TGC GAA TGT GGT GAA TGG ACA GAA TGG ACA GGT CCA TGC TCT         1728
Gly Ala Cys Glu Cys Gly Glu Trp Thr Glu Trp Thr Gly Pro Cys Ser
                565                 570                 575

CAA GAA TGT GGC GGT TGC GGA AAA CGT CTT CGA ACA CGT CAG TGT TCA         1776
Gln Glu Cys Gly Gly Cys Gly Lys Arg Leu Arg Thr Arg Gln Cys Ser
            580                 585                 590

TCA GAT ACG GAA TGT AGA ACA GAA GAA AAA CGT GCG TGT GCT TTT AAA         1824
Ser Asp Thr Glu Cys Arg Thr Glu Glu Lys Arg Ala Cys Ala Phe Lys
        595                 600                 605

GTT TGC CCA TAC GGG ACT AAT TTC CTT ATC AAT AAT GGA GAG TTT CAT         1872
Val Cys Pro Tyr Gly Thr Asn Phe Leu Ile Asn Asn Gly Glu Phe His
    610                 615                 620
```

```
ATA CTT TGG AAG GGC TGC TGT GTT GGT CTA TTC CGA TCG GGA GAT ATG   1920
Ile Leu Trp Lys Gly Cys Cys Val Gly Leu Phe Arg Ser Gly Asp Met
625                 630                 635                 640

TGT TCA GCA CTT GAT GAT AAC GAG AAT CCA TTT CTG AAA TTT CTA GAA   1968
Cys Ser Ala Leu Asp Asp Asn Glu Asn Pro Phe Leu Lys Phe Leu Glu
                645                 650                 655

TCA CTG TTG AAC ATG CAA GAT TCT CGA AAA AAC GAT AAT TTG CCT GAC   2016
Ser Leu Leu Asn Met Gln Asp Ser Arg Lys Asn Asp Asn Leu Pro Asp
            660                 665                 670

TCG AAA AAG AAG                                                    2028
Ser Lys Lys Lys
        675
```

(2) INFORMATION FOR SEQ ID NO:34:

(i) SEQUENCE CHARACTERISTICS:
        (A) LENGTH: 676 amino acids
        (B) TYPE: amino acid
        (D) TOPOLOGY: linear (ii) MOLECULE TYPE: protein (xi) SEQUENCE DESCRIPTION: SEQ ID NO:34:

```
Gln Ser Val Glu Asn Tyr Arg Thr Gln Lys Ala Ser Arg Asn Thr Leu
  1               5                  10                  15

Asp His Ile Lys Gln Leu Ile Thr Leu Asn Val Gln Arg Glu Ile Gly
             20                  25                  30

Asn Ile Asp Asp Lys Thr Leu Ala Asp Glu Ile Val Leu Gln Arg Arg
         35                  40                  45

Asp Pro Glu Ala Lys Trp His His Asn Glu Leu Phe Ile Asn Asp Pro
     50                  55                  60

Asp Ala Tyr Tyr Gln Gly Asp Val Asp Leu Ser Glu Lys Gln Ala Glu
 65                  70                  75                  80

Ile Leu Ser Glu His Phe Lys Asn Glu Ile Ala Leu Thr Glu Lys Asp
                 85                  90                  95

Asp Thr Ile Ile Arg Arg Lys Lys Ser Ile Gly Arg Glu Pro Phe Tyr
            100                 105                 110

Val Arg Trp Asn His Lys Arg Pro Ile Ser Tyr Glu Phe Ala Glu Ser
        115                 120                 125

Ile Pro Leu Glu Thr Arg Arg Lys Ile Arg Ser Ala Ile Ala Met Trp
    130                 135                 140

Glu Glu Arg Thr Cys Ile Arg Phe Gln Glu Asn Gly Pro Asn Val Asp
145                 150                 155                 160

Arg Ile Val Phe Asn Asp Gly Gly Cys Ser Ser Phe Val Gly Arg
                165                 170                 175

Thr Gly Gly Thr Pro Gly Ile Ser Ile Ser Thr Pro Gly Cys Asp Ile
            180                 185                 190

Ile Gly Ile Ile Ser His Glu Ile Gly His Thr Leu Gly Ile Phe His
        195                 200                 205

Glu Gln Ala Arg Arg Asp Gln Lys Asn His Ile Phe Ile Asn Tyr Asn
    210                 215                 220

Asn Ile Pro Ser Ser Arg Trp Asn Asn Phe Phe Pro Leu Ser Glu Tyr
225                 230                 235                 240

Glu Ala Asp Met Phe Asn Leu Pro Tyr Asp Thr Gly Ser Val Met His
                245                 250                 255

Tyr Gly Ser Tyr Gly Phe Ala Arg Asn Pro Tyr Glu Pro Thr Ile Thr
            260                 265                 270
```

-continued

```
Thr Arg Asp Lys Phe Gln Gln Tyr Thr Ile Gly Gln Arg Glu Gly Pro
        275                 280                 285

Ser Phe Leu Asp Tyr Ala Ser Ile Asn Ser Ala Tyr Arg Cys Thr Glu
    290                 295                 300

Gln Cys Ala Asp Met His Cys Asp His Asn Gly Tyr Pro Asp Pro Asn
305                 310                 315                 320

Asn Cys Ala Lys Cys Leu Cys Pro Asp Gly Phe Ala Gly Arg Thr Cys
                325                 330                 335

Gln Phe Val Gln Tyr Thr Ser Cys Gly Ala Leu Ile Lys Ala Arg Lys
            340                 345                 350

Met Pro Val Thr Ile Ser Ser Pro Asn Tyr Pro Asn Phe Phe Asn Val
            355                 360                 365

Gly Asp Gln Cys Ile Trp Leu Leu Thr Ala Pro Arg Gly Phe Val
    370                 375                 380

Asn Leu Gln Phe Val Glu Gln Phe Gln Leu Gln Cys Glu Asp Thr Cys
385                 390                 395                 400

Asp Lys Ser Tyr Val Glu Val Lys Ala Asp Ala Asp Phe Arg Pro Thr
                405                 410                 415

Gly Tyr Arg Phe Cys Cys Ser Arg Val Pro Arg His Ile Phe Gln Ser
            420                 425                 430

Ala Thr Asn Glu Met Val Val Ile Phe Arg Gly Phe Gly Gly Ala Gly
        435                 440                 445

Asn Gly Phe Lys Ala Lys Ile Trp Ser Asn Val Asp Asp Ile Ala
    450                 455                 460

Asn Thr Ile Val Thr Thr Glu Met Ala Lys Ile Ser Glu Lys Ile Pro
465                 470                 475                 480

Lys Leu Thr Val Pro Ile Val Lys Thr Ile Thr Thr Pro Thr Ile Thr
                485                 490                 495

Thr Thr Thr Ala Phe Met Ile Ser Pro Lys Lys Gly Asn Val Thr Ala
            500                 505                 510

Thr Arg Val Ala Ile Thr Thr Thr Pro Thr Thr Thr Ile Thr Thr Thr
        515                 520                 525

Ile Ala Gly Thr Val Pro Ile Thr Val Thr Asn Asn Thr Thr Pro Val
    530                 535                 540

Val Ser Glu Thr Leu Pro Ser Leu Pro Val Lys Ile Arg Asn Lys Ile
545                 550                 555                 560

Gly Ala Cys Glu Cys Gly Glu Trp Thr Glu Trp Thr Gly Pro Cys Ser
                565                 570                 575

Gln Glu Cys Gly Gly Cys Gly Lys Arg Leu Arg Thr Arg Gln Cys Ser
            580                 585                 590

Ser Asp Thr Glu Cys Arg Thr Glu Glu Lys Arg Ala Cys Ala Phe Lys
        595                 600                 605

Val Cys Pro Tyr Gly Thr Asn Phe Leu Ile Asn Asn Gly Glu Phe His
    610                 615                 620

Ile Leu Trp Lys Gly Cys Cys Val Gly Leu Phe Arg Ser Gly Asp Met
625                 630                 635                 640

Cys Ser Ala Leu Asp Asp Asn Glu Asn Pro Phe Leu Lys Phe Leu Glu
                645                 650                 655

Ser Leu Leu Asn Met Gln Asp Ser Arg Lys Asn Asp Asn Leu Pro Asp
            660                 665                 670

Ser Lys Lys Lys
        675
```

-continued (2) INFORMATION FOR SEQ ID NO:35:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

CATCTCGAGA TCAGTGGAAA ATTATCGAAC G        31

(2) INFORMATION FOR SEQ ID NO:36:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

ATTGAATTCA CTTCTTTTTC GAGTCAGGCA A        31

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. An isolated nucleic acid molecule selected from the group consisting of
    (a) an isolated *D. immitis* nucleic aicd molecule selected om the group consisting of; (A) a *D. immitis* astacin metalloendopeptidase cDNA molecule and (B) a *D. immitis* astacin metallocndopeptidase mRNA molecule.

2. The isolated nucleic acid molecule of claim 1, wherein said cDNA or mRNA molecule comprises at lcast 36 contiguous nucleotides of a nucleic acid molecule selected from the group consisting of nDiMPA1$_{1299}$ (comprising a coding strand having SEQ ID NO:1, and a strand complementary to SEQ NO:1), nDiMP2$_{2126}$ (comprising a coding strand having SEQ ID NO:2, and a strand complementary SEQ ID NO:2), L3 nDiMPA3$_{2292}$ (comprising a coding strand having SEQ ID NO:29, and a strand complementary to SEQ ID NO:29), L3 nDiMPA3$_{2076}$ (comprising a coding stand having SEQ ID NO:30, and a strand complementary to SEQ ID NO:30), adult nDiMPA3$_{2032}$ (comprising a coding strand having SEQ D NO:32, and a strand complementary to SEQ ID NO:32), and adult nDiMPA3$_{2028}$ (comprising a coding strand having SEQ ID NO:33, and a strand complementary to SEQ ID NO:33), wherein, in said mRNA molecule, the deoxynucleotide T of SEQ ID NO:1, SEQ ID NO:2, SEQ ID NO:20, SEQ ID NO:29, SEQ ID N30, SEQ ID NO:32, and SEQ ID NO:33 is replaced by the ribonucleotide U.

3. The isolated nucleic acid molecule of claim 1, wherein said cDNA or mRNA molecule encodes a protein comprising an amino acid sequence selected from the group consisting of: SEQ ID NO:4, SEQ ID NO:7, SEQ ID NO:31, and SEQ ID NO:34.

4. The isolated nucleic acid molecule of claim 1, wherein said protein comprises an amino acid sequence selected from the group consisting of SEQ ID NO:31 SEQ ID NO:34.

5. The isolated nucleic acid molecule of claim 1, wherein said nucleic acid molecule encodes a protein that, when administered to an animal, clicits an antibody response against a parasite astacin metalloendopeptidase.

6. The isolated nucleic acid molecule of claim 1, wherein said cDNA or mRNA molecule comprises a portion of a nucleic acid sequence selected from the group consist of SEQ ID NO:1, SEQ ID NO:2, SEQ ID NO:20, SEQ ID NO:21, SEQ ID NO:22, SEQ ID NO:29, SEQ ID NO: 30, SEQ ID NO:32, SEQ ID NO:33, and complements of SEQ ID NO:1, SEQ ID NO:2. SEQ ID NO:20, SEQ ID NO:21, SEQ ID NO:22, SEQ ID NO:29, SEQ ID NO: 30, SEQ ID NO:32 and SEQ ID NO:33, wherein said portion comprises an at least 36 contiguous nucleotide region identical in sequence to a at least 36 contiguous nucleotide region of any of said nucleic acid sequences. clicits an antibody response against a parasite astacin metalloendopeptidase.

7. An isolated nucleic acid molecule, wherein said nucleic acid molecule cores a nucleic aid sequence selected from the group consisting of SEQ ID NO:1, SEQ ID NO:2, SEQ ID NO:20,SEQ ID NO:21, SEQ ID NO:22, SEQ ID NO:29, SEQ ID NO: 30, SEQ ID NO:32, and SEQ ID NO:33.

8. A recombinant molecule comprising at least one isolated cDNA or mRNA molecule set forth in claim 1 operatively linked to at least one transcription control sequence.

9. A recombinant cell comprising a cell having at least one cDNA or mRNA molecule set forth in claim 1, said cell expressing said nucleic acid molecule.

10. A composition comprising an isolated parasite nucleic acid molecule selected from the group consisting of: a cDNA molecule and an mRNA molecule, wherein said nucleic acid molecule comprises a nucleic acid sequence selected from the group consisting of:
    (a) a nucleic acid sequence from the group consisting of: SEQ ID NO: 1, SEQ ID NO:2, SEQ ID NO:20, SEQ ID NO:21, SEQ ID NO:22, SEQ ID NO:29, SEQ ID NO:30, SEQ ID NO:32, and SEQ ID NO:33;
    (b) a nucleic acid sequence comprising at least 36 contiguous nucleotides of a nucleic acid sequence selected from the group consisting of SEQ ID NO:1, SEQ ID NO:2, SEQ ID NO:20, SEQ ID NO:21, SEQ ID NO:22, SEQ ID NO:29, SEQ ID NO:30, SEQ ID NO:32, and SEQ ID NO:33, wherein said nucleic acid sequence comprises a nucleic acid sequence which encodes an extended zinc binding domain; and (c) a complement of a nucleic acid sequence of (a) or (b).

11. An isolated nucleic acid molecule selected from the group consisting of a cDNA molecule and an mRNA molecule, wherein said nucleic acid molecule comprises a nucleic acid sequence selected from the group consisting of:

(a) a nucleic acid sequence selected from the group consisting of: SEQ ID NO:1, SEQ ID NO:2, SEQ ID NO:20, SEQ ID NO:21, SEQ ID NO:22, SEQ ID NO:29, SEQ ID NO:30, SEQ ID NO:32, and SEQ ID NO:33;

(b) a nucleic acid sequence comprising at least 36 contiguous nucleotides of a nucleic acid sequence selected from the group consisting of SEQ ID NO:1, SEQ ID NO:2, SEQ ID NO:20, SEQ ID NO:21, SEQ ID NO:22, SEQ ID NO:29, SEQ ID NO:30, SEQ ID NO:32, and SEQ ID NO:33, wherein said nucleic acid sequence comprises a nucleic acid sequence which encodes an extended zinc binding domain; and (c) a complement of a nucleic acid sequence of (a) or (b).

12. The isolated nucleic acid molecule of claim 11, wherein said cDNA or mRNA molecule encodes a protein comprising an amino acid sequence selected from the group consisting of: SEQ ID NO:4, SEQ ID NO:7, SEQ ID NO:31 and SEQ ID NO:34.

13. The isolated nucleic acid molecule of claim 11, wherein said nucleic acid molecule encodes a protein that, when administered to an animal, elicits an antibody response against a parasite astacin metalloendopeptidase.

14. An isolated nucleic acid molecule selected from the group consisting of:

(a) a nucleic acid molecule selected from the group consisting of: (A) a *D. immitis* astacin metalloendopeptidase cDNA molecule and (B) a *D. immitis* astacin metalloendopeptidase mRNA molecule, wherein said nucleic acid molecule of (A) or (B) has a nucleic acid sequence that hybridizes under conditions comprising (i) hybridizing in a solution consisting of 2×SSPE, 1% Sarkosyl, 5×Denhardts and 0.1 mg/ml denatured salmon sperm and (ii) washing in a solution consisting of 2×SSPE and 1% Sarkosyl, at 55° C.; with be complement of a nucleic acid sequence that encodes a protein having an amino acid sequence selected from the group consisting of: SEQ ID NO:4, SEQ ID NO:7, SEQ ID NO:31 and SEQ ID NO:34; and wherein said nucleic acid molecule encodes a protein having astacin metalloendopeptidase activity; and (b) a nucleic acid molecule comprising a nucleic acid sequence fully complementary to a nucleic acid sequence of (a).

15. The isolated nucleic acid molecule of claim 14, wherein said cDNA or mRNA molecule comprises at 1cast 36 contiguous nucleotides of a nucleic acid molecule selected from the group consisting of $nDiMPA1_{1299}$ (comprising a coding strand having SEQ ID NO:1, and a stand complementary to SEQ ID NO:1), $nDiMPA2_{2126}$ (comprising a coding strand having SEQ ID NO:2, and a strand complementary to SEQ ID NO:2), L3 $nDiMPA3_{2292}$ (comprising a coding strand having SEQ ID NO:29, and a strand complementary to SEQ ID NO:29), L3 $nDiMPA3_{2076}$ (comprising a coding strand having SEQ ID NO:30, and a strand complementary to SEQ ID NO:30), adult $nDiMPA3_{2032}$ (comprising a coding strand having SEQ ID NO:32, and a strand complementary to SEQ ID NO:32), and adult $nDiMPA3_{2028}$ (comprising a coding stand having SEQ ID NO:33, and a strand complementary to SEQ ID NO:33), and wherein, in said mRNA molecule, the deoxynucleotide T of SEQ ID NO:1, SEQ ID NO:2, SEQ ID NO:20, SEQ ID NO29, SEQ ID NO:30, SEQ ID NO:32, and SEQ ID NO:33 is replaced by the ribonucleotide U.

16. The isolated nucleic acid molecule of claim 14, wherein said cDNA or mRNA molecule encodes a protein comprising an amino acid sequence selected from the group consisting of: SEQ ID NO:4, SEQ ID NO:7, SEQ D NO:31, and SEQ ID NO:34.

17. The isolated nucleic acid molecule of claim 14, wherein said nucleic acid molecule encodes a protein that when administered to an animal, elicits an antibody response against a parasite astacin metalloendopeptidase.

18. The isolated nucleic acid molecule of claim 14, wherein said cDNA or mRNA molecule comprises a nucleic acid sequence selected from the group consisting of SEQ ID NO: 1, SEQ ID NO:2, SEQ ID NO:20, SEQ ID NO:21, SEQ ID NO:22, SEQ ID NO:29, SEQ ID NO:30, SEQ ID NO:32, SEQ ID NO:33, and complements of SEQ ID NO:1, SEQ ID NO:2, SEQ ID NO:20, SEQ ID NO:21, SEQ ID NO:22, SEQ ID NO:29, SEQ ID NO: 30, SEQ ID NO:32 and SEQ ID NO:33.

19. A method to produce an astacin metalloendopeptidase protein, said method comprising culturing in an effective medium a recombinant cell expressing said protein, wherein said protein is encoded by a nucleic acid molecule selected from the group consisting of a cDNA molecule and an mRNA molecule, wherein said nucleic acid molecule comprises a nucleic acid sequence selected from the group consisting of:

(a) a nucleic acid sequence selected from the group consisting of SEQ ID NO:1, SEQ ID NO:2, SEQ ID NO:20, SEQ ID NO:21, SEQ ID NO:22, SEQ ID NO:29, SEQ ID NO:30, SEQ ID NO:32, and SEQ ID NO:33; and, (b) a nucleic acid sequence comprising at least 36 contiguous nucleotides of a nucleic acid sequence selected from the group consisting of SEQ ID NO:1, SEQ ID NO:2, SEQ ID NO:20, SEQ ID NO:21, SEQ ID NO:22, SEQ ID NO:29, SEQ ID NO:30, SEQ ID NO:32, and SEQ ID NO:33, wherein said nucleic acid sequence, comprises a nucleic acid sequence which encodes an extended zinc binding domain.

* * * * *

UNITED STATES PATENT AND TRADEMARK OFFICE
CERTIFICATE OF CORRECTION

PATENT NO. : 6,281,345 B1
DATED : August 28, 2001
INVENTOR(S) : Tripp et al.

It is certified that error appears in the above-identified patent and that said Letters Patent is hereby corrected as shown below:

Column 93,
Line 35, please delete "selcctcd" and replace with -- selected --;
Line 37, please delete "aicd" and replace with -- acid --;
Line 38, please delete "om" and replace with -- from --;
Line 40, please delete "metallocndopeptidase" and replace with
-- metalloendopeptidase --;
Line 42, please delete "lcast" and replace with -- least --;

Column 94,
Line 31, please delete "clicits" and replace with -- elicits --;
Line 35, please delete "consist" and replace with -- consisting --;
Line 43, please delete "a at" and replace with -- an at --;
Line 44, please delete "clicits an antibody response against a parasite astacin metalloendopeptidase";
Line 47, please delete "cores" and replace with -- comprises --;

Column 95,
Line 34, please delete "clicits" and replace with -- elicits --;
Line 47, please delete "be" and replace with -- the --;
Line 58, please delete "lcast" and replace with -- least --.

Signed and Sealed this

Twenty-first Day of September, 2004

JON W. DUDAS
*Director of the United States Patent and Trademark Office*